US007585964B2

(12) United States Patent
Palanisamy et al.

(10) Patent No.: US 7,585,964 B2
(45) Date of Patent: Sep. 8, 2009

(54) METHODS OF ANALYZING CHROMOSOMAL TRANSLOCATIONS USING FLUORESCENCE IN SITU HYBRIDIZATION (FISH)

(75) Inventors: Nallasivam Palanisamy, North Andover, MA (US); Raju S. Chaganti, New York, NY (US)

(73) Assignee: Cancer Genetics, Inc., Cambridge, MA (US)

( * ) Notice: Subject to any disclaimer, the term of this patent is extended or adjusted under 35 U.S.C. 154(b) by 0 days.

(21) Appl. No.: 10/146,658

(22) Filed: May 14, 2002

(65) Prior Publication Data

US 2002/0192692 A1 Dec. 19, 2002

Related U.S. Application Data

(60) Provisional application No. 60/357,195, filed on Feb. 13, 2002, provisional application No. 60/337,653, filed on Nov. 8, 2001, provisional application No. 60/291,121, filed on May 14, 2001.

(51) Int. Cl.
*C07H 21/04* (2006.01)
*C07H 21/02* (2006.01)
*C07H 21/00* (2006.01)
*C12Q 1/68* (2006.01)
*C12P 19/34* (2006.01)

(52) U.S. Cl. .................. 536/24.3; 536/23.1; 536/24.31; 536/24.33; 536/25.3; 536/25.32; 435/6; 435/91.1

(58) Field of Classification Search ..................... 435/6, 435/91.1, 183, 462, 463; 436/94; 536/23.1, 536/24.3, 25.33, 25.3, 25.32, 24.31
See application file for complete search history.

(56) References Cited

U.S. PATENT DOCUMENTS

| | | | |
|---|---|---|---|
| 4,559,305 A | 12/1985 | Zajic et al. | |
| 4,681,840 A | 7/1987 | Stephenson et al. | |
| 5,057,410 A | 10/1991 | Kawasaki et al. | |
| 5,447,841 A | 9/1995 | Gray et al. | |
| 5,491,224 A | 2/1996 | Bittner et al. | |
| 5,538,869 A | 7/1996 | Siciliano et al. | |
| 5,663,319 A | 9/1997 | Bittner et al. | |
| 5,817,462 A | 10/1998 | Garini et al. | |
| 5,856,097 A | 1/1999 | Pinkel et al. | |
| 5,871,932 A | 2/1999 | Bar-Am et al. | |
| 6,007,994 A * | 12/1999 | Ward et al. | 435/6 |
| 6,025,126 A | 2/2000 | Westbrook | |
| 6,280,929 B1 | 8/2001 | Gray et al. | |
| 6,576,421 B1 * | 6/2003 | Westbrook | 435/6 |

FOREIGN PATENT DOCUMENTS

| | | |
|---|---|---|
| EP | 0 444 115 B1 | 8/1996 |
| EP | 0 430 402 B1 | 1/1999 |
| WO | WO 00/21975 A1 | 4/2000 |

OTHER PUBLICATIONS

Vocero-Akbani et al., Mapping human telomere regions with YAC and P1 clones: chromosome-specific markers for 27 telomeres including 149 STSs and 24 polymorphisms for 14 proterminal regions. Genomics, 36, 492-506, 1996.*
Dunham et al., The DNA sequence of human chromosome 22. Nature, 402, 489-495, Dec. 1999.*
Habuchi et al., A novel candidate tumor suppressor locus at 9q32-33 in bladder cancer: localization of the candidate region within a single 840 kb YAC. Human Molecular Genetics, 6, 913-919, 1997.*
Konigsberg, et al., Predictive Role of Interphase Cytogenetics for Survival of Patients With Multiple Myeloma. Journal of Clinical Oncology, 18, 804-812, Feb. 2000.*
Rack et al., FISH detection of chromosome 14q32/IgH translocations: evaluation in follicular lymphoma. British Journal of Haematology, 103, 495-504, 1998.*
Attachment for cyclin D-1 probe.*
Barker et al., Regional location of T cell receptor gene Ti alpha on human chromosome 14. J. exp. Med., 162, 387-392, 1985.*
Nusbaum et al., DNA sequence and analysis of human chromosome 8. Nature 439, 331-335, Jan. 19, 2006. Humphray et al., DNA sequence and analysis of human chromosome 9. Nature 429, 369-374, May 27, 2004. Todd et al., Human chromosome 11 DNA sequence and analysis including novel gene identification. Nature, 440, 497-500, Mar. 23, 2006.*
Heilig et al., The DNA sequence and analysis of human chromosome 14. Nature, 42, 601-607, Feb. 6, 2003. Nusbaum et al., DNA sequence and analysis of human chromosome 18. Nature 437, 551-555, Sep. 22, 2005.*
Dunham et al., DNA sequence of human chromosome 22. Nature 402, 489-495, Dec. 2, 1999.*
Voorter, C. et al. "Loss of Chromosome 11 and 11 P/Q imbalances in Bladder Cancer Detected by Fluorescence In Situ Hybridization", *Int. J. Cancer*, 1996, pp. 301-307, vol. 65.
Anastasi, John, et al; Interphase Cytogenetic Analysis Detects Minimal Residual Disease in a Case of Acute Lymphoblastic Leukemia and Resolves the Question of Origin of Relapse After Allogeneic Bone Marrow Transplantation; *Blood*; Mar. 1, 1991; pp. 1087-1091; vol. 77, No. 5.

(Continued)

*Primary Examiner*—Frank W Lu
(74) *Attorney, Agent, or Firm*—Townsend and Townsend and Crew, LLP

(57) ABSTRACT

Probes and methods of using the probes to detect chromosomal rearrangements and/or deletions are provided. The methods utilize probes that are free of repeat sequences to provide greater selectivity and sensitivity; methods for producing such probes are also disclosed. The probe sets utilized in the detection methods are designed to hybridize to chromosomes at regions outside known breakpoints, instead of spanning the breakpoint as with conventional FISH methods, and, in some instances, are further designed to bind to regions located outside the genes involved in the rearrangement. Methods utilizing probe sets with two and four colors are also described, as are automated methods for analyzing rearrangements.

11 Claims, 16 Drawing Sheets

OTHER PUBLICATIONS

Arnoldus, E.P.J.; et al.; Detection of the Philadelphia chromosome in interphase nuclei; *Cytogenet Cell Genet*; 1990; pp. 108-111; vol. 54.

Bakhshi, Ajay, et al; Cloning the Chromosomal Breakpoint of t($^{14}/_{18}$) Human Lymphomas: Clustering around $J_H$ on Chromosome 14 near a Transcriptional Unit on 18; *Cell*; Jul. 1985; pp. 899-906; vol. 41.

Benton, W. David, et al.; Screening λgt Recombinant Clones by Hybridization to Single Plaques in situ; ;*Science*; Apr. 8, 1977; pp. 180-182; vol. 196.

Coignet, Lionel J.A., et al.; Detection of 11q13 Rearrangements in Hematologic Neoplasias by Double-Color Fluorescence In Situ Hybridization; *Blood*; Feb. 15, 1996; pp. 1512-1519; vol. 87, No. 4.

Colleoni, Gisele W.B., et al; Comparison of a Multiplex Reverse Transcriptase-Polymerase Chain Reaction for *BCR-ABL* to Fluorescence In Situ Hybridization, Southern Blotting, and Conventional Cytogenetics in the Monitoring of Patients With *PhL*-Positive Leukemias; *Diagnostic Molecular Pathology*; 2000; pp. 203-209; vol. 9, No. 4.

Cotter, Finbarr, et al; Direct Sequence Analysis of the 14q+ and 18q- Chromosome Junctions in Follicular Lymphoma; *Blood*; Jul. 1, 1990; pp. 131-135; vol. 76, No. 1.

Craig, Jeffrey M., et al.; Removal of repetitive sequences from FISH probes using PCR-assisted affinity chromatography; *Human Genetics*; 1997; pp. 472-476; vol. 100.

Cremer, T., et al.; Detection of chromosome aberrations in metaphase and interphase tumor cells by in situ hybridization using chromosome-specific library probes; *Human Genetics*; 1988; pp. 235-246; vol. 80.

Crist, W., et al.; Philadelphia Chromosome Positive Childhood Acute Lymphoblastic Leukemia: Clinical and Cytogenetic Characteristics and Treatment Outcome. A Pediatric Oncology Group Study; *Blood*; Aug. 1, 1990; pp. 489-494; vol. 76, No. 3.

Davison, Jon M.; et al; Subtracted, Unique-Sequence, In Situ Hybridication; *American Journal of Pathology*; Nov. 5, 1998; pp. 1401-1409, vol. 153, No. 5.

Dewald, Gordon, et al.; Highly Sensitive Fluorescence In Situ Hybridization Method to Detect Double BCR/ABL Fusion and Monitor Response to Therapy in Chronic Myeloid Leukemia, *Blood*; May 1, 1998; pp. 3357-3365; vol. 91, No. 9.

Dyomin, Vadim G., et al.; *MUC1* is activated in a B-cell lymphoma by the t(1;14)(q21;q32) translocation and is rearranged and amplified in B-cell lymphoma subsets; *Blood*; Apr. 15, 2000; pp. 2666-2671; vol. 95, No. 8.

Elmaagacli, A.H.; et al.; The amount of BCR-ABL fusion transcripts detected by the real-time quantitative polymerase chain reaction method in patients with Philadelphia chromosome positive chronic myeloid leukemia correlates with the disease stage; *Ann Hematol*; 2000; pp. 424-431; vol. 79.

Fuscoe, James C., et al; An Efficient Method for Selecting Unique-Sequence Clones from DNA Libraries and Its Application to Fluorescent Staining of Human Chromosome 21 Using in Situ Hybridization; *Genomics*; 1989; pp. 100-109; vol. 5.

Gaidano, Gianluca, et al; Biologic and molecular characterization of non-Hodgkin's lymphoma; *Current Opinion in Oncology*; 1993; pp. 776-784; vol. 5.

Gray, J.W., et al; Analytical approaches to detection and characterization of disease-linked chromosome aberrations; *Bone Marrow Transplantation*; 1990; pp. 14-19; vol. 6, Supplement 1.

Kamentsky, Louis, A., Methods for Automatic Multiparameter Analysis of Fluorescence In Situ Hybridized Specimens With a Laser Scanning Cytometer; *Cytometry*; 1997; pp. 117-125; vol. 27.

Kolomietz, Elena, et al.; Primary chromosomal rearrangements of leukemia are frequently accompanied by extensive submicroscopic deletions and may lead to altered prognosis; *Blood*, Jun. 1, 2001; pp. 3581-3588; vol. 97, No. 11.

Lichter, Peter, et al.; High-Resolution Mapping of Human Chromosome 11 by in Situ Hybridization with Cosmid Clones; *Science*; Jan. 5, 1990; pp. 64-69; vol. 247.

Lichter, Peter, et al.; Rapid detection of human chromosome 21 aberrations by in situ hybridization; *Proc. Natl. Acad. Sci. USA*; Dec. 1988; pp. 9664-9668; vol. 85.

Mauer, Jürgen, et al.; Detection of chimeric BCR-ABL genes in acute lymphoblastic leukaemia by the polymerase chain reaction; *The Lancet*; May 4, 1991; pp. 1055-1058; vol. 337.

Mohr, Brigitte, et al.; Problems with interphase fluorescence in situ hybridization in detecting BCR-ABL-positive cells in some patients using a novel technique with extra signals; *Cancer Genetics and Cytogenetics*; 2001; pp. 111-117; vol. 127.

Offit, Kenneth et al; Chromosomal Aberrations in Non-Hodgkin's Lymphoma; *Hematology/Oncology Clinics of North America*; Oct. 1991; pp. 853-869; vol. 5, No. 5.

Offit, Kenneth; Chromosome Analysis in the Management of Patients with Non-Hodgkin's Lymphoma; *Leukemia and Lymphoma*; 1992; pp. 275-282, vol. 7.

Parker, Sheryl L., et al; Cancer Statistics, 1996; *CA—A Cancer Journal for Clinicians*; Jan./Feb. 1996; pp. 5-27; vol. 46, No. 1.

Paskulin, Giorgio A., Pre-Clinical Evaluation of Probes to Detect t(8;21) AML Minimal Residual Disease by Fluorescence In Situ Hybridization; *Genes, Chromosomes & Cancer*; 1998; pp. 144-151; vol. 21.

Poetsch, M., et al; Detection of the t(14;18) Chromosomal Translocation by Interphase Cytogenetics With Yeast-Artificial-Chromosome Probes in Follicular Lymphoma and Nonneoplastic Lymphoproliferation; *Journal of Clinical Oncology*; Mar. 1996; pp. 963-969; vol. 14, No. 3.

Rabbitts T.H.; Chromosomal translocations in human cancer; *Nature*; Nov. 10, 1994; pp. 143-149; vol. 372.

Raffeld, Mark, et al; bcl-1, t(11;14), and Mantle Cell-Derived Lymphomas; *Blood*; Jul. 15, 1991; pp. 259-263; vol. 78, No. 2.

Rimokh, Ruth;, et al.; Detection of the Chromosomal Translocation t(11;14) by Polymerase Chain Reaction in Mantle Cell Lymphomas; *Blood*; Apr. 1, 1994; pp. 1871-1875; vol. 83, No. 7.

Sealey, Paul. G., et al.; Removal of repeated sequences from hybridisation probes; *Nucleic Acids Research*; 1985; pp. 1905-1922; vol. 13, No. 6.

Shiramizu, Bruce, et al; Localization of Breakpoints by Polymerase Chain Reactions in Burkitt's Lymphoma With 8;14 Translocations; *Blood*; May 1, 1990; pp. 1848-1852; vol. 75, No. 9.

Shtalrid, Mordechai; et al.; Analysis of Breakpoints Within the *bcr* Gene and Their Correlation With the Clinical Course of Philadelphia-Positive Chronic Myelogenous Leukemia; *Blood*; Aug. 1988; pp. 485-490; vol. 72, No. 2.

Sinclair; P.B.; Large deletions at the t(9;22) breakpoint are common and may identify a poor-prognosis subgroup of patients with chronic myeloid leukemia; *Blood*; Feb. 1, 2000; pp. 738-744; vol. 95, No. 3.

Tkachuk, D.C.; Detection of *bcr-abl* Fusion in Chronic Myelogeneous Leukemia by in Situ Hybridization; *Science*; Oct. 26, 1990; pp. 559-562; vol. 250.

Trask, Barbara J.; Mapping of Human Chromosome Xq28 by Two-Color Fluorescence In Situ Hybridization of DNA Sequences to Interphase Cell Nuclei; *Am. J. Hum. Genet.*; 1991; pp. 1-15; vol. 48.

Tsujimoto, Yoshihide; et al.; DNA rearrangements in human follicular lymphoma can involve the 5' or the 3' region of the *bcl-2* gene; *Proc. Natl. Acad. Sci. USA*; Mar. 1987; pp. 1329-1331; vol. 84.

Tsujimoto, Yoshihide, et al; Molecular Cloning of the Chromosomal Breakpoint of B-Cell Lymphomas and Leukemias with the t(11;14) Chromosome Translocation; *Science*; Jun. 29, 1984; pp. 1403-1406; vol. 224.

Vaandrager, Jan-Willem, et al.; Interphase FISH Detection of *BCL2* Rearrangement in Follicular Lymphoma Using Breakpoint-Flanking Probes; *Genes, Chromosomes & Cancer*, 2000; pp. 85-94; vol. 27.

Van Soest; et al.; Molecular characterization of a t(5;16) breakpoint in the vicinity of the 5q31 critical region defined in MDS and AML; *Blood* 1997 #3582.

Zech, L., et al.; Characteristic Chromosomal Abnormalities in Biopsies and Lymphoid-Cell Lines from Patients with Burkitt and Non-Burkitt Lymphomas; *Int. J. Cancer*; 1976; pp. 47-56; vol. 17.

\* cited by examiner

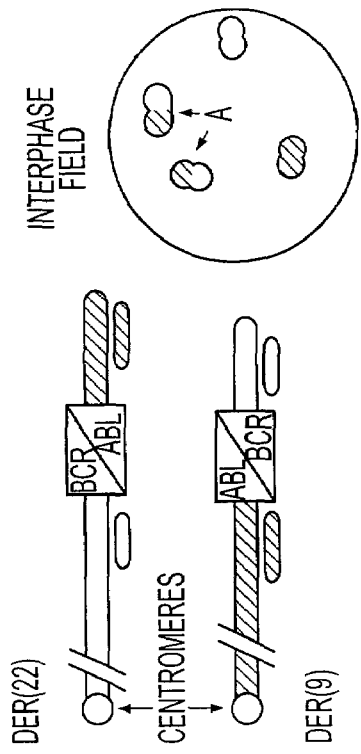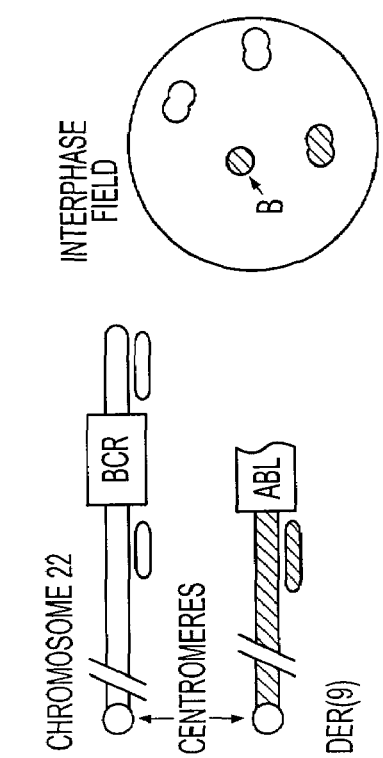
FIG.2A  FIG.2B
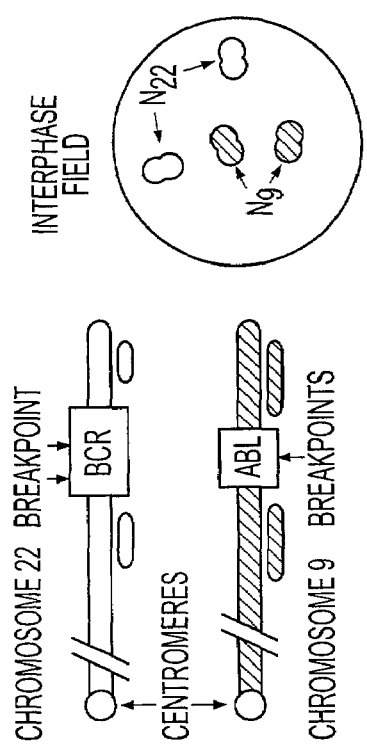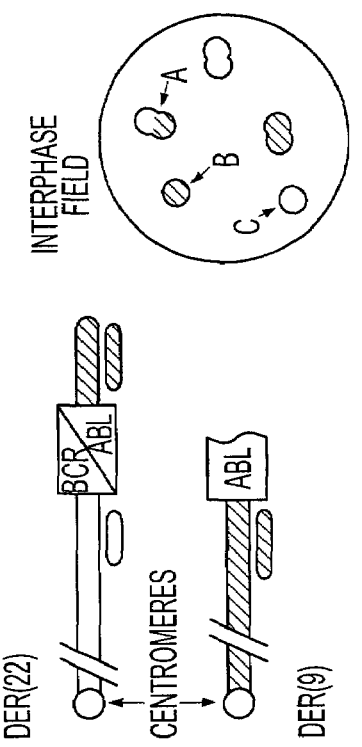
FIG.2C  FIG.2D

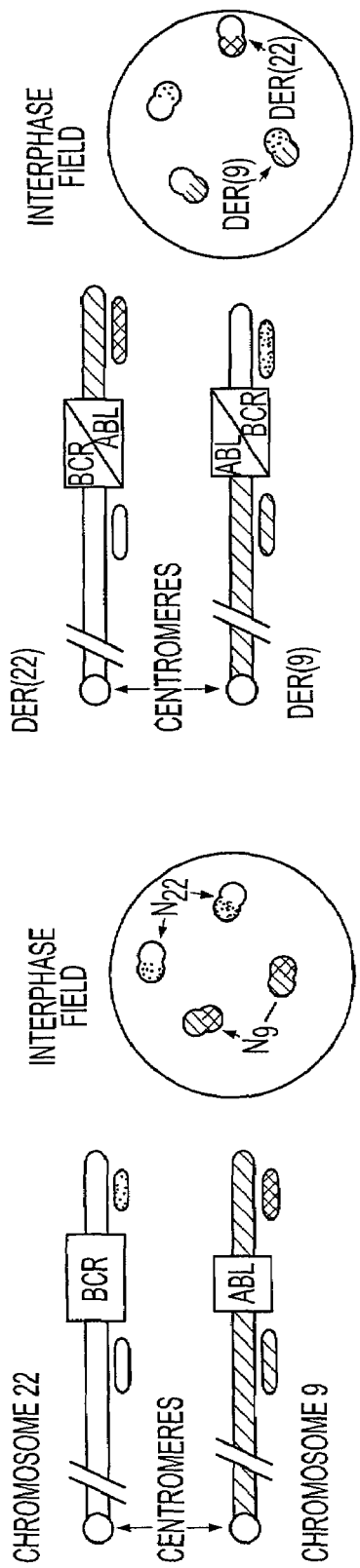
FIG.3A
FIG.3B
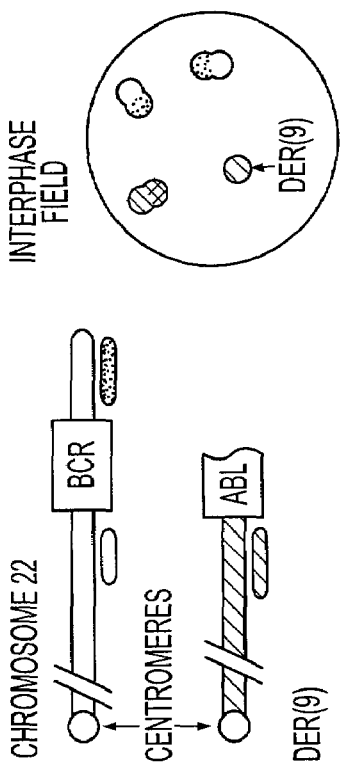
FIG.3D
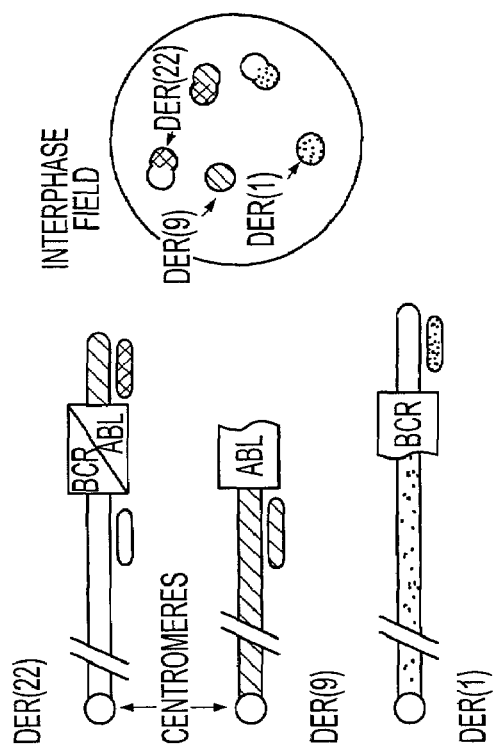
FIG.3C

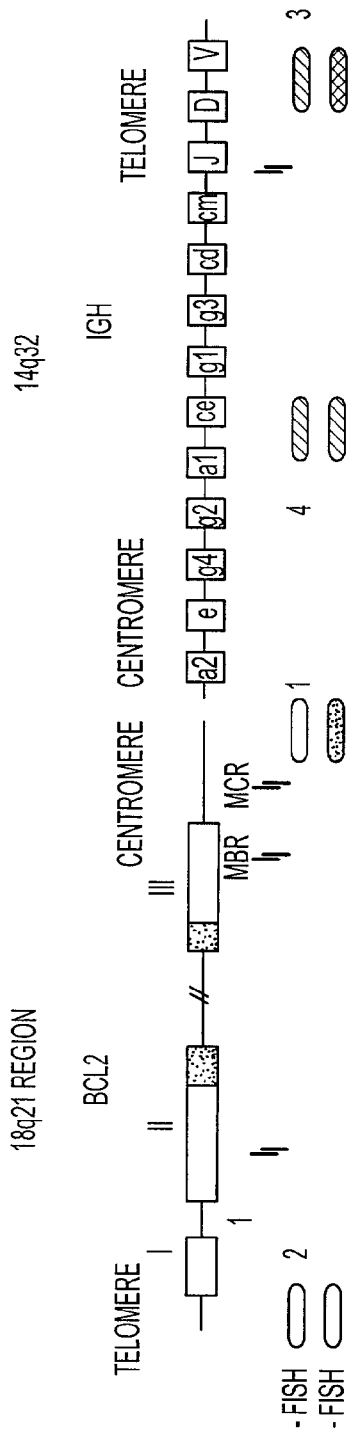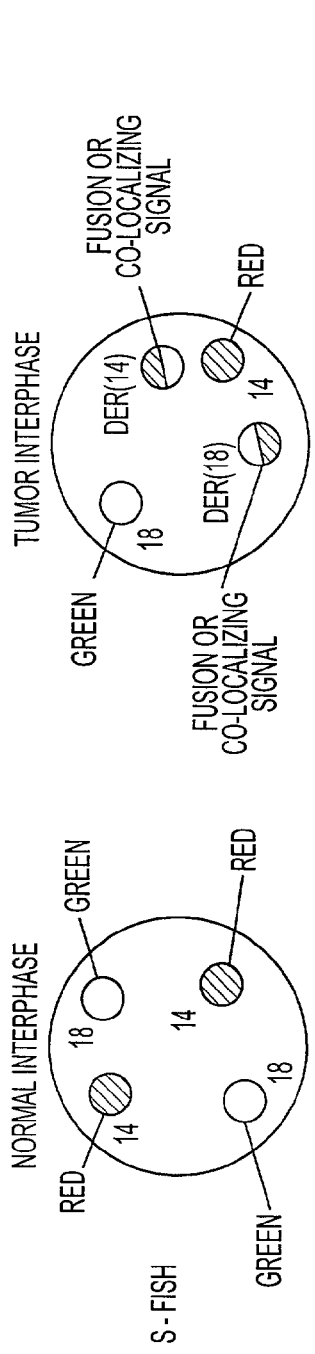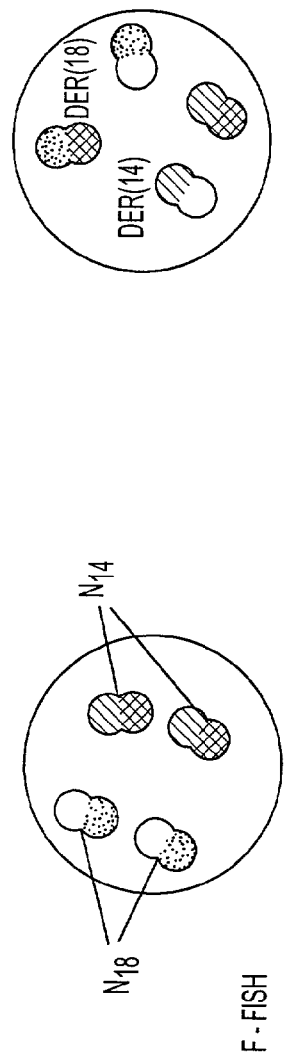
FIG.6A
FIG.6B
FIG.6C

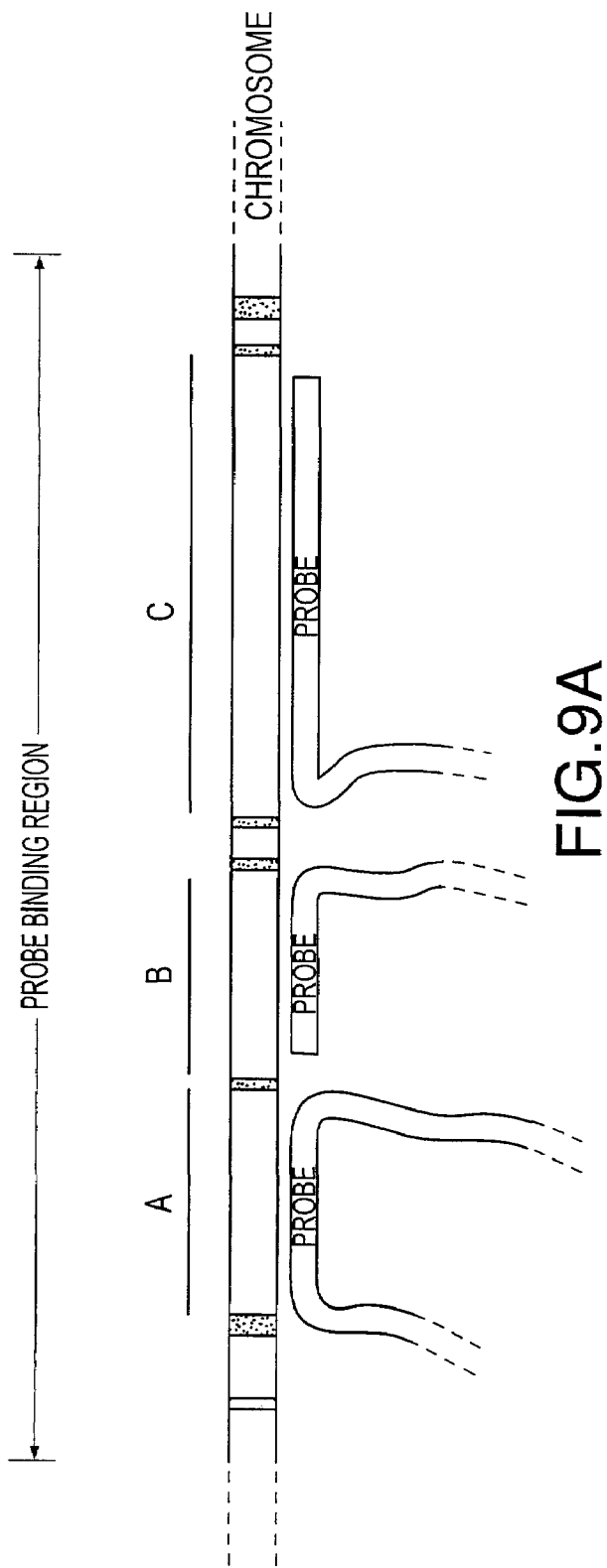
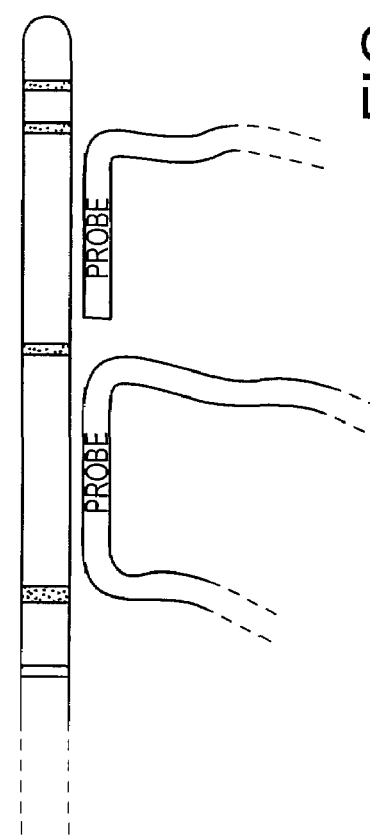
FIG. 9A
FIG. 9B

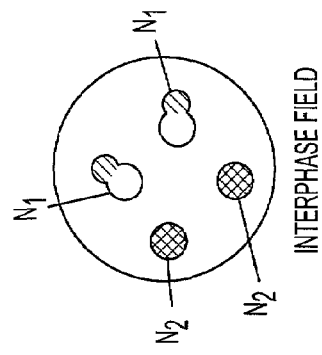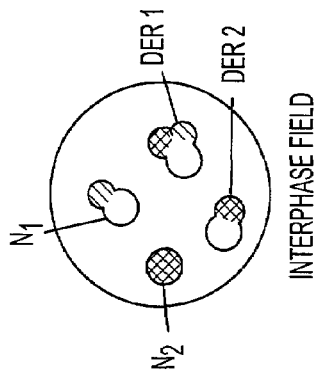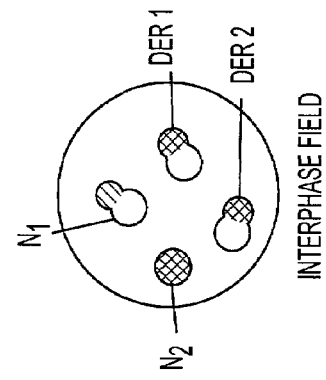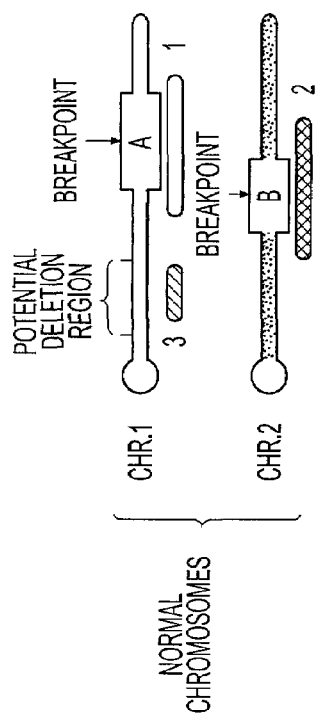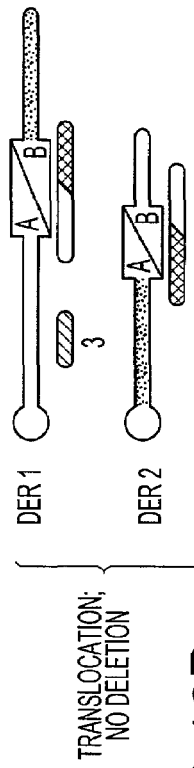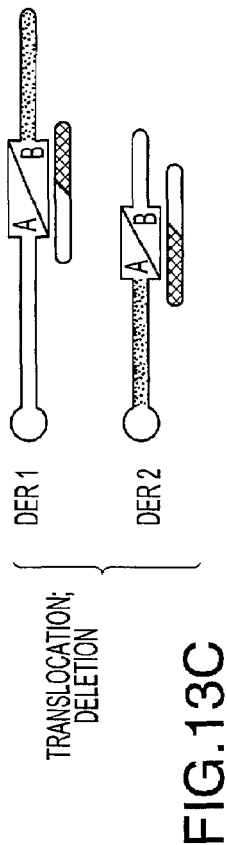
FIG.13A  FIG.13B  FIG.13C

SEQUENCE LISTING

```
<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:probe 1 for
      BCL1 region proximal to MTC region primer F

<400> SEQUENCE: 1
aaggtgtgag gatcactgg                                                19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:probe 1 for
      BCL1 region proximal to MTC region primer R

<400> SEQUENCE: 2
agctcatggg ggctatt                                                  17
```

```
<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:probe 2 for
      BCL1 region telomeric to BCL1 gene region primer F

<400> SEQUENCE: 3
tttctgggtg tgtctgaat                                                  19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:probe 2 for
      BCL1 region telomeric to BCL1 gene region primer R

<400> SEQUENCE: 4
acacagttgc tctaaaggg                                                  19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:probe 3 for
      IGH region sub-telomeric V region of IGH gene
      primer F

<400> SEQUENCE: 5
tgtttgaaga agggagtcgt                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:probe 3 for
      IGH region sub-telomeric V region of IGH gene
      primer R

<400> SEQUENCE: 6
cccactccat gtcttctgtt                                                 20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:probe 4 for
      IGH region Calpha region primer F

<400> SEQUENCE: 7
ccactcagtg tgacctggag cgaa                                            24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:probe 4 for
      IGH region Calpha region primer R

<400> SEQUENCE: 8 ctccccctggc ttttctggaa ctgg                                           24
```

```
<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence:probe 1 for
      MYC region centromeric to all three classes of
      breakpoints in MYC region primer F

<400> SEQUENCE: 9
gtttaagtgg a                                                            11

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:probe 1 for
      MYC region centromeric to all three classes of
      breakpoints in MYC region primer R

<400> SEQUENCE: 10 acagggaat ggttaactgg                                                    20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:probe 2 for
      MYC region telomeric to all three classes of
      breakpoints in MYC region from exon 2 region of
      MYC gene primer F

<400> SEQUENCE: 11
atgcccctca acgttagctt c                                                 21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:probe 2 for
      MYC region telomeric to all three classes of
      breakpoints in MYC region from exon 2 region of
      MYC gene primer R

<400> SEQUENCE: 12
cagagtcgct gctggtggt                                                    19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:probe 3 for
      IGH region sub-telomeric V region of IGH gene
      primer F

<400> SEQUENCE: 13
tgtttgaaga agggagtcgt                                                   20

<210> SEQ ID NO 14
<211> LENGTH: 20
<212> TYPE: DNA
<213> ORGANISM: Artificial Sequence
<220> FEATURE:
```

```
<223> OTHER INFORMATION: Description of Artificial Sequence:probe 3 for
      IGH region sub-telomeric V region of IGH gene
      primer R

<400> SEQUENCE: 14
cccactccat gtcttctgtt                                                    20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:probe 4 for
      IGH region Calpha region primer F

<400> SEQUENCE: 15
ccactcagtg tgacctggag cgaa                                               24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:probe 4 for
      IGH region Calpha region primer R

<400> SEQUENCE: 16
ctcccctggc ttttctggaa ctgg                                               24

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:probe 1 for
      region centromeric to BCL2 gene primer F

<400> SEQUENCE: 17
cttgcctcct aagccagttg                                                    20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence:probe 1 for
      region centromeric to BCL2 gene primer R

<400> SEQUENCE: 18
tggattcatt tctgatcca                                                     19

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:probe 2 for
      region telomeric to BCL2 gene primer F

<400> SEQUENCE: 19
tggccagcag cagtgtcaaa tag                                                23

<210> SEQ ID NO 20
<211> LENGTH: 20
<212> TYPE: DNA
<213> ORGANISM: Artificial Sequence
<220> FEATURE:
```

```
<223> OTHER INFORMATION: Description of Artificial Sequence:probe 2 for
      region telomeric to BCL2 gene primer R

<400> SEQUENCE: 20
ggtgatcgtt aggactccca                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:probe 3 for
      region telomeric to IGH-J gene from
      sub-telomeric region of chromosome 14q primer F

<400> SEQUENCE: 21
tgtttgaaga agggagtcgt                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:probe 3 for
      region telomeric to IGH-J gene from
      sub-telomeric region of chromosome 14q primer R

<400> SEQUENCE: 22
cccactccat gtcttctgtt                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:probe 4 for
      region centromeric to IGH-J gene from Calpha
      region primer F

<400> SEQUENCE: 23
ccctggacgc ttttcaaata                                                  20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:probe 4 for
      region centromeric to IGH-J gene from Calpha
      region primer R

<400> SEQUENCE: 24
gactcaggca aggacaaagc                                                  20
```

METHODS OF ANALYZING CHROMOSOMAL TRANSLOCATIONS USING FLUORESCENCE IN SITU HYBRIDIZATION (FISH)

CROSS-REFERENCES TO RELATED APPLICATIONS

This application claims the benefit of U.S. Provisional Application No. 60/291,121, filed May 14, 2001; No. 60/337,653, filed Nov. 8, 2001, and No. 60/357,195, filed Feb. 13, 2002. Each of these applications is incorporated herein by reference in its entirety for all purposes.

STATEMENT AS TO RIGHTS TO INVENTIONS MADE UNDER FEDERALLY SPONSORED RESEARCH AND DEVELOPMENT

One or more, but not all, of the inventions herein were made with support from Grant Nos. 1R43CA84838-01, R44CA84838-02, and 1R43CA89970-01 awarded by the National Cancer Institute of the National Institutes of Health. Therefore, the government may have certain rights in some of the inventions herein.

BACKGROUND

Chromosomal rearrangements can take a variety of forms including exchanges of portions of one chromosome with another chromosome (translocations), deletion of sections of chromosomes, insertions of new material into the chromosome, and duplications or deletions of entire chromosomes. In the majority of cases, a direct causal link between a particular chromosomal rearrangement and a particular disease state has been found. This concomitant occurrence of disease with a chromosomal rearrangement can frequently be shown to result from alterations made in particular genes directly implicated in promoting the disease.

The use of chromosome rearrangements as diagnostic and follow-up markers is based on several considerations. First, rearrangements are common in hematological malignancies and solid tumors and, as just indicated, the genes that are altered by the rearrangements are directly implicated in the development of malignancy. Second, rearrangements remain as clonal markers of the tumor cells throughout the progression of the disease. Third, rearrangements can be detected by cytogenetic or molecular methods. Examples of rearrangements that are currently useful in diagnostic, prognostic and follow-up evaluation of hematologic and solid tumor neoplasms are listed in Table 1 and Table 2 infra.

Chromosome Translocations in Lymphomas. A number of chromosomal translocations have been identified as being correlated with certain lymphomas, including Non-Hodgkin's lymphoma (NHL). The incidence of NHL has increased at an alarming rate in recent years. It is now the fifth most common cancer in the U.S., and worldwide incidence is also increasing rapidly (Weisenburger 1994; Parker et al., 1996). Several translocations that correlate with various lymphoma subsets involve the IGH gene located on chromosome 14, at band q32 (14q32). Specific examples of such translocations include the t(8;14)(q24;q32) associated with Burkitt's Lymphoma (BL), the t(11;14)(q13;q32) in Mantle Cell Lymphoma (MCL), and t(14;18)(q32;q21) associated with follicular B-cell lymphoma (FL).

The t(8;14)(q24;q32) translocation was the first recurring chromosomal translocation shown to be associated with lymphomas (Zech et al., 1976). Further studies established this translocation as the hallmark of Burkitt's lymphoma (BL) because 100% of the cases show this translocation; in addition, it also has been reported in about 15% of other high grade B-cell lymphomas. (Offit et al., 1991; 1992; Gaidano et al., 1993).

MCL originates from the mantle zone B-cells. It is seen in 5-10% of NHL in adults (Weisenburger, 1992; Raffeld, et al., 1991; Banks, et al., 1992). The t(11;14)(q13;q32) is a consistent cytogenetic abnormality in 70% to 90% of MCL's (Tsujimoto et al., 1984; Williams et al., 1991; Coignet et al., 1996). The t(14;18)(q32;q21) translocation characterizes approximately 60% of B-cell NHL. It is seen in 85% of the FL and 25% of diffuse aggressive large cell lymphomas (DLCL).

The physiologic consequence of each of these translocations is deregulation of expression of a gene located at the breakpoint of the chromosome band rearranging with 14q32. This deregulation is brought about by replacement of the gene's regulatory signals by those of the IGH gene, which are consistently expressed in B cells. Thus, MYC, BCL-1, and BCL-2 are the target deregulated genes in BL, MCL, and FL, respectively, associated translocations (Chaganti, et al., 2000). In addition to these common or well-known translocations, more than a dozen other less frequent, but equally important, translocations have been identified (Chaganti, et al., 2000). Because breakpoints of the translocations occur in circumscribed regions of chromosomal DNA, their detection can be of value in diagnosis and post therapy follow-up of these neoplasms.

Methods for the Detection of Chromosomal Rearrangements. Several approaches to detecting chromosomal rearrangements have been developed. These include karyotype band analysis, Southern blot analysis, and analysis by quantitative polymerase chain reaction (PCR) or reverse-transcription PCR (RT-PCR). Of these various methods, karyotype analysis by conventional banding is the most accurate method currently in use.

Karyotyping involves culturing tumor cells from bone marrow aspirate, lymph node, or other tissue biopsies. The methodology involves accumulating metaphase cells by treatment with colcemid and fixation on glass slides according to established preparative procedures. Slides containing adequate numbers of cells in metaphase-prometaphase stage are "banded" by a number of techniques, G-banding being the most widely utilized, and observed under a microscope. The dark and pale bands along the length of the chromosome are consistent and reproducible (banding pattern). Consequently, they serve as landmarks that are the basis for chromosome identification, as well as assignment of breakpoints at the sites of rearrangement. It is precise as long as dividing cells are available. The drawbacks of this method include that it requires dividing cells, which is labor intensive and time consuming, and the method does not detect small deletions important in evaluating both the disease and potential treatments. The current rate of successful cytogenetic analysis of newly diagnosed cases ranges from 60% to 80% for hematological malignancies and <40% for solid tumors. This percentage falls dramatically in post-treatment bone marrow/blood samples, making cytogenetics a less useful tool for patient follow-up. Fifty percent of follow-up specimens do not yield results due to the extreme hypocellularity of marrow samples and poor proliferation in vitro.

Southern Blot analysis involves isolating DNA from a tumor sample and subjecting it to endonuclease digestion and fractionation on agarose gels using electrophoresis. The size-separated DNA fragments are then transferred to a nylon membrane and probed by hybridization with DNA sequences adjacent to the breakpoint. A novel rearranged band, in addition to the germ line band derived from the normal allele, indicate the presence of the translocation. This method requires the use of probes in the vicinity of the suspected breakpoints to detect rearrangements. Moreover, detection of rearrangements depends on clustering of the breakpoints in one of the rearranging chromosomes within a small region, which can be detected by one or few restriction enzyme digests. Detection of translocations, which have multiple breakpoints, requires multiple probes and multiple enzyme digests of DNA, which is cost inefficient. As a consequence, Southern blotting is not readily applicable for detecting all breakpoints in a number of disease-associated translocations [e.g., t(8;14)(q24;q32), t(11;14)(q13;q32) and t(14;18)(q32; q21)]. Finally, Southern blotting does not possess the sensitivity required to detect translocations in heterogenous samples, as the method requires a sample comprised of at least 5-10% tumor cells carrying the chromosomal rearrangement.

The polymerase chain reaction (PCR) relies on amplification of a PCR product from the translocation junction using primers containing sequences near the vicinity of the breakpoint derived from both chromosomes involved in the translocation. PCR amplification will occur only from tumor cells, whereas an amplification product will not be generated from the DNA of normal cells in which the primer templates remain on separate chromosomes. Genomic PCR will successfully amplify only if the breakpoints in the two chromosomes involved in the translocation in different tumors are distributed within a distance of 1 to 2 KB, which is the limit of conventional PCR amplification.

Reverse transcription PCR (RT-PCR) is used to identify fusion RNA and can also be employed in cases with widely scattered breakpoints. As with conventional PCR, successful amplification depends on consistent breakpoints within the same intronic regions of the two genes. In the RT-PCR method, the primers are selected from the sequences of the exons near the breakpoints from each of the two genes involved in the translocation. Although both DNA and RT-PCR methods are sensitive enough to amplify DNA, they are difficult to quantify and do not provide information on disease in terms of proportion of cells in a given biopsy, which is the desired measure. In addition, necrotic cells or free DNA can lead to biologically questionable positive results.

Both versions of the PCR analysis are difficult to quantitate and prone to false positive results from amplification of DNA sequences in dead tumor cells or in free DNA from lysed cells still present in the specimen. Moreover, PCR techniques are not readily applicable to detecting many disease-associated translocations because of the dispersed nature of the breakpoints found in these arrangements, with the dispersement of breakpoints necessitating multiple PCR reactions. These methods also have a limited utility because they are not applicable to many rearrangements involving deletions that are frequently associated with poor prognosis, such as those associated with the BCR/ABL regions on der (9) (Sinclair et al., 1999) and on der(22) (Palanisamy, unpublished data) which occur in cases of CML.

Fluorescence in situ Hybridization (FISH) is another tool for detecting chromosomal rearrangements. The term "in situ hybridization" generally refers to hybridization of a nucleic acid probe to a nucleic acid target that is part of a cytological or histological preparation. Typically, FISH methods involve the following steps: (a) fixing the tissue or other biological material under investigation to a support (e.g., glass slide or wall of a micro titer well), (b) treatment of the tissue or material to increase accessibility of probe DNA to target DNA, (c) contacting the tissue or material containing the target DNA with probes to form specific hybridization complexes, (d) post hybridization washes of the complexes to selectively remove probes that are not specifically hybridized to the target, and (e) detection of probes that have formed hybridization complexes with target DNA molecules. An advantage of FISH is that one can analyze individual cells, which eliminates the need to utilize cycling cells. Such methods are described in a number of sources, including: Gall and Pardue, (1981) Methods of Enzymology 21:470-480; Henderson, (1982) International Review of Cytology, 76:1-46; and Angerer, et al., (1985) in Genetic Engineering: Principles and Methods (Setlow and Hollaender, Eds.) vol. 7, pp. 43-65, Plenum Press, New York.

One of the problems with interphase FISH analysis is signal artifacts. These arise from two sources. One is non-specific binding of labeled DNA to protein in intact fixed nuclei. This can be partly overcome by treating the nuclei with proteolytic enzymes such as proteinase K or trypsin. Recent advances in imaging technology enables one to capture images using a CCD (Charge Coupled Device) camera and processing of images using image-processing software to reduce the background fluorescence arising from non-specific hybridization. Another problem is non-specific cross hybridization of repeat sequences in the probe with those in the genome. A Cot-1 DNA suppression step can be included in the hybridization protocols to ameliorate this problem. Because nucleic acids in the Cot-I fraction are characterized by containing highly repetitive sequences (e.g., Alu sequences, α-satellite, β-satellite sequences), these nucleic acids bind to repeat sequences in the genome, thereby blocking binding of probes to such sequences (see, e.g., Benjamin Lewin, (1994) Genes V, Oxford University Press). The limitation of such approaches, however, is that such steps fail to bind all repeat sequences and fail to anneal to all the copies of any given sequence.

Application of Detection Methods to Translocations Associated with Lymphomas. The heterogeneous nature of NHL makes accurate disease diagnosis and follow-up particularly challenging. Cytological and histological methods were previously the diagnostic methods of choice. Recent advances in developing immunophenotypic markers as well as molecular methods discussed supra, such as PCR, have revealed the highly heterogeneous nature of lymphoma. It is well established that each lymphoma type is characterized by a specific immunophenotype marker as well as nonrandom chromosomal abnormalities.

NHLs are treated by a variety of chemotherapeutic regimens and/or autologous bone marrow transplantation, which require regular follow-up and monitoring for recurrence or cancer in bone marrow and blood. The gold standard currently in use for this purpose is karyotype analysis by G-banding. As indicated supra, although this method is precise, it is labor intensive; in addition, 50% of follow-up specimens do not yield results, due to extreme hypocellularity of marrow samples and poor in vitro proliferation. Due to the dispersed nature of the breakpoints in many translocations [e.g., t(8;14) (q24;q32), t(11;14)(q13;q32) and t(14;18)(q32;q21)] over a large genomic region and the requirement of multiple probes and multiple PCR reactions, Southern blotting and PCR methods are not readily applicable for detecting all breakpoints. Furthermore, Southern blotting and PCR methods are prone to sensitivity and specificity problems because, as noted above, Southern blotting requires the presence of at least 5-10% tumor cells in the sample to detect a rearrangement, and PCR is prone to generate false positive results due to amplification of DNA from dead tumor cells or lysed cells that may be present in the sample.

FACS analysis can be used to detect specific combinations of cell surface proteins that may characterize the original blast (i.e., the immature stage of cellular development before appearance of the defining characteristics of the cell) population. Using FACS analysis, abnormal populations can be detected in as few as 0.1% (10-3) of cells. PCR has emerged as the most promising approach to date for the detection of minimum residual disease (MRD; This is the lowest percentage of tumor cells, within a large population of normal cells, at which the clinical condition of the patient can be said to be in remission. Thus, this is a symptom free disease condition, despite the presence of a low percentage of tumor cells), although other methods such as pathologic examination, FACS, PCR and cytogenetics are also utilized to estimate MRD. While PCR offers the advantage of very high sensitivity, with a detection limit of approximately $10^{-5}$, the problems noted above concerning lack of quantitation and generation of spurious results during the amplification process means that the technique is not particularly attractive for estimating MRD.

Hence, all currently available rearrangement detection methods have various shortcomings. Consequently, new methods are needed to successfully monitor the presence of tumor cells to enable evaluation of treatment options and prediction of recurrence.

SUMMARY

A variety of methods and probes are provided herein for use in the detection of chromosomal rearrangements, including methods utilizing fluorescent in situ hybridization (FISH) methods. By utilizing various techniques that are disclosed herein either singularly or in combination, the methods and probes enhance the sensitivity and the specificity of rearrangement detection relative to other conventional approaches.

Certain methods involve the preparation of probes that are free of repeat sequences and which are selected to hybridize to regions that flank potential breakpoints involved in the translocation of interest. Such methods typically involve a series of steps which include: (a) preparing a first collection of fragments that hybridize to regions flanking potential break points of a first chromosome involved in the chromosomal translocation; (b) preparing a second collection of fragments that hybridize to regions flanking potential break points of a second chromosome involved in the chromosomal translocation; (c) forming a first population of clones, each clone containing a fragment from the first collection linked to a vector; (d) forming a second population of clones, each clone containing a fragment from the second collection linked to a vector; (e) hybridizing fragments from the first population of clones with a sequence to allow elimination of clones containing fragments hybridizing to the repeat sequence; (f) hybridizing fragments from the second population of clones with a sequence to allow elimination of clones containing fragments hybridizing to the repeat sequence; (g) preparing probes from the clones in the first population whose vectors are linked to fragments that do not hybridize to the repeat sequence; and (h) preparing probes from the clones in the second population whose vectors are linked to fragments that do not hybridize to the repeat sequence.

Probes obtained according to the foregoing approach exhibit increased selectivity because the probes are repeat free and thus selectively hybridize with sequences of regions involved in actual translocations rather than simply a region containing a repeat region. The probes are typically labeled to facilitate detection. Such probes can be utilized to detect translocations in both interphase and metaphase cells. The probes can also be utilized to detect chromosomal rearrangements in diverse sample types, including but not limited to, chromosomal preparations from lymph node cells, bone marrow cells, blood cells and various tumor cells, including solid tumor cells. Probes can be specifically generated to essentially any rearrangement according to this method, including those rearrangements listed in Table 1 and Table 2 infra.

Certain methods of detecting translocations which are provided herein utilize a signal segregating approach. In such an approach, the probes used to detect the translocation are selected to hybridize to regions flanking all the known breakpoint regions associated with a translocation. Thus, in sharp contrast to conventional methods, these probes do no span the breakpoints involved in a translocation.

One such method involves providing a first and second set of differentially labeled nucleic acid probes, each set comprising a proximal probe and a distal probe, the first set of probes hybridizing to the first chromosome and bearing a first label, the second set of probes hybridizing to the second chromosome and bearing a second label. The first and second set of probes is then contacted with a chromosomal preparation. If the translocation has occurred between a first and second chromosome within the preparation, a proximal probe and a distal probe from different probe sets hybridize to each of the derivative chromosomes formed by the translocation, such that first and second label appear on each of the derivative chromosomes. If, however, the translocation has not occurred between a first and second chromosome in the preparation, the probes of the first probe set bind to the first chromosome and the probes of the second probe set bind to the second chromosome, such that only one label appears on the first and second chromosome of the preparation. At least one chromosome in the preparation that is hybridized to labeled probe is detected, wherein the presence of the first and second label on the at least one chromosome is an indication that the translocation has occurred, and the presence of only the first or the second label on the at least one chromosome is an indication that the translocation has not occurred.

Another method generally involves providing first and second sets of nucleic acid probes labeled with first and second labels where these sets of probes will hybridize to a first and a second chromosome respectively, the first and second chromosomes being susceptible to undergoing a reciprocal translocation with each other. The first and second probe sets each comprise at least one proximal and at least one distal probe, where at least one proximal probe hybridizes to a segment of chromosomal DNA that lies entirely on the centromeric side of all known break points associated with the translocation, and at least one distal probe hybridizing to a segment of chromosomal DNA that lies entirely on the telomeric side of all known break points associated with the translocation. The two sets of probes are then contacted to a chromosomal preparation, which may contain untranslocated forms of the first and second chromosomes, and/or one or more translocated forms of the first and second chromosomes. By detecting a pattern of hybridization where the first and second sets of probes have bound to the chromosomal preparation, the presence of a translocated and untranslocated forms of the first and second chromosomes in the chromosomal preparation can be determined.

In some methods the known break points in the first chromosome occur in a first gene and the known breakpoints in the second chromosome occur within a second gene, and the first and second probe sets hybridize to segments outside the first and second genes. Thus, certain methods involve, providing a first and a second nucleic acid probe that are differentially labeled, the first probe hybridizing to the first chromosome at a region located outside a first gene that includes all known breakpoints for the translocation and bearing a first label, the second probe hybridizing to the second chromosome at a region located outside a second gene that includes all known breakpoints for the translocation and bearing a second label. The first and second probes are then contacted with a chromosomal preparation. If the preparation contains a derivative chromosome formed via the translocation, the first and second probes hybridize to the derivative chromosome, such that both the first and second label appear on the derivative chromosome. If the preparation contains the first and second chromosome, the first and second probes hybridize to their respective chromosomes such that only the first label appears on the first chromosome and only the second label appears on the second chromosome. At least one chromosome in the preparation that is hybridized to the first or second probe is detected, wherein the presence of two labels on the at least one chromosome indicates that the translocation has occurred, and the presence of a single label on the at least one chromosome indicates that the translocation has not occurred.

The first and second probe sets can hybridize from around 10 kb to around 100 kb away from all known breakpoints associated with the translocation. In some methods the first and second probe sets contain a plurality of proximal probes and a plurality of distal probes hybridizing to a plurality of chromosomal segments of which the outermost segments are from about 50 kb to about 200 kb apart in the chromosomal DNA. In some of the methods, the first and second probe sets hybridize about 10 kb to about 100 kb away from all known breakpoints associated with the translocation. In some of the methods the first and second probe sets each comprises a plurality of probes hybridizing to a plurality of chromosomal segments of which the outermost segments are at least 200 kb apart in the chromosomal DNA.

In certain methods, the first and second probe sets were prepared from a first collection of fragments flanking all of the known breakpoints of the first chromosome and a second collection of fragments flanking all of the known breakpoints of the second chromosome, respectively. A first population of clones is then formed, each clone containing a fragment from the first collection linked to a vector, and a second population of clones is formed where each clone contains a fragment from the second collection linked to a vector. Fragments from the first and second populations of clones are then hybridized with a repeat sequence to allow elimination of clones containing fragments hybridizing to the repeat sequence. Probes are then prepared from the clones in the first and second populations whose vectors are linked to fragments that do not hybridize to the repeat sequence. These two probe populations are then differentially labeled with a first and a second label, respectfully. When probes constructed in the above manner are contacted to a chromosomal preparation, translocated chromosomes are determined from a pattern of hybridization comprising a colocalization of spots of first and second label. A second translocated chromosome can be identified by observing a second co-localization of spots of first and second label.

If the cell is in metaphase, which of the translocated chromosomes is a derivative of the first chromosome comprising a centromeric region from the first chromosome and a telomeric region from the second chromosome and which of the translocated chromosomes is a derivative of the second chromosome comprising a centromeric region from the second chromosome and a telomeric region from the first chromosome can be determined. If the pattern of hybridization shows a spot of first label free of second label the spot corresponds to an untranslocated form of the first chromosome. If the cell is in metaphase and the pattern of hybridization shows a spot of first label free of second label, and a comparison of this first label spot to the analogous first label spot on a homologous chromosome indicates that one spot of first label is less intense than another spot of first label, the less intense spot corresponds to a deletion in the region of the chromosome containing the hybridization site for the first label. If the cell from which the chromosomes are obtained is diploid and in metaphase and the pattern of hybridization comprises fewer than four spots of the first or second label, then the absent spot of label corresponds to a deletion of the region of chromosome recognized by the absent spot. If the cell from which the chromosomes are obtained is in metaphase, and the pattern of hybridization shows a spot of first label or second label on a third chromosome different from the first and second chromosomes, then the spot on the third chromosome corresponds to a nonreciprocal translocation between the third chromosome and either the first or second chromosome.

In still other methods first, second, third and fourth sets of nucleic acid probes labeled with first, second, third and fourth labels are prepared such that the first and second sets hybridize to a first chromosome and the third and fourth sets hybridize to a second chromosome. In such methods, the first and second chromosomes are susceptible to undergoing a reciprocal translocation with each other. The first and second probe sets respectively contain at least one proximal and at least one distal probe, the proximal probe hybridizing to a segment of DNA occurring entirely on the centromeric side of all known break points on the first chromosome associated with the translocation and the distal probe hybridizing to a segment of DNA occurring entirely on the telomeric side of all known break points on the first chromosome associated with the translocation. Similarly, the third and fourth probe sets respectively contain at least one proximal and at least one distal probe, the proximal probe hybridizing to a segment of DNA occurring entirely on the centromeric side of all known breakpoints of the second chromosome associated with the translocation, and the distal probe hybridizing to a segment of chromosomal DNA occurring entirely on the telomeric side of all known breakpoints of associated with the translocation.

Probes having the foregoing characteristics are contacted, under hybridizing conditions, to a chromosomal preparation, which may contain untranslocated forms of the first and second chromosomes, and/or one or more translocated forms of the first and second chromosomes, and/or translocated forms of the first or second chromosome with a third chromosome. The first, second, third and fourth sets of probes are bound to the chromosomal preparation. By detecting the pattern of hybridization produced, the presence of untranslocated forms of the first and second chromosomes, chromosomes resulting from translocations between the first and second chromosomes, chromosomes resulting from translocation between the first or second chromosome and a third chromosome, and/or deletions of any of these forms can be determined. In some of the methods, all the known break points in the first chromosome occur in a first gene and all the known breakpoints in the second chromosome occur within a second gene, and the first, second, third and fourth probe sets hybridize to segments outside the first and second genes. In some of the methods the first, second, third and fourth probe sets hybridize about 10 kb to about 100 kb away from all known breakpoints associated with the translocation. In some of the methods the first, second, third and fourth probe sets each comprises a plurality of probes hybridizing to a plurality of chromosomal segments of which the outermost segments are at least 200 kb apart in the chromosomal DNA.

In still other methods, the first and second probe sets are prepared from first and second collections of fragments proximal and distal to the known breakpoints of the first chromosome and third and fourth probe sets are prepared from third and fourth collections of fragments proximal and distal to the known breakpoints the second chromosome. First, second, third and fourth populations of clones are produced, each clone respectively containing a fragment from the first, second, third or fourth collection of fragments linked to a vector. Each of these clonal populations is hybridized with a repeat sequence to allow elimination of clones containing fragments hybridizing to the repeat sequence. First, second, third, and fourth sets of probes are then prepared from the respective clonal populations whose vectors are linked to fragments that do not hybridize to the repeat sequence.

Using probes constructed in the manner described above, chromosomal rearrangements can be detected from the hybridization patterns produced when the probes are hybridized to chromosomal preparations. If the pattern of hybridization shows a colocalization of spots of the first and fourth labels, then a translocated form of the first and second chromosomes comprising a centromeric region of the first chromosome and a telomeric region of the second chromosome is present in the preparation. If the pattern of hybridization shows a colocalization of spots of the second and third label, then a translocated form of the first and second chromosomes comprising a centromeric region of the second chromosome and a telomeric region of the first chromosome is present in the preparation. If the pattern of hybridization shows a colocalization of spots of first and second label, then an untranslocated form of the first chromosome is present in the preparation. If the pattern of hybridization shows a colocalization of spots of the third and fourth labels, then an untranslocated form of the second chromosome is present in the preparation. If the cell from which the chromosomal preparation is obtained is diploid and the pattern of hybridization shows fewer than two spots of any one of the first, second, third and fourth labels, then a deleted form of the first or second chromosomes is present in the preparation. If the pattern of hybridization shows two spots of any one of the first, second, third and fourth labels, and comparison of the intensity of the spots of like label shows that the intensity of one of the spots is less than the intensity of the other, then a deletion of the region corresponding to the spot of lesser intensity is present in the preparation. If the pattern of hybridization comprises a colocalization of spots of first and second label, a spot of first label free of second, third and fourth label and a spot of second label free of first, third and fourth label, then a non-reciprocal translocation resulting in transfer of a segment from the first chromosome to a third chromosome is present in the preparation.

The probe constructs of the present invention do not span translocation breakpoints, which maximizes probe hybridization to derivative chromosomes thereby maximizing the signal intensity of the associated fluorescent label. The probe constructs are also free of repeat sequences, which lowers the background presented in the methods described. The maximal signal intensity and lower background facilitates the use of automated image analysis in scoring translocation events by these methods. In some of these automated methods determining the chromosome translocation involves scanning an image of the hybridization pattern to detect presence and location of spots of the first label and the second label, followed by determining whether a distance between spots of first and second labels falls within a predetermined distance as an indication of presence of a translocated form of the first and second chromosomes. When it is determined that the distance between second spots of first and second labels falls within the predetermined distance, then a second translocated form of the first and second chromosomes is present. In such instances, the cell is classified as cancerous if and only if both first and second translocated forms of the first and second chromosomes are present.

Other methods involve detecting nuclei prior to chromosomal analysis. This is accomplished by staining the nucleus to allow its detection by an imaging device in the scanning step. In some methods this stain is DAPI stain. Defining the boundaries of nuclei by staining allows for a plurality of nuclei to be screened. Screening of the stained nuclei allows for the detection of clustered and damaged nuclei which can be ignored in the analysis. Single, undamaged, stained nuclei define a boundary within which detection of chromosomal rearrangements can be carried out. Nuclear-defined boundaries also allow multiple chromosomal preparations to be scored from a single slide thereby facilitating automated analysis.

In some methods the scanning step produces a plurality of images in different focal planes of the chromosomal preparation. Such a plurality of images can be merged to produce a 3D image of the labeled chromosomes, or alternatively, can be merged to produce a composite image of the labeled chromosomes each of which may only be in focus in a single focal plane. In other methods, the images are filtered so that the signal from only one type of fluorescent label can be detected at a time. In such methods the spatial pattern produced by each label is recorded. After the spatial pattern of all labels has been determined, the presence of chromosomal rearrangements can be scored by comparing the proximity of each label to other labels.

Methods for detecting deletions in chromosomes involved in a translocation are also provided. Certain of these methods involve providing a nucleic acid probe that bears a label and hybridizes to a first chromosome susceptible to undergoing a translocation with a second chromosome. The probe hybridizes to a segment of the first chromosome that lies entirely in a region that flanks the known break points associated with the translocation. The nucleic acid probe is contacted with a chromosomal preparation prepared from a diploid cell, which preparation may contain a chromosome resulting from deletion of at least part of the segment of the first chromosome to which the probe hybridizes. The signal intensity from the label on different chromosomes is then compared, a difference in signal intensity indicating presence of a deletion. Such methods can be utilized in combination with various other chromosomal detection methods, including the signal splitting and signal segregating methods (both S-FISH and D-FISH methods) disclosed herein.

Probe sets for use in conducting the foregoing methods are also provided. Certain probe sets for detecting a translocation between first and second chromosomes include a first and second set of nucleic acid probes labeled with first and second labels, respectively, the first probe set comprising at least one proximal probe and the second probe set comprising at least one distal probe. The at least one proximal probe has a sequence such that the proximal probe hybridizes to a segment of chromosomal DNA on the first chromosome that lies entirely on the centromeric side of all known break points associated with the translocation. Similarly, the at least one distal probe has a sequence such that it hybridizes to a segment of chromosomal DNA on the first chromosome that lies entirely on the telomeric side of all known break points associated with the translocation.

Other probes sets also include a third and fourth probe set labeled with third and fourth labels, respectively, the third probe set comprising at least one proximal probe and the fourth probe set comprising at least one distal probe. The at least one proximal probe of the third probe set has a sequence that can hybridize to a segment of chromosomal DNA on the second chromosome that lies entirely on the centromeric side of all known break points associated with the translocation. The at least one distal probe of the fourth probe set has a sequence that can hybridize to a segment of chromosomal DNA on the second chromosome that lies entirely on the telomeric side of all known break points associated with the translocation. In certain probe sets, the first and second labels are the same and the third and fourth labels are the same, but the first and second labels differ from the third and fourth labels. In other probe sets, the first, second, third and fourth label are each distinguishable from one another.

BRIEF DESCRIPTION OF THE DRAWINGS

FIGS. 2A-2D depict a two color segregating fluorescent in situ hybridization (S-FISH) approach for detecting the t(9; 22)(q34;q11) translocation. FIG. 2A depicts the normal chromosomal arrangement for chromosome 22 and chromosome 9. The interphase field is also depicted for this arrangement with an open pattern representing the signal for the BCR gene and a single hatched pattern representing the signal for the ABL gene. Cells carrying the t(9;22)(q34;q11) translocation display co-localization of the open and single hatched signals as depicted in the interphase field of FIG. 2B. FIG. 2B also schematically depicts the chromosomal arrangement after translocation of the chromosomal regions distal to the breakpoint regions of the respective chromosomes. FIG. 2C depicts a variant translocation involving chromosomes 22, 9 and 1, together with the resulting interphase pattern. Finally, FIG. 2D represents a deletion of BCR region on der(9).

FIGS. 3A-3D depict the four color fluorescence in situ hybridization (F-FISH) segregated signal approach for detecting the t(9;22)(q34;q11) translocation, with the rearrangements being analogous to those described in FIGS. 2A-2D, respectively. FIGS. 3A-3D illustrate that the probe to the centromeric side of the most centromeric breakpoint will always remain on the chromosome and the probe to the telomeric side of the most telomeric breakpoint will always segregate to the rearranged chromosome. In these figures, the single hatched probe label is always associated with chromosome 9 and the open label is always associated with chromosome 22. This aspect of the method allows for the detection of specific derivative chromosomes, and to precisely define the rearrangements undergone by the derivative chromosomes.

FIG. 5A is a schematic representation of the genomic organization of the BCL1 and the IGH genes. Vertical bars indicate approximate positions of the breakpoint regions. The CCND1 gene and the different coding regions of the IGH genes are shown as open boxes. Horizontal bars indicate approximate positions of the probes. Probes labeled 1 and 2 (represented by open bars) bind to chromosome 11 and bear a label emitting a green signal. Probes 3 and 4 (represented by single hatched bars) bind to chromosome 14 and bear a label emitting a red signal. FIG. 5B is schematic representation of the expected constellation of signals by two color S-FISH in normal and tumor interphase nuclei. Probes 3 and 4 together generate a red signal, whereas probes 1 and 2 together generate a green signal on the corresponding normal chromosomes. The close proximity of each probe results in only a single signal on interphase cells. The t(11;14)(q13; q32) positive nuclei, however, display two fusing or co-localizing green and red signals, identifying the der(14) and der (11) chromosomes. These signals arise because labeled probes are segregated between the rearranging chromosomes. FIG. 5C is schematic representation of the expected constellation of signals by four color F-FISH in normal and tumor interphase nuclei(probe 1-stippled; probe 2-open; probe 3-double hatched; and probe 4-single hatched). Each probe generates a unique signal. This approach allows for the detection and identification of specific derivative chromosomes even in interphase preparations. The alteration in signal pattern observed for the tumor preparation arises because labeled probes are segregated between the rearranging chromosomes. FIG. 5D is a schematic illustration showing the way in which the probes hybridize to the normal and derivative chromosomes in the two color S-FISH approach.

FIGS. 6A-6C illustrate a specific set of probes in a segregating signal approach that can be utilized to detect the t(14; 18)(q32;q21) translocation according to either two color S-FISH or F-FISH methods. FIG. 6A is a schematic representation of the genomic organization of BCL2 and IGH genes. Vertical lines indicate approximate positions of the breakpoint regions. The three BCL2 exons and the different coding segments of the IGH gene are shown as open boxes. Bars beneath the gene indicate the approximate positions of the probes. FIG. 6B is schematic representation of the expected pattern of signals by two color D-FISH in normal and tumor interphase nuclei. Probes 1 and 2 (represented by open bars) together generate a green signal, while probes 3 and 4 (represented by single hatched bars) together generate a red signal on the corresponding normal chromosomes. These probes are close enough on the chromosome to prevent generation of distinct individual signals. The t(14;18)(q32; q21) positive nuclei, however, display two fusion or co-localizing green and red signals identifying the der(14) and der (18) chromosomes, due to the fact that signals are segregated to the rearranging chromosomes. FIG. 6C is schematic representation of the expected pattern of signals by four color F-FISH in normal and tumor interphase nuclei. Each probe generates a unique signal (probe 1—stippled; probe 2—open; probe 3—double hatched; and probe 4—single hatched). This approach allows for the detection and identification of specific derivative chromosomes even in interphase preparations. The alteration in signal pattern observed for the tumor preparation arises because labeled probes are segregated between the rearranging chromosomes.

FIG. 7A is a schematic representation of genomic organization of the MYC and IGH genes. Vertical bars indicate approximate positions of the breakpoint regions in the MYC and IGH gene regions. The three MYC exons and the different coding segments of the IGH gene are shown as open boxes. Horizontal bars indicate the location of the probes. FIG. 7B is schematic representation of the expected constellation of signals by two color FISH in normal and tumor interphase nuclei. Probes 1 and 2 (open bars) together generate a green signal on chromosome 8, while probes 3 and 4 (single hatched bars) collectively generate a red signal on chromosome 14 on normal chromosomes. The probes on the normal chromosomes are sufficiently close to one another not to result in distinct individual signals. The t(8;14)(q24;q32) positive nuclei, however, display two fusing or co-localizing green and red signals identifying the der(8) and der(14) chromosome due to the fact that signals are segregated to the rearranging chromosomes. FIG. 7C is schematic representation of the expected pattern of signals by four color F-FISH in normal and tumor interphase nuclei. Each probe generates a unique signal (probe 1—stippled; probe 2—open; probe 3—double hatched; and probe 4—single hatched). This approach allows for the detection and identification of specific derivative chromosomes even in interphase preparations. The alteration in signal pattern observed for the tumor preparation arises because labeled probes are segregated between the rearranging chromosomes.

FIGS. 9A and 9B are schematic representations of hybridization of probes and the probe binding region of the chromosome. FIG. 9A depicts multiple probe binding, the redundancy in binding capacity contained in a single probe, and the absence of repeat sequences in the probe DNA. FIG. 9B depicts the deletion encroaching into a probe binding region. This type of deletion adversely affects probe hybridization and reduces the signal intensity of the fluorescent label associated with the probe.

FIG. 10A is a schematic representation of the genomic organization of the BCR and ABL genes. The coding regions of the gene are represented as open boxes. The approximate positions of the regions used to develop commercial probes for this translocation (based on VYSIS product catalog) are also shown as solid bars labeled green and red to represent the signal produced by the probe in the exemplary FISH assay. Vertical bars indicate the approximate position of the breakpoint regions. FIG. 10B is a schematic representation of signal localization by two color FISH in normal and tumor interphase nuclei, with a red signal (double hatched bar) for the ABL gene and a green signal (single hatched bar) for the BCR gene. Cells carrying the t(9;22)(q34;q11) translocation display co-localization of green and red signals identifying the der(22) chromosome. A third small red signal identifies the der(9) chromosome. Note that in this signal split approach the probes overlap the breakpoint region, resulting in only one of the derived chromosomes being identified by a fusion signal. FIG. 10C is a schematic illustration showing the way in which the probes hybridize to the normal and derivative chromosomes.

FIG. 11A is a schematic representation of the genomic organization of BCL2 and IGH genes. Vertical lines indicate approximate positions of the breakpoint regions. The three BCL2 exons and the different coding segments of the IGH gene are shown as open boxes. Open and single hatched bars indicate the approximate positions of the probes. FIGS. 11B-11C are images from the MetaCyte scanning and capturing process. FIG. 11B shows a DAPI counterstained nucleus. FIG. 11C is an image of a nucleus painted with two color S-FISH probes taken through an FITC filter. FIG. 11D is an image of a nucleus painted with two color S-FISH probes taken through a Rhodamine filter. FIG. 11E is an integrated image displaying both FITC and Rhodamine signals.

FIG. 12A is a schematic diagram showing the components of Metasystems image scanning platform. FIG. 12B is a flow diagram outlining the steps in the method of the Automated Bio-Imaging System.

FIGS. 13A-13C depict the use of a probe located in a region flanking the breakpoints involved in a translocation to detect detections. In the examples illustrated in these figures, the deletion detection probe is utilized in combination with probes utilized in a signal segregating approach. FIG. 13A shows the regions to which the deletion detection probe and the signal segregating probes hybridize and the hybridization pattern that is observed prior to a translocation. FIG. 13B shows the arrangement of the probes and the corresponding hybridization pattern following a translocation in which there is no deletion. FIG. 13C shows the arrangement of the probes and the corresponding hybridization pattern following a translocation which is accompanied by a deletion.

DESCRIPTION

I. Definitions

Figures 1A, 1B:
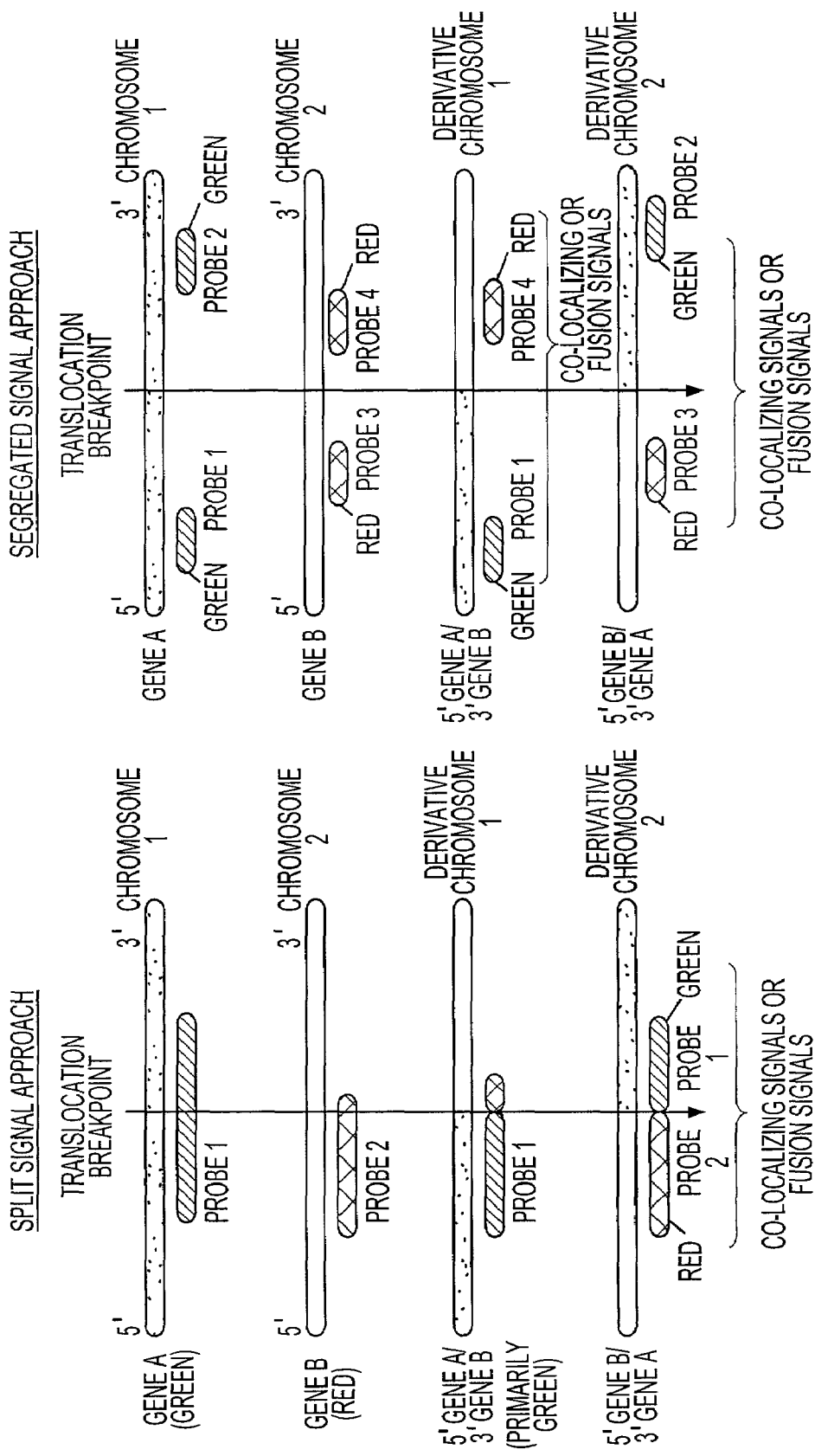
FIGS. 1A and 1B are schematic illustrations that show the differences between the "Split Signal Approach" and the "Segregating Signal Approach" in detecting chromosomal translocations.

The practice of conventional techniques in molecular biology, biochemistry, chromatin structure and analysis, computational chemistry, cell culture, recombinant DNA, bioinformatics, genomics and related fields are well-known to those of skill in the art and are discussed, for example, in the following literature references: Sambrook et al. MOLECULAR CLONING: A LABORATORY MANUAL, third edition, Cold Spring Harbor Laboratory Press, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999, each of which is incorporated by reference in its entirety.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity (e.g., an analogue of A will base pair with T).

The terms additionally encompass nucleic acids containing known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, and peptide-nucleic acids (PNAs).

A "translocation" refers to the attachment of a fragment of one chromosome to a non-homologous chromsome (the rearrangement of fragments within the same chromsome are referred to as "inversions").

A "reciprocal translocation," involves the mutual exchange of fragments between two broken chromosomes, one part of one chromsome uniting with the part of another chromosome.

A "balanced translocation" is a translocation in which there is no loss of genetic material during the translocation but all genetic material is preserved during the exchange.

A "variant" or "abnormal" translocation refers to the involvement of a third chromosome in a secondary rearrangement that follows a first reciprocal translocation.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes. The term "reciprocal chromosome" refers to one of the chromosomes engaged in a reciprocal exchange with another chromosome involving breakage and transfer of its parts. "Derivative chromosome" is the term used to refer generally to an abnormal chromosome formed as a consequence of a translocation, deletion or other chromosomal rearrangement or combination of chromosomal rearrangements. Such chromosomes are sometimes referred to simply as "der" chromosomes.

"Interphase" refers to a stage in cell division in which chromosomes are elongated and entwined with one another. In contrast, "metaphase" refers to any stage of cell division in which the chromosomes are condensed or contracted and are distinguishable from one another.

A "telomere" refers to the region of a chromosome located at the distal end of the chromosome.

The term "centromere" refers to the heterochromatic region of a eukaryotic chromosome that is the chromosomal site of attachment of the kinetochore. The centromere divides just before the replicated chromosomes separate, and acts to hold the paired chromatids together.

A "breakpoint" refers to the point or region of a chromosome at which the chromosome is cleaved during a translocation. A "breakpoint junction" refers to the region of the chromosome at which the different parts of chromosomes involved in a translocation join.

A "probe" is a nucleic acid capable of binding to a complementary target nucleic acid through one or more types of chemical bonds, usually through complementary base pairing, usually through hydrogen bond formation, resulting in a duplex structure. As described further herein the probe binds to a complementary target site in a chromosome. In translocations, the target site to which the probe binds is usually located in a segment flanking all the breakpoints. Each translocation represents specific target sites. Generally, the probe is labeled with one or more detectable labels to permit the facile detection of the probe following hybridization on its complementary target.

A "segment" or a "subsequence" when used in reference to a nucleic acid refers to a sequence of nucleotides that comprise a part of a longer sequence of nucleotides.

The term "diploid" refers to a chromosomal state where there are at least two homologues of each chromosome present, and also refers to chromosomal states where there are more than two homologues of one or more chromosomes present. In the context of FISH assays, the term "diploid" refers to a chromosomal state where there is at least one pair of homologous chromosomes, including derivative chromosomes, which are recognized by the probes used in the assay.

A "gene" refers to a region of genomic DNA that encodes a gene product. A gene product can be the direct transcriptional product of a gene (e.g., mRNA, tRNA, rRNA, antisense RNA, ribozyme, structural RNA or any other type of RNA) or a protein produced by translation of mRNA. Gene products also include RNAs, which are modified, by processes such as capping, polyadenylation, methylation, and editing, and proteins modified by, for example, methylation, acetylation, phosphorylation, ubiquitination, ADP-ribosylation, myristilation, and glycosylation.

A "detectable label" or simply "label" refers to any of a variety of different labels known in the art that can be detected by chemical, electrochemical, instrumental, or physical means, for example. Fluorescent labels are often utilized to label the probes. In some instances, other suitable labels include, but are not limited to, radioisotopes, chromophores, electron dense particles, magnetic particles, spin labels and molecules that emit chemiluminescence, enzymes, enzyme substrates, members of binding pairs (e.g., avidin/streptavidin and antigen/antibody).

A "pseudo-color" or "pseudo-label" is a representation of a detectable label, and can be any one of a variety of different representations known in the art that can be displayed or stored by physical, chemical or electronic means. Pseudocolors are often graphical elements in a pictorial representation, such as the colors displayed on a computer monitor as representations of the fluorescent labels detected in a FISH assay. Other examples of pseudo colors include graphical representations found on computer printouts, digital representations stored on a magnetic disk, pictorial representations formed through optical devices, color transformations and three-dimensional representations rendered by computational analysis. It is readily apparent from this definition that any detectable label can be represented through transformation by any pseudo-color. Such transformations allow diverse detectable labels to be represented in a common display or storage format, thereby easing interpretation and archiving of data.

"Co-localization" or "co-localizing spots" refers to detectable labels that are much closer to each other than to other detectable labels in a field of analysis. Co-localizing spots may be discrete spots, or may show some overlap forming a "Venn diagram-type" pattern, depending on the resolution of the detection device employed. A common characteristic of true co-localizing spots is that they originate from probes hybridized to the same chromosome.

"Fusion signal" or "fusion spot" refers to a composite signal produced when two different signals overlap to a degree such that they appear as a single signal. The composite signal often possesses different characteristics from either of its component signals.

A "difference" in signal intensity generally means that there is a detectable change in signal intensity that is above the detection limit of the instrument used to measure signal intensity. In some instances the difference reflects a difference in average values obtained for signal intensity. A difference is typically considered to be "statistically significant" if the probability of the observed difference occurring by chance (the p-value) is less than some predetermined level. Thus, a "statistically significant difference" can refer to a p-value that is <0.05, preferably <0.01 and most preferably <0.001.

II. Overview

Methods for enhancing the specificity and sensitivity of fluorescent in situ hybridization (FISH) assays in the detection of chromosomal rearrangements are disclosed herein. Specific methods, probes and kits for assaying selected translocations correlated with tumors are also provided. In particular, methods and probes for conducting FISH assays for the t(8;14)(q24;q32), the t(11;14)(q13;q32), the t(9;22)(q34;q11) and the t(14;18)(q32;q21) translocations are provided. The methods described herein are not limited to the examples provided but are generally applicable to other rearrangements (e.g., reciprocal translocations) that are associated with leukemia, lymphomas, or solid tumors, for instance.

Some of the FISH assay methods provided herein utilize probes that bind to chromosomal DNA at regions that flank the breakpoints. This contrasts with traditional FISH methods in which the probe(s) is (are) designed to span the breakpoint junction(s) of the chromosomes involved in a translocation. Such traditional approaches often result in a split signal in which labeled probe for each chromosome is "split" between the derivative chromosome(s) (i.e., a labeled probe that initially is hybridized to a single chromosome is split such that a portion of the labeled probe binds to each of the derivative chromosomes). As noted supra, splitting of the signal in this way reduces signal intensity and sensitivity.

By utilizing probes that hybridize to proximal or distal regions that flank the breakpoint(s) for the rearrangement of interest, the current methods generate a segregating signal rather than a split signal which greatly aids analysis. At least one of these probes is selected to bind at a region centromeric to all the known breakpoints. Such a probe is referred to herein as a "proximal breakpoint region probe" [(PBP), centromeric probe, or simply a proximal probe] and anneals to a region located between the breakpoint closest to the centromere and the centromere itself. Such probes do not segregate in a translocation involving the breakpoint(s) of interest. At least one other probe is selected to hybridize to the same chromosome as the PBP, but anneals to a region telomeric to the known breakpoints associated with the translocation of interest. Such a probe is referred to herein as a "distal breakpoint region probe" [(DBP), telomeric probe, or simply distal probe] and hybridizes to a chromosomal region located between the known breakpoint nearest the telomere and the telomere itself. In a translocation event, such probes always segregate to the reciprocal chromosome. Some of the methods provided herein utilize multiple probes chosen such that a centromeric and telomeric probe each hybridize to at least two of the chromosomes involved in a chromosomal rearrangement.

Certain methods referred to herein as S-FISH methods utilize two sets of probes, each set including at least one distal and at least one proximal probe, with each of the probe sets binding to different chromosomes that are susceptible to undergoing a rearrangement. In the S-FISH method, the probes in each set bear the same label, but probes in different sets bear different labels. Other methods referred to herein as F-FISH methods utilize the same two sets of probes, but each probe is differentially labeled, such that even probes within a set bear different labels. As described in greater detail below, F-FISH probe sets can be useful in unambiguously determining the type of rearrangement.

Still other methods extend the segregating signal concept further and utilize probes which not only flank the breakpoint(s) involved in the translocation of interest, but also that hybridize to proximal or distal regions located outside the genes involved in the translocation of interest. Such methods further differ from conventional FISH approaches in which the probes anneal to regions located within the genes involved in the translocation under investigation. These methods can be conducted in both the S-FISH and F-FISH formats.

Certain of the methods provided address a problem common to conventional FISH assays, namely the non-specific cross hybridization of repeat sequences in the probe with those in the genome. Such non-specific hybridization generates ambiguities in the analysis of FISH results, in particular the formation of false positive signals indicating the presence of a translocation when in fact a translocation has not occurred. Some of the probe design methods disclosed herein alleviate this problem. Such methods generally involve identifying sequences that flank the breakpoint(s) for a reciprocal translocation under investigation. Genomic clones carrying these sequences are then obtained, often by PCR screening of commercially available libraries using region-specific primers, and then cleaved with one or more restriction enzymes. The resulting fragments are then subcloned and the resulting subclones probed with radioactively labeled repeat DNA to determine if the subclone contains complementary repeat sequence segments. Clones without repeat sequences are then relegated to form a longer repeat free clone. Conventional methods for addressing the cross-hybridization problem do not involve such a cloning and subcloning approach and often involve pre-annealing of labeled probes with unlabeled human Cot-1 DNA; the present methods provided herein, however, are not so limited.

Some methods described herein use FISH techniques in combination with an automated scanning platform to provide a rapid, quantitative means for detecting tumor cells in patients undergoing treatment and follow-up. Automated detection and counting of FISH signals in a large number of interphase nuclei is demanding both from a physics and an optical standpoint; the signals are small, contrast is often inconsistent, and 3-D analysis is required due to the thickness of the nuclei. These problems are overcome by the methods described herein, by the use of probes from the regions flanking all the breakpoints which significantly reduces the high rate of false positive cells commonly encountered using the former FISH methods. Thus, the use of probes developed using the methods described herein facilitate analysis using automated image scanning.

In summary, the FISH methods described herein can overcome the limitations of cytogenetic and molecular genetic methods and is well-suited for detecting tumor cells, even in low frequencies, because: (1) the methods are rapid and easy to perform, (2) dividing cells are not necessary, (3) a large number of cells can be scored rapidly in a single assay, and (4) hybridization can be performed in tissues preserved in virtually any form, including paraffin embedding. In addition, careful selection of probe reagents on either side of the breakpoint region can eliminate the technical limitations of the previously discussed molecular methods.

III. FISH Detection Schemes

A. General

The FISH methods provided herein find general applicability in detecting and analyzing chromosomal rearrangements. The methods can be utilized to develop sensitive and selective probes to detect essentially any combination of rearrangements once the chromosomal sequences involved with, and flanking, the breakpoints are known. Exemplary rearrangements that occur in hematopoietic and solid cancers that can be assayed using the methods described herein include, but are not limited to, those listed in Tables 1 and Table 2 (see section III.C.8).

TABLE 1

Chromosomal translocations that serve as diagnostic and follow-up markers in cancer (Heim & Mitelman, 1995).

| Translocation | Genes involved | Disease |
|---|---|---|
| Leukemia | | |
| t(9; 22)(q32; q11) | ABL; BCR | CML |
| t(9; 22)(q34; q11) | ABL; BCR | CML |
| t(3; 21)(q26; q22) | EVI1; MDS1 | CML blast crisis, AML |
| t(6; 9)(p23; q34) | DEK; CAN | MDS, M2 basophilia |
| t(6; 11)(q27; q23) | AF6; MLL | M4, M5 |
| t(8; 21)(q22; q22) | ETO; AML1 | MDS, M2 with Auer rods |
| t(9; 11)(p21; q23) | AF9; MLL | M5 |
| t(11; 17)(q23; p13) | PLZF; RARA | M3 |
| t(11; 19)(q23; p13) | MLL; ENL | M4, M5 |
| t(15; 17)(q22; q12.21) | PML; RARA | M3 |
| t(16; 21)(p11; q23) | FUS; ERG | No specific FAB type |
| t(10; 14)(q24; q11) | HOX 11; TCRD | T cell ALL |
| t(11; 14)(p13-15; q11) | RBTN1&2; TCRD | T cell ALL |
| t(11; 19)(q23; p13) | MLL; ENL (LTG19, MLLT1) | ALL |
| Lymphoma | | |
| t(14; 18)(q32; q21) | BCL2; IGH | Follicular lymphoma |
| t(11; 14)(q13; q32) | BCL1; IGH | B-CLL |
| t(8; 14)(q24; q32) | IGH; MYC | Burkitt's lymphoma |
| t(2; 8)(p12; q24) | IGK; MYC | Burkitt's lymphoma |
| t(8; 22)(q24; q11) | IGL; MYC | Burkitt's lymphoma |
| t(9; 14)(p13; q32) | PAX5; IGH | Plasmacytoid lymphoma |
| t(3; 14)(q27; q32) | BCL6; IGH | Large cell lymphoma |
| t(14; 15)(q32; q11-13) | IGH; BCL8 | Large cell lymphoma |
| Solid tumor | | |
| t(1; 13)(p36; q14) | PAX7; FKHR | Rhabdomyosarcoma |
| t(2; 13)(q35 ;q14) | PAX3; FKHR | Rhabdomyosarcoma |
| t(11; 22)(p13 ;q12) | WT1/EWS | Ewing sarcoma |
| t(21; 22)(q24; q12) | ERG/EWS | Ewing sarcoma |
| t(X; 18)(p11; p11) | SSX/SYT | Synovial sarcoma |

Currently, diagnosis and post-treatment follow-up of these particular cancers and other cancers associated with chromosomal rearrangements are typically performed by either karyotype analysis, Southern blotting, polymerase chain reaction (PCR) or fluorescence in situ hybridization (FISH). As noted supra, each of these methods has limitations of specificity and/or sensitivity, thus creating the need for another precise, reliable and easy method to detect tumor cells, especially in post-treatment set up.

B. FISH Utilizing Split Signal Approach

One approach for conducting a FISH assay utilizes what is referred to herein as a split signal approach. FIG. 1A illustrates the use of this method for detecting a translocation event. The method generally utilizes two differentially labeled probes (e.g., probes bearing a green or a red fluorophore) that each hybridize to a segment of a gene (e.g., gene A or gene B in FIG. 1A) on one of the chromosomes that is involved in a translocation (e.g., chromosome 1 or 2 in FIG. 1A). In this approach, the segment to which the probes bind spans the breakpoint (in FIG. 1A, the binding segments are represented by the dashed and cross-hatched bars). Once a rearrangement occurs to form derivative chromosome(s), the labeled probes can potentially bind to the derivative chromosomes since each rearranged chromosome typically includes a part of the segment complementary to each probe. Thus, while prior to the translocation each probe hybridized to a single chromosome, after the translocation any given labeled probe becomes "split" between the two derivative chromosomes. Consequently, a derivative chromosome can be detected by the formation of a fusion signal, i.e., a combined signal resulting from different signals for the different labels borne by the probes. Whether one or two fusion signals are generated depends upon the location at which the probes hybridize in relation to the breakpoints. If a probe spans the breakpoint a significant distance on either side of the breakpoint (e.g., probe 1 in FIG. 1A), then the probe can likely bind to both derivative chromosomes. If, however, a probe only extends a short distance across a breakpoint (e.g., probe 2 in FIG. 1A), the probe may only be able to bind to one of the derivative chromosomes.

Figures 10A, 10B:
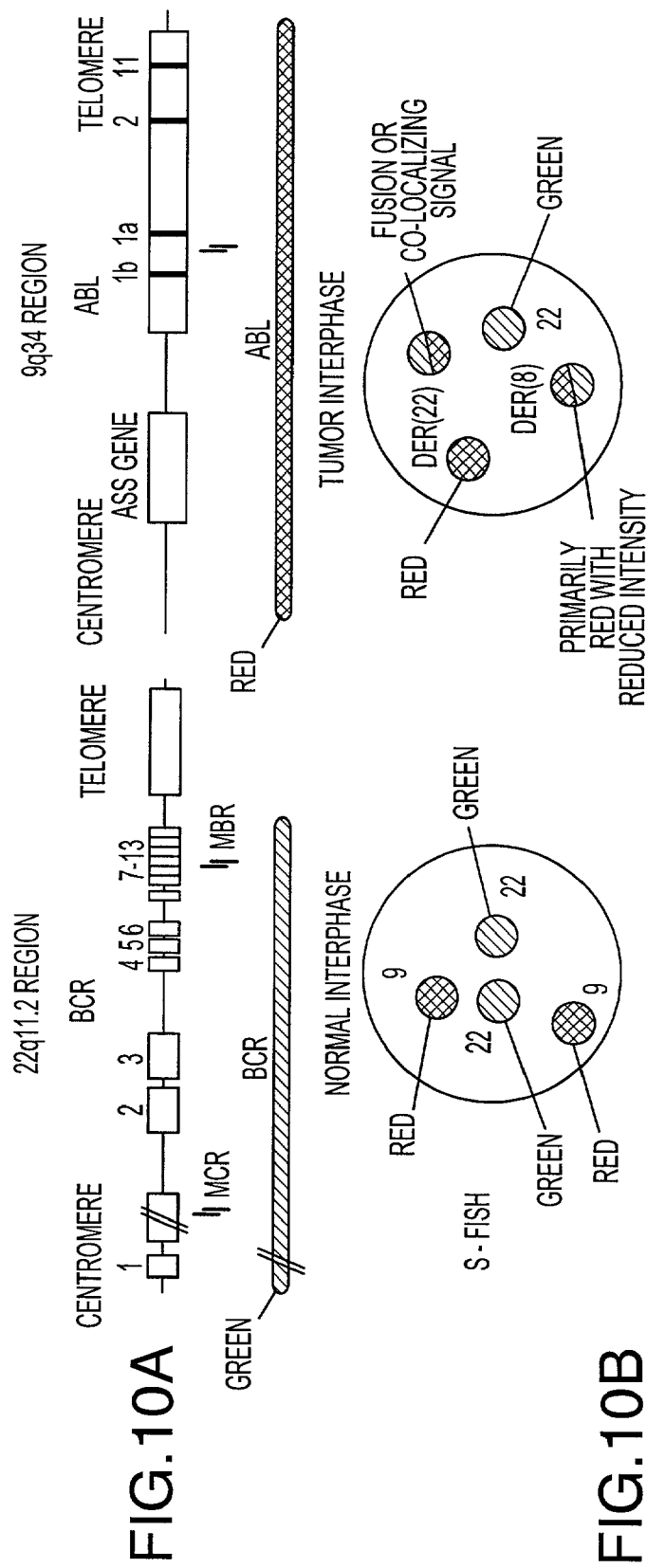
FIGS. 10A-10C depict the split signal approach for detecting the t(9;22)(q34;q11) translocation.
Figure 10C:
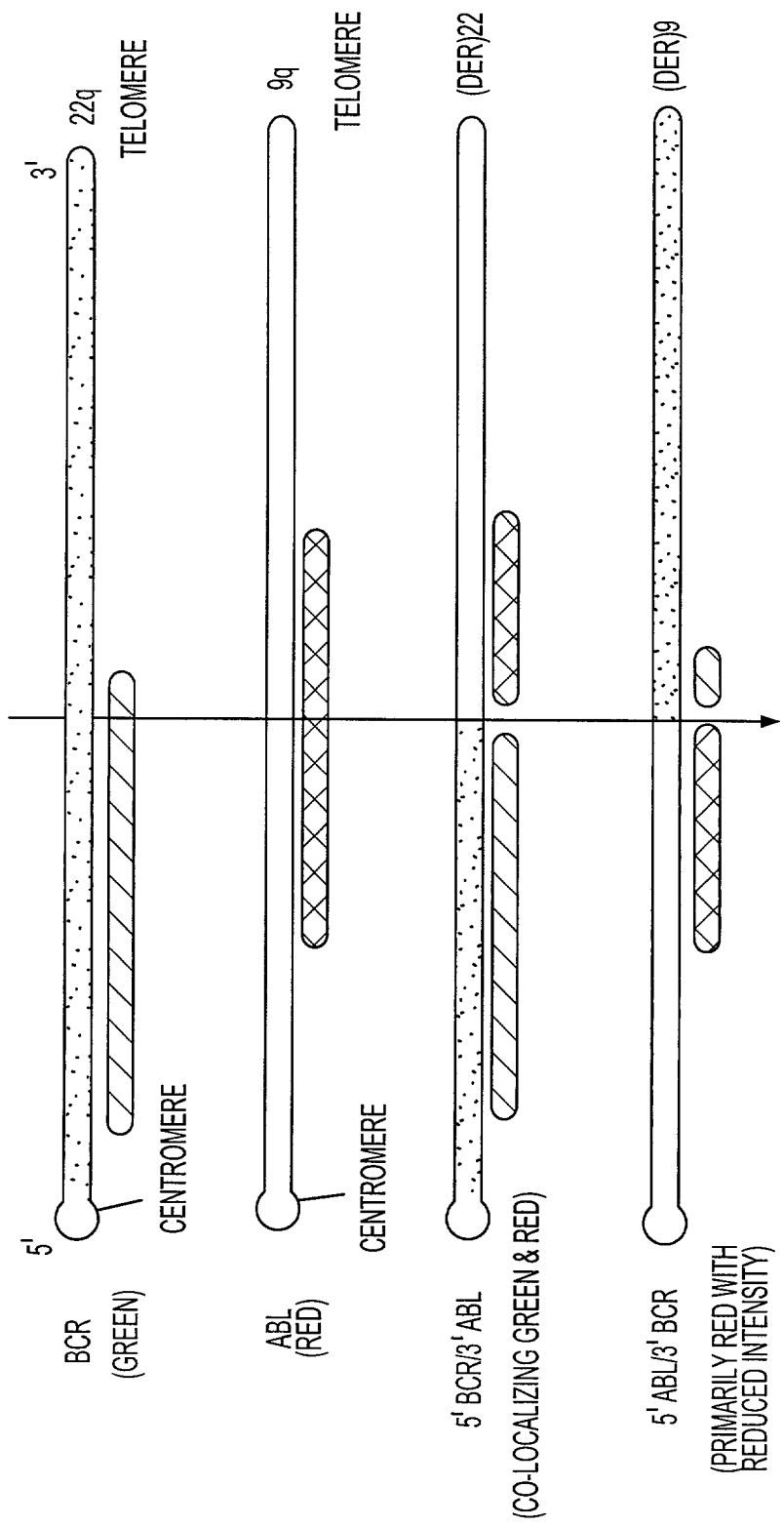

This approach is illustrated more specifically in FIGS. 10A and 10B, which is based on the BCR/ABL fusion in the t(9;22)(q34;q11) translocation in chronic myelogenous leukemia (CML), for which commercial probes are available (VYSIS). The only commercially available probe for leukemia translocations, i.e., t(9;22)(q34;q11) in CML, were developed based on the split signal principle. FIG. 10A provides a schematic illustration of the genomic arrangement of the BCR and ABL genes. The coding regions of the gene are represented as open boxes. Also shown, as single hatched bars (e.g., green) and double hatched bars (e.g., red), are approximate positions of the regions used in the development of commercial probes for this translocation by VYSIS (based on VYSIS product catalog). The vertical bars indicate the approximate position of the breakpoint regions. FIG. 10B is schematic representation of the localization of the labeled probes by two color FISH in normal and tumor interphase nuclei; FIG. 10C illustrates how the probes hybridize to the chromosomes both before and after the translocation. Cells carrying the t(9;22)(q32;q11) translocation display co-localization of the two signals (green and red), thus identifying the der(22) chromosome. A third small red signal identifies the der(9) chromosome. In this split signal approach, only one fusion signal identifies only one of the derived chromosomes.

There are three major disadvantages with this method. The first relates to sensitivity. False positive signals may be generated in normal cells by random co-apposition of normal chromosomal signals. This is especially critical in probe systems that detect fusion signals from only one of the two derived chromosomes. The second disadvantage is that it is difficult to generate probes spanning all the breakpoints that are sometimes spread over several kilobases of intronic DNA. Ideally, probe systems should detect both reciprocal partners of the translocation without the need to include the breakpoint region. Finally, difficulties arise in identifying variant forms of translocations. For example, some translocations are accompanied by deletions within the genetic regions involved in the translocation. Such deletions can effect both the sensitivity and precision of the method by weakening, or completely removing, probe binding sites. Other rearrangements are accompanied by secondary translocations involving additional chromosomes. In some split-signal arrangements, such secondary translocations can go entirely undetected.

C. FISH Utilizing Signal Segregation Approach

1. General

FISH methods can also be performed using a segregating signal approach that differs from the foregoing split signal approach. Such methods utilize first and second sets of probes hybridizing to first and second chromosomes that are susceptible to undergoing a reciprocal translocation with one another. Each set of probes comprises at least one proximal probe and at least one distal probe. The proximal probe or probes occurs on the centromeric side of all known breakpoints associated with the translocation and are referred to as proximal break point probes (PBPs), or simply proximal probes. The distal probe or probes occurs on the telomeric side of all known breakpoints associated with the translocation and are referred to as distal break point probes (DBPs), or simply distal probes. Neither the proximal nor the distal probes hybridize to any region within any of the known breakpoints. In some methods, the proximal and distal probes hybridize to regions that are at least 10 kb, 50 kb, 100 kb or 200 kb away from the outermost known centromeric break point and the known outermost telomeric break point, respectively. In some methods, all known break points associated with a translocation on a particular chromosome are within a gene, and the proximal and distal probes are both located outside the gene. In some methods, the proximal and distal probes hybridize to regions of chromosomal DNA extending no further than 1 Mb from the outermost known centromeric and telomeric breakpoints associated with the translocation. The region, however, can be a shorter distance from the breakpoint(s) (e.g., up to about 800 kb, 600 kb, 400 kb, 200 kb, 100 kb, 50 kb, 25 kb 10 kb, 5 kb, 1 kb and 0.5 kb) and longer distances (e.g., up to about 1.2 Mb, 1.4 Mb, 1.6 Mb, 1.8 Mb, 2 Mb and 4 Mb), including any integer within the foregoing ranges, provided the region is sufficiently long to allow for specific hybridization between the probe and region.

The length of proximal and distal probes and corresponding regions of chromosomal DNA bound by the probes can vary. In some methods, the length of chromosomal DNA bound by distal or proximal probe(s) varies from 10 kb to 1000 kb. In other methods, the length of chromosomal DNA bound by distal or proximal probe(s) varies from 100 kb to 300 kb and in still other methods is about 200 kb. In certain methods, the distal probe or probes do not hybridize to a single contiguous region of chromosomal DNA but rather to several regions interspersed by repeat sequences for which corresponding probes sequences have been removed. In such methods, the region of chromosomal DNA bound by such probes is that between the outermost regions of chromosomal DNA to which the probes hybridize (i.e., including intervening repeating segments not bound by the probe). In general, signal strength increases within increasing length of probes, and lengths of the order of 200 kb are typically utilized.

FIGS. 1A and 1B illustrate the differences between the segregating signal and split signal approaches. As can be seen, in the segregating signal approach (FIG. 1B), the probe binding site is not "split" due to spanning a breakpoint involved in the translocation; consequently, there is no loss of signal strength and sensitivity is increased.

By analyzing the hybridization pattern, the original first and second chromosomes, and derivative chromosomal forms that result from reciprocal translocation between the two chromosomes, can be identified and distinguished. The methods can also identify nonreciprocal translocations of DNA from the first or second chromosome to a third chromosome. The methods can also identify deletions occurring concurrent with translocations. The methods can be performed on both interphase and metaphase cells, although in some methods there are differences in the information that can be extracted from the resulting hybridization pattern.

Hybridization patterns can have any a number of arrangements of labels indicating the presence of various chromosomes and translocation events. In the two color S-FISH strategy, translocation between the first and second chromosomes is indicated by a co-localization of spots of first and second label. Co-localization means that spots of the labels appear significantly closer to each other than to other spots of label. Often (but not necessarily) co-localizing spots of label intersect like two circles of a Venn diagram. In such cases, the co-localization is manifested by first label, second label and first and second label superimposed. If colocalizing spots do not intersect, then colocalization is indicated by the proximity of two spots relative to that of other spots in the same hybridization pattern. For metaphase chromosomes, colocalization can be seen from the two spots being located on the same chromosome. If the translocation between first and second chromosomes is reciprocal, then two derivative chromosomes result, and this is indicated by two separate colocalizations of first and second label in the hybridization pattern. If the cell is in metaphase, one can distinguish between the two derivative chromosomes based on the locations of colocalizing label. Thus, if a colocalization of first and second labels has first label in the centromeric region of a derivative chromosome and second label in the telomeric region, then one knows that the derivative chromosome is formed from the first chromosome, with the centromeric region originating from the first chromosome and the telomeric region from the second chromosome. Conversely, if a colocalization of first and second labels has second label in the centromeric region of a derivative chromosome and first label in the telomeric region, then one knows that the derivative chromosome formed from the second chromosome, with the centromeric region originating from the second chromosome and the telomeric region from the first chromosome region. The ability of the present methods to detect simultaneously both derivative chromosomes significantly reduces or eliminates the probability of scoring false positive cells, a considerable problem plaguing current detection methods.

The hybridization pattern can include a spot of first label without second label and a spot of second label without first label in addition to colocalizing spots of first and second label. Such spots signify the presence of untranslocated forms of the first and second chromosomes. Occasionally, a pattern can be obtained having four colocalizing spots of first and second label and no spots of first label with spots of second label. Such a pattern signifies that both pairs of chromosomes in a diploid cell have undergone a reciprocal translocation resulting in four derivative chromosomes.

If the cells being analyzed are in metaphase, the hybridization pattern can sometimes include a spot of either first or second label on a third chromosome different from either the first or second chromosome. Such a pattern signifies that the first or second chromosome has undergone a nonreciprocal translocation with a third chromosome, whereby the third chromosome has acquired a telomeric segment from the first or second chromosome. Such nonreciprocal translocations can occur in combination with, or separate from, reciprocal translocations. Therefore, a spot of first or second label on a third chromosome can be observed in combination with either colocalization of first and second label on reciprocally translocated chromosomes, or with first label without second label on the first chromosome and second label without first label on the second chromosome.

The pattern of hybridization can also indicate the presence of deletions. Deletions are typically associated with poor prognosis, thus making unambiguous identification of such changes highly important. Through F-FISH analysis, deletions are readily detectable through loss of a label normally present in the signal pattern. Since each label directly indicates the location of the origin of the probe generating it, the missing label directly identifies the region of deletion.

Generally, deletions of chromosomal material coincident with a translocation or translocation-like rearrangement can take one of two forms. Macro-deletions, such as those depicted in FIG. 2D and FIG. 3D, typically appear to be a consequence of an aborted translocation where chromosomal material is lost instead of exchanged, or is exchanged non-reciprocally. Such macro-deletions result in a loss of all chromosomal material distal and/or proximal to a known breakpoint involved in the translocation event.

The second type of deletion, a micro-deletion, differs from a macro-deletion in two respects. First, micro-deletions, as the name implies, are typically very much smaller in size when compared to a macro-deletion. Second, micro-deletions occur proximal (centromeric), or distal (telomeric), to known breakpoints. Micro-deletions can result from at least two possible mechanisms. In one mechanism, a nuclease acts on the unprotected chromosomal stub left without a telomeric structure following a macro-deletion or translocation event can effect a deletion. A second possible mechanism is that previously unmapped breakpoint(s) exist proximal or distal to all known breakpoints and what is characterized as a micro-deletion is actually the product of a translocation or translocation-like event involving the unmapped breakpoint.

Macro-deletions can be detected by the presence of fewer spots of label than expected. For example, if a cell is diploid and no deletions occur, with the two color S-FISH method one expects to see two spots of first label and two spots of second label. With the F-FISH method, in the absence of deletions, one expects to see two sets of two fused spots, the fused spots of the first set consisting of first and second labels and the fused spots of the second set consisting of third and fourth labels. If the hybridization pattern contains fewer spots, then one can conclude that a deletion has occurred. If the missing spot is of first label, then one can conclude that a segment from the first chromosome has been lost, and likewise if the missing spot is of the second label one can conclude that a segment of the second chromosome has been lost. If the cell is in metaphase, one can tell more precisely from the hybridization pattern which chromosome, and where within the chromosome, the loss of the segment has occurred.

Micro-deletions can be detected by comparing the intensities of different spots of label, usually of the same type. Reduced intensity of one spot relative to another of the same label indicates a deletion, and the magnitude of the reduction is related to the extent of the deletion. This correlation exists because the intensity of the signal produced by a labeled (e.g. fluorophore) probe is proportional to the degree of hybridization between the probe and its chromosomal binding site. Thus, for example, if a hybridization pattern contains colocalizing spots of first label (indicating an untranslocated form of the first chromosome) and colocalizing spots of first and second label (indicating a derivative chromosome formed by translocation between the first and second chromosomes), one can compare the intensity of the spots arising from first label or associated with the untranslocated and derivative chromosomes. Determining that the intensity of first label on the derivative chromosome is less than the intensity of label associated with the untranslocated chromosome indicates that the derivative chromosome has undergone a deletion.

2. Exemplary S-FISH Analyses

The foregoing principles are illustrated by FIGS. 2A-D utilizing two color S-FISH methods. FIG. 2A shows regions from human chromosomes 22 and 9 containing the BCR and ABL genes that contain breakpoints for a reciprocal translocation. The probes shown in this figure lie outside of all known breakpoints and in fact outside the BCR and ABL genes. FIG. 2A shows the hybridization pattern in a normal cell. There are four spots, two spots displaying each label, the spots occurring in co-localizing pairs that at least partially intersect. FIG. 2B shows derivative chromosomes that result from reciprocal translocation of chromosomes 22 and 9. Der (22) contains the centromeric region from chromosome 22 and the telomeric region from chromosome 9, thus creating the BCR/ABL oncogene whose expression product disrupts normal cell growth and promotes a cancerous state. Der(9) contains the centromeric region from chromosome 9 and the telomeric region from chromosome 22. The hybridization pattern resulting from this translocation contains two colocalizing spots of first label (open bar) and second label (single hatched bar) (corresponding to der(22) and der(9); designated by the letter "A" in FIG. 2B) and two spots (one of first label and one of second label) corresponding to untranslocated chromosomes 22 and 9.

FIG. 2C shows an example of derivative chromosomes resulting from a variant, nonreciprocal translocation involving chromosomes 1, 9, and 22. Chromosome der(22) consists of the regions of chromosome 22 centromeric to the translocation breakpoint, and a telomeric region from chromosome 9. Chromosome der(1) consists of chromosome 1, to which the telomeric region of chromosome 22 has been attached. Chromosome der(9) is chromosome 9 which has undergone a nonreciprocal translocation of the region telomeric to the translocation breakpoint located in the ABL gene. The effect of this nonreciprocal translocation on chromosome 9, is a deletion of the telomeric region of the chromosome arm. When the variant nonreciprocal translocation of FIG. 2C occurs in diploid cells, at least three spots of each label can be observed in the hybridization pattern. The pattern contains two spots, one each of first and second label, corresponding to untranslocated chromosomes 22 and 9. Colocalizing spots of first and second labels, noted by the letter "A" in FIG. 2C, correspond to the derivative chromosome 22, der(22). The single spot of second label (single hatched pattern), noted by the letter "B" in FIG. 2C, corresponds to der(9); the single spot of first label (open pattern), noted by the "C" in FIG. 2C, corresponds to der(1). One interpretation of the variant translocation result depicted in FIG. 2C is that a reciprocal translocation between chromosomes 9 and 22 was initiated, but at some point deviated from the common reciprocal exchange of telomeric regions between the two chromosomes. Chromosome 22 received the telomeric region of chromosome 9, forming der(22), but the translocation mechanism transferred the telomeric region of chromosome 22 to chromosome 1, forming der(1), instead of attaching it to the breakpoint lesion on chromosome 9.

A similar mechanism explains the macro-deletion of chromosome 9 depicted in FIG. 2D. Once again, a reciprocal translocation event was initiated by cleavage of chromosome 9 at a breakpoint within the ABL gene. Instead of translocating the telomeric region of chromosome 9 to chromosome 22, chromosome 22 was left intact and the cleaved telomeric region of chromosome 9 subsequently lost, thus leaving chromosome 9 as a derivative chromosome, der(9), carrying a macro-deletion. The resulting hybridization pattern for a diploid cell possessing a chromosome with this macro-deletion is depicted in FIG. 2D. The pattern comprises spots of first label (open pattern) corresponding to the untranslocated pair of chromosome 22 homologues. There are also two discrete spots of second label (single hatched pattern) in the pattern. One second label spot corresponds to the untranslocated chromosome 9 homologue. The other second label spot is of lower intensity and corresponds to the der(9) containing the macro-deletion.

3. Exemplary F-FISH Analyses

In a variation of the above methods, distal and proximal probes of each probe set can be differentially labeled. Such methods are referred to as F-FISH methods. The differential labels of distal and proximal probes hybridizing to the first and second chromosome can be viewed as subtypes of the first and second labels described above. However, for simplicity, the proximal and distal probes hybridizing to the first chromosome are now referred to as having first and second labels, respectively, and the proximal and distal probes hybridizing to the second chromosome are referred to as having third and fourth labels, respectively. Methods employing four differentially labeled probe sets are sometimes referred to as F-FISH in distinction from methods employing two differentially labeled probe sets that are sometimes referred to as being S-FISH.

F-FISH probes are particularly useful for analyzing interphase cells. Because each section of the chromosome bearing the breakpoint of interest hybridizes to a different label, one can characterize an interphase chromosomal preparation simply by analyzing the proximity of the probe signals emitted by each label. Using the F-FISH strategy, one can distinguish both the nature of the rearrangement and precisely which chromosomes participated in the rearrangement event, even in interphase systems.

Hybridization patterns can give any number of arrangements of labels indicating particular chromosomes and any rearrangements those chromosomes may have undergone. Untranslocated chromosomes are indicated by a colocalization of first and second label or colocalization of third and fourth label. More specifically, a colocalization of first and second label corresponds to an untranslocated first chromosome, and colocalization of third and fourth label corresponds to an untranslocated second chromosome. Co-localization is possible because the label for each probe set is unique to the probe set and PBP's are retained on the original chromosome, even after that chromosome has undergone a rearrangement.

A translocation between the first and second chromosomes is indicated by a co-localization of spots of first and fourth label or second and third label. A colocalization of first and fourth label corresponds to the first rearranged chromosome. The translocated first chromosome having an arm comprised of the centromeric region of the first chromosome and the telomeric region of the second chromosome. Correspondingly, a colocalization of second and third label corresponds to the second rearranged chromosome. The translocated second chromosome having an arm comprised of the centromeric region of the second chromosome and the telomeric region of the first chromosome.

The hybridization pattern can include isolated spots of first, second, third and fourth label in addition to co-localization of spots of first or third label with spots of fourth or second label. Isolated spots of this type indicate the presence of either a macro-deletion or a variant translocation of the telomeric region of the first or second chromosome to a third chromosome. More specifically, isolated spots of second or fourth label are indicative of variant translocations comprised of a transfer of the telomeric region beyond the breakpoint of the first or second chromosome to a third chromosome. An isolated second spot corresponds to the transfer of the telomeric region beyond the breakpoint of the first chromosome, to a third chromosome. Similarly, an isolated fourth spot corresponds to the transfer of the telomeric region beyond the breakpoint of the second chromosome, to a third chromosome.

Isolated spots of first and third label are indicative of macro-deletions of telomeric regions of the first or second chromosome. An isolated spot of first label corresponds to a first chromosome which has undergone a macro-deletion in the telomeric region beyond the translocation breakpoint. Similarly, an isolated spot of third label corresponds to a second chromosome which has undergone a macro-deletion in the telomeric region beyond the translocation breakpoint.

The F-FISH strategy also enables the detection of micro-deletions by comparing the intensities of different spots of label of the same type. Reduced intensity of one spot relative to another of the same label indicates a deletion, and the magnitude of the reduction is related to the extent of the deletion. This correlation exists because the intensity of the signal produced by a labeled fluorescent probe is proportional to the degree of hybridization between the probe and its chromosomal binding site. For example, if a hybridization pattern contains colocalizing spots of first and second label (indicating an untranslocated form of the first chromosome) and colocalizing spots of first and fourth label (indicating a derivative chromosome formed by translocation between the first and second chromosomes), one can compare the intensity of the first label spots from the untranslocated and derivative chromosomes. Determining that the spot of label on a derivative chromosome has less intensity than the same spot of label on an untranslocated chromosome indicates the derivative chromosome has undergone a deletion. The same analysis can be done by comparing isolated spots of any label type with a spot of the same label type on an untranslocated chromosome. The F-FISH strategy allows micro-deletion detection to be made for both interphase and metaphase chromosomes, although metaphase preparations are preferred because the labels are much more discrete when the chromatin is condensed.

The principles of the F-FISH strategy are illustrated schematically in FIGS. 3A-3D, which shows identical rearrangements to those depicted in FIGS. 2A-2D for the S-FISH strategy with chromosomes 9 and 22 containing the ABL and BCR genes, respectively. Both ABL and BCR contain multiple breakpoints where chromosomal rearrangements can occur. The probes shown in FIG. 3A lie outside all known breakpoints and in fact lie outside the ABL and BCR genes themselves. FIG. 3A also indicates that each probe has a unique label, which allows for independent identification of both centromeric and telomeric regions of each chromosome in both interphase and metaphase preparations. The hybridization pattern in a normal diploid cell using the F-FISH strategy is shown in FIG. 3A. There are two spots of each label in the normal pattern, with first and second labels (open and stippled pattern, respectively) colocalizing and corresponding to chromosome 22, and third and fourth labels (single hatched and double hatched patterns, respectively) colocalizing and corresponding to chromosome 9.

FIG. 3B shows derivative chromosomes that result from reciprocal translocation of chromosomes 22 and 9. Der(22) contains the centromeric region from chromosome 22 and the telomeric region from chromosome 9 and der(9) contains the centromeric region from chromosome 9 and the telomeric region from chromosome 22. The resulting hybridization pattern contains co-localizing spots of first and second label corresponding to the untranslocated chromosome 22, and colocalizing spots of third and fourth label corresponding to untranslocated chromosome 9. The hybridization pattern also contains two additional sets of colocalized labels corresponding to derivative chromosomes formed by the reciprocal translocation event. One of these sets is comprised of first and fourth label (open and double hatched pattern, respectively) and corresponds to a derivative chromosome 22, der(22). The second of these sets of co-localizing spots is comprised of second and third labels (stippled and single hatched pattern, respectively) and corresponds to a derivative chromosome 9, der(9).

FIG. 3C shows three derivative chromosomes formed by a variant, non-reciprocal translocation. The hybridization pattern resulting from this rearrangement in diploid cells contains five sets of spots. One set of spots consists of first and second labels colocalizing and corresponding to chromosome 22. A second set of spots consists of third and fourth labels colocalizing and corresponding to chromosome 9. A third set of spots consists of a first label (open pattern) colocalizing with a fourth label (double hatched pattern) and corresponds to a derivative chromosome, der(22), comprised of the centromeric region of chromosome 22 and the telomeric region of chromosome 9. The pattern also contains two isolated spots of label. One of these isolated spots is of third label (single hatched pattern). In these examples, third label is associated with the PBP of chromosome 9, and will always correspond to chromosome 9 or a derivative of that chromosome. Whenever a spot of third label is observed isolated from all other spots, it corresponds to a der(9) where the chromosome 9 has undergone a macro-deletion in the chromatin telomeric to a known breakpoint. Because the second and fourth labels always migrate with the chromatin telomeric to a known breakpoint, an isolated spot of either of these labels indicates that chromatin telomeric to a known breakpoint has been translocated to a third chromosome. Thus, the isolated spot of second label (stippled pattern) contained in the hybridization pattern corresponds to a variant translocation to a third chromosome, in this case chromosome 1.

FIG. 3D illustrates the hybridization pattern produced by a macrodeletion of one of the labeled chromosomes. When such a deletion occurs in diploid cells, four sets of spots are produced. Two sets of spots consist of first and second labels (open and stippled pattern, respectively) colocalizing and corresponding to the homologous pair of chromosome 22. A third set of spots consists of third and fourth labels (single hatched and double hatched pattern, respectively) colocalizing and corresponding to chromosome 9. The hybridization pattern contains a fourth isolated spot of third label (single hatched pattern) corresponding to a der(9), which consists of chromosome 9 from which a section of the telomeric region has been lost as the result of a macrodeletion. Using this strategy, micro- and macro-deletions encroaching into the binding regions of first and third probes can be detected. Micro-deletions are detected by the presence of labels emitting at a reduced intensity, while the complete absence of label from the pattern is indicative of a macro-deletion.

4. The t(11;14)(q13;q32) Translocation in Mantle Cell Lymphoma

Figure 5A:
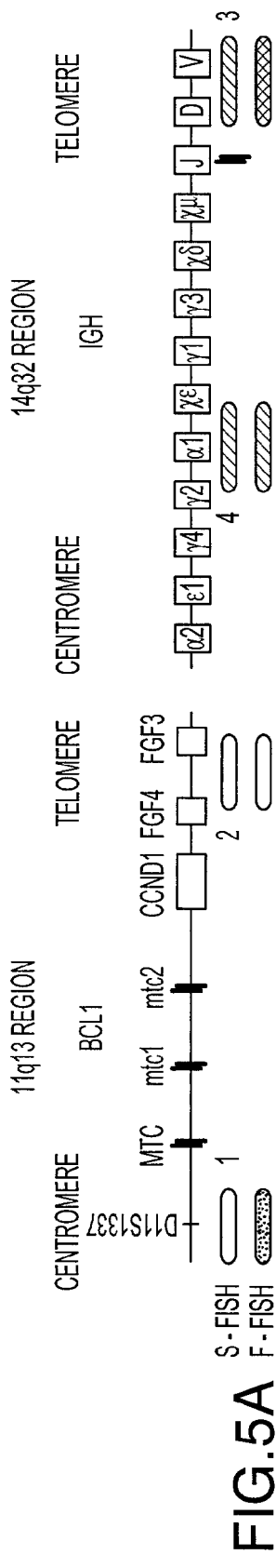
FIGS. 5A-5D depict the segregating signal approach for detecting the t(11;14)(q13;q32) translocation by S-FISH and F-FISH methods.
Figure 5B:
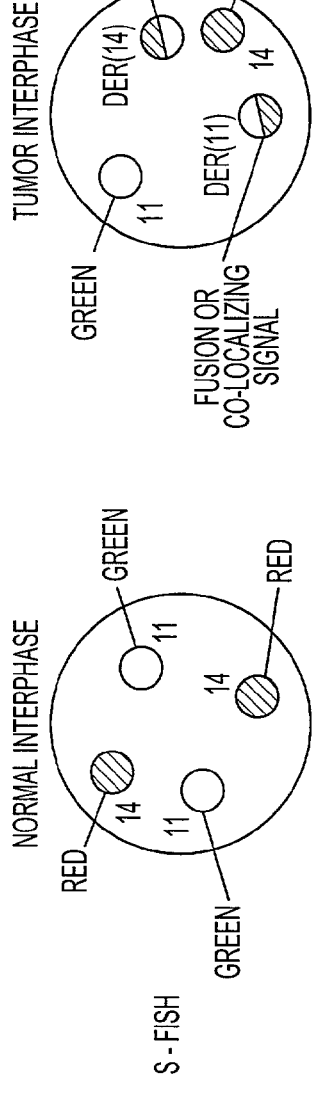

The section describes in more detail how the S-FISH and F-FISH segregated signal approaches can be utilized for the detection of the t(11;14)(q13;q32) translocation associated with Mantle Cell Lymphomas. With reference now to FIGS. 5A and 5B, the t(11;14)(q13;q32) translocation results from breakpoints that occur within the JH region of the immunoglobulin heavy chain gene (IGH) on chromosome 14q32; whereas, in more than 80% of the cases, the breakpoints on chromosome 11q are clustered in a region known as the major translocation cluster (MTC), (Rimokh et al., 1990; Williams et al., 1993; Vandenberghe et al., 1992). Additional breakpoints have been identified in the region between MTC and the BCL1 gene known as minor translocation cluster regions 1 & 2 (mTC1 & mTC2). This region spans about 120 kb upstream of the CCND1 gene at 11q13 (de Boer et al., 1993; Rimokh et al., 1993) (see FIG. 5A). In FIG. 5A, vertical bars indicate the approximate positions of the breakpoint region. The CCND1 gene and the different coding regions of the IGH genes are shown as open boxes.

With the two color S-FISH segregating signal approach provided herein, the labeled probes utilized to detect the t(11;14)(q13;q32) translocation are selected to hybridize with segments of chromosomes 11 and 14 that flank the breakpoints. In this particular detection scheme, two probes are utilized for each chromosome, with probes that hybridize to the same chromosome bearing the same label and probes that bind to the different chromosomes bearing different labels. In the example shown in FIG. 5A, the probes are differentially labeled (e.g., probes for chromosome 11 are labeled with a green fluorophore), while probes for chromosome 14 are labeled with a red fluorophore). By utilizing probes that are differentially labeled for the different chromosomes, the probes can be readily distinguished from one another.

Representative probes that bind to segments flanking the breakpoints are shown in FIG. 5A with open horizontal bars indicating binding locations for chromosome 11 probes (i.e., probes 1 and 2 labeled, for example, with a green fluorophore) and single hatched bars indicating the binding locations for chromosome 14 probes (i.e., probes 3 and 4 labeled, for example, with a red fluorophore). Of course, other probes for each chromosome can be utilized, provided the probes hybridize to segments that flank the known breakpoint regions. Thus, the probes derived from the most proximal region of the translocation breaks will not segregate for all rearrangements within the BCL1 and IGH genes. In contrast, the probes derived from the region distal to the proximal breakpoints do segregate to the reciprocal chromosomes.

Figure 5C:
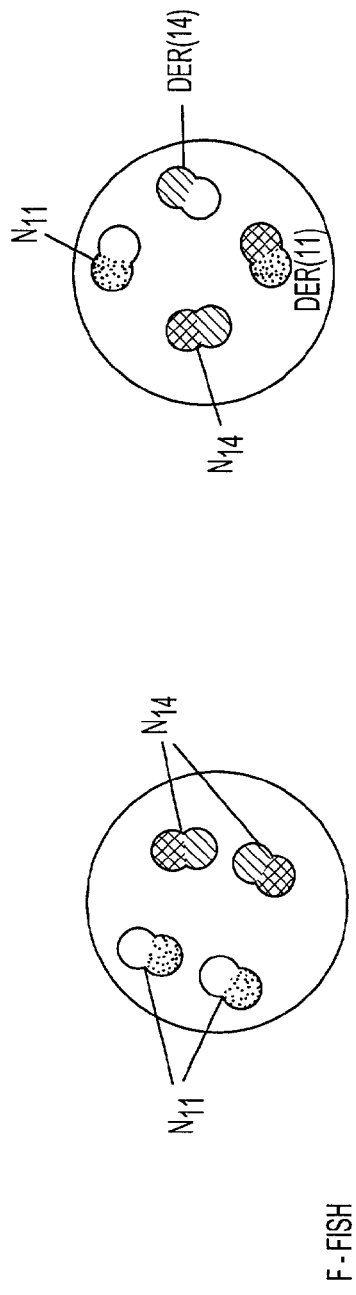
Figure 5D:
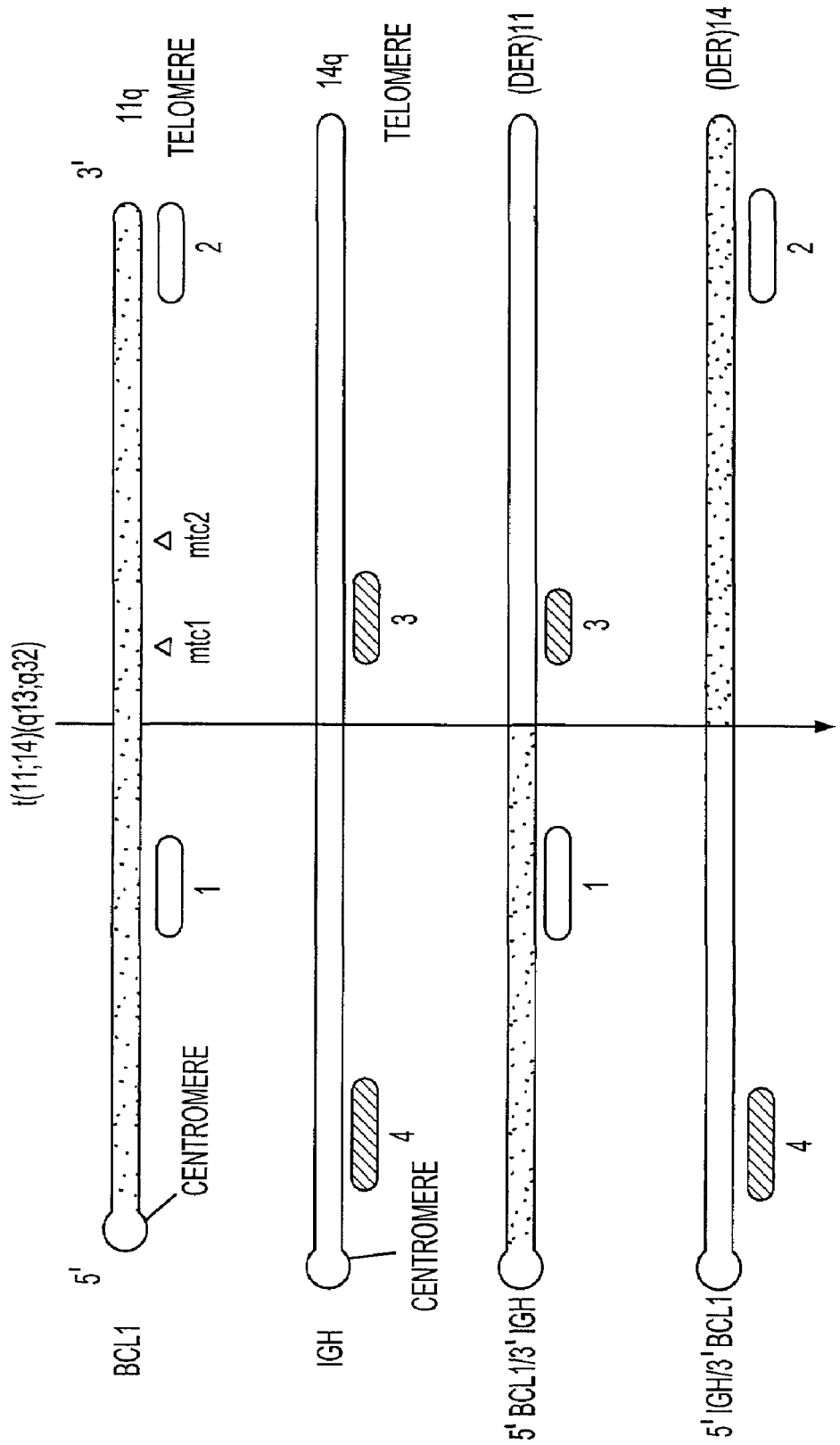

FIGS. 5B and 5D illustrate how the probes become segregated between the two chromosomes as a consequence of the rearrangement that occurs with cleavage occurring at the MTC. In normal interphase chromosomes that have not undergone rearrangement, probes 3 and 4 (single hatched pattern) generate a red signal, whereas probes 1 and 2 (open pattern) generate a green signal when the two color S-FISH strategy is used. The close proximity of the two probes on each chromosome results in one signal rather than two distinct signals on each chromosome. However, t(11;14)(q13; q32) positive nuclei (i.e., nuclei in which the translocation has occurred) display two fusing or co-localizing green and red signals (combination of open and single hatched pattern); these co-localizing signals identify the der(14) and der(11) chromosomes and arise because the distal probes on each chromosome segregate to the reciprocal chromosome as a consequence of the translocation.

FIG. 5C illustrates identical events as described above for the S-FISH strategy, with the exception that the interphase patterns are generated by a four color F-FISH strategy. As described in detail supra, in the F-FISH strategy each set of probes carries a unique label allowing specific chromosomal regions from particular chromosomes to be identified in both interphase and metaphase preparations. In FIG. 5C, first label is represented by the stippled pattern and binds to chromosome 11 centromeric to all known breakpoints in the BCL1 gene. The open pattern represents the second label which binds to chromosome 11 in a position telomeric to all known breakpoints in the BCL1 gene. The double hatched pattern represents the third label which binds to chromosome 14 telomeric to the known breakpoint region found in the IGH gene; the single hatched pattern represents fourth label which binds chromosome 14 centromeric to the known breakpoint region found in the IGH gene.

The normal interphase hybridization pattern shows four sets of colocalized spots representing the untranslocated forms of chromosomes 11 and 14. The sets of spots consisting of colocalized first and second label correspond to chromosome 11 and the sets of spots consisting of colocalized third and fourth label correspond to chromosome 14. The tumor interphase hybridization pattern for the t(11;14)(q13;q32) translocated chromosomes represents a classic reciprocal translocation pattern using the F-FISH strategy. As in the normal interphase hybridization pattern, the tumor interphase hybridization pattern consists of four sets of colocalizing spots of label. Two of these sets of spots represent the normal homologues for chromosomes 11 and 14 (colocalized spots of first and second label correspond to chromosome 11, and colocalized spots of third and fourth label correspond to chromosome 14). The remaining two sets of spots correspond to derivative chromosomes formed from a reciprocal translocation between chromosomes 11 and 14. Specifically, the colocalized first and third label spots (stippled and double hatched patterns) correspond to a der(11) chromosome consisting of the centromeric region of chromosome 11 and the telomeric region of chromosome 14. Colocalized spots of second and fourth label (open and single hatched patterns) correspond to the a der(14) chromosome consisting of the centromeric region of chromosome 14 and the telomeric region of chromosome 11.

As is illustrated by a comparison of the tumor interphase fields of FIG. 5B and FIG. 5C, the two color S-FISH strategy only allows a determination of the presence of two rearranged chromosomes from the presence of the two identical co-localizing signals. Using the S-FISH strategy, it is impossible to determine the identity of particular rearranged chromosomes. The F-FISH strategy improves upon this S-FISH result by allowing identification of specific derivative chromosomes based upon the unique probe labels recognizing each breakpoint-flanking region of each rearranged chromosome, even when the chromosomes are in interphase.

Aspects of the segregating signal approach as utilized to detect the t(11;14)(q13;q32) translocation are described in greater detail in Example 3.

5. The t(14;18)(q32;q21) Translocation in Follicular Lymphoma

This section describes the application of the signal segregating approach to the t(14;18)(q32;q21) translocation utilizing S-FISH and F-FISH. This section also describes an analysis in which the probes for at least one chromosome not only flank the breakpoint(s) involved in the translocation, but also bind outside the gene involved in the translocation, which is contrary to conventional FISH methods. This particular translocation is strongly correlated with two types of B-cell non-Hodgkin's lymphoma (NHL), FL and DLBCL, and results in the juxtaposition of the BCL2 gene on chromosome 18q21 with the immunoglobulin heavy chain (IGH) gene on chromosome 14q32.

FIG. 6A presents a schematic representation of the genomic organization of BCL2 and IGH genes. The vertical lines of FIG. 6A indicate the approximate positions of the breakpoint regions. Open boxes represent the three BCL2 exons and the different coding segments of the IGH gene. The horizontal bars indicate the approximate position of the chromosome to which the probes anneal. As shown in FIG. 6A, probes 1 and 2 anneal to regions outside the BCL2 gene. Probes 3 and 4 bind to the indicated regions of the IGH gene.

FIG. 6B is a schematic representation of the expected pattern of signals by two color FISH (i.e., S-FISH) in normal and tumor interphase nuclei. For chromosomes that have not undergone translocation, probes 1 and 2 (open pattern) together generate a green signal, while probes 3 and 4 (single hatched pattern) generate a red signal. Once hybridized to the chromosome, the probes are sufficiently close to one another such that distinct signals are not observed. Nuclei in which the t(14;18)(q32;q21) translocation has occurred, however, display two fusion or co-localizing green and red signals (combination of open and single hatched pattern) identifying the der(14) and der(18) chromosomes, due to the fact that labels are segregated to the rearranging chromosomes.

FIG. 6C illustrates identical events as described above for the two color S-FISH strategy, with the exception that the interphase patterns are generated by a four color F-FISH strategy. In FIG. 6C, a first label is represented by the stippled pattern and binds to chromosome 18 centromeric to the BCL2 gene and flanking all known breakpoints associated with the BCL2 gene. The open pattern represents the second label which binds to chromosome 18 in a position telomeric to the BCL2 gene and all known breakpoints associated with the BCL2 gene. The double hatched pattern represents third label which binds to chromosome 14 telomeric to the known breakpoint region found in the IGH gene. The single hatched pattern represents fourth label which binds chromosome 14 centromeric to the known breakpoint region found in the IGH gene.

The normal interphase hybridization pattern shows four sets of colocalized spots representing the untranslocated forms of chromosomes 18 and 14. The sets of spots consisting of colocalized first and second label correspond to chromosome 18 and the sets of spots consisting of colocalized third and fourth label correspond to chromosome 14. The tumor interphase hybridization pattern for the t(14;18)(q32;q21) translocated chromosomes represents a classic reciprocal translocation pattern using the F-FISH strategy. As in the normal interphase hybridization pattern, the tumor interphase hybridization pattern consists of four sets of colocalizing spots of label. Two of these sets of spots represent the normal homologues for chromosomes 18 and 14 (colocalized spots of first and second label correspond to chromosome 18 and colocalized spots of third and fourth label correspond to chromosome 14). The remaining two sets of spots correspond to derivative chromosomes formed from a reciprocal translocation between chromosomes 18 and 14. Specifically, the colocalized first and third label spots (combined stippled and double hatched pattern) correspond to a der(18) chromosome consisting of the centromeric region of chromosome 18 and the telomeric region of chromosome 14. Colocalized spots of second and fourth label (combined open and single hatched pattern) correspond to a der(14) chromosome consisting of the centromeric region of chromosome 14 and the telomeric region of chromosome 18.

The probe locations utilized for chromosome 18 illustrate that the signal segregating approach is effective when the probes are located a considerable distance from the translocation breakpoints, in this case outside the gene (BCL2) containing the translocation breakpoints.

6. Automated Detection of the t(14:18)(q32;q21) Translocation in Follicular Lymphoma Although currently there are several methods available for diagnosing chromosomal translocations, they are not sensitive enough to detect the translocation in a small number of tumor cells present in a large pool of normal cells. Thus, they are not efficient for monitoring patients undergoing chemotherapy or bone marrow transplantation. For example, routine PCR analysis fails to recognize almost 25% of breakpoints in MBR and MCR breakpoint analysis (Vaandrager et al., 2000). Long distance PCR analysis may be used with greater sensitivity, but it is technically more demanding and is not suitable for routine analysis in clinical laboratory settings. In addition PCR, and other current methods for detecting chromosomal rearrangements, do not readily lend themselves to automated scoring of cells.

By facilitating automatic scoring of tumor cells containing chromosomal rearrangements, the methods described herein reduce both the cost and the time required to make diagnostic determinations for a variety of disease states involving such rearrangements. The probes described herein flank all known translocation breakpoints and are not disturbed by translocation events. This property ensures maximum probe hybridization and signal intensity. By rendering the probes repeat sequence-free (see infra), probe binding specificity is also significantly enhanced, lowering background signals frequently plaguing FISH techniques. These features markedly enhance signal selectivity, virtually eliminating false positive cells, which is critical for accurate diagnosis using automated techniques.

Figure 11A:
FIGS. 11A-11E illustrate aspects of automated detection of the t(14;18)(q32;q21) translocation associated with follicular lymphoma.
Figure 11B:
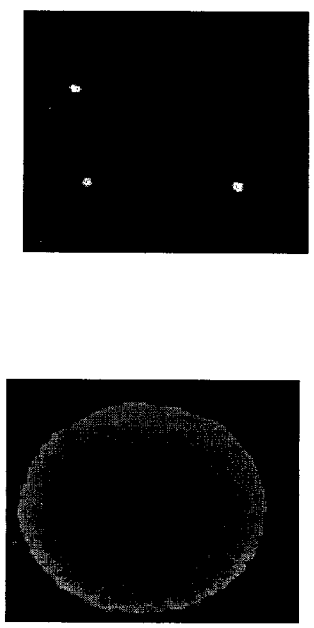

The typical automated process for detection of translocations incorporating the methods described herein includes several steps. These steps are depicted in FIGS. 11A-E for a cell that has undergone the t(14;18)(q32;q21) translocation. FIG. 11A is a schematic representation of the genomic organization of BCL2 and IGH genes located on chromosomes 18 and 14, respectively. Vertical lines indicate approximate positions of the breakpoint regions. The three BCL2 exons and the different coding segments of the IGH gene are shown as open boxes. Open and single hatched bars indicate the approximate positions of the two color S-FISH probes used in this example. Note that the probes flank all known breakpoints on their respective chromosomes. Probes 1 and 2 (open bars) bind to chromosome 18 in centromeric and telomeric flanking regions, respectively. Probes 3 and 4 (single hatched bars) bind to chromosome 14 in telomeric and centromeric flanking regions, respectively. Cells to be screened by the method are counterstained with DAPI (allowing nuclei to be identified) and contacted with fluorescently-labeled probes constructed as described herein. The scanning equipment first establishes the focal plane of the nuclei at a reduced number of grid positions within the scan area. The slide is then scanned, preferably at a high frame rate. Within each camera field of view, the counterstain image (DAPI) is captured and analyzed to identify nuclei. Such a DAPI-stained nucleus is depicted in FIG. 11B. Shape features of DAPI-stained nuclei are then available, allowing for rejection of clusters and damaged nuclei.

Figure 11C:
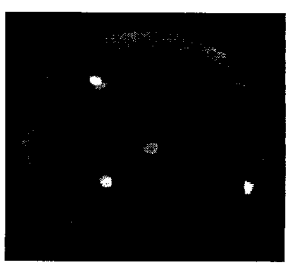
Figure 11D:
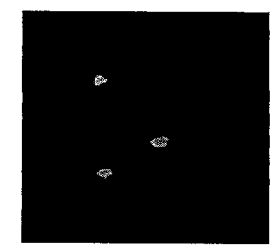
Figure 11E:
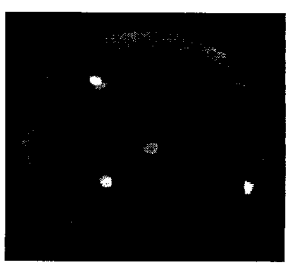

If one or several nuclei are found within the camera field of view, the fluorescent probes binding to the chromosomes is detected as illustrated in FIG. 11E. In FIG. 11E, four sets of spots can be seen. The single discrete dark grey spot in the center of the field corresponds to an untranslocated chromosome 14. The single discrete light grey spot in the bottom left of the field corresponds to an untranslocated chromosome 18. Two sets of spots consist of fused light and dark grey spots (uppermost sets of spots in FIG. 1E). These two sets of fused spots correspond to derivative chromosomes that have undergone a translocation with one another.

Once such a nucleus is detected, a fluorescence filter (e.g., FITC, Rhodamine) is changed to acquire individual S-FISH probe signals. FIG. 11C illustrates the use of a filter that removes the probe signals generated by probes 3 and 4, allowing for the detection of the signals generated by probes 1 and 2. Only three light grey spots can be seen. These three light grey spots correspond to the untranslocated copy of chromosome 18 (binding both probes 1 and 2), and the signals generated by probes 1 and 2 on the respective translocated derivative chromosomes. The spatial orientation of the three light grey signals in FIG. 11C is identical to that of the three light grey signals present in the unfiltered frame in FIG. 11E. Thus, by comparing the filtered image in FIG. 11C to the unfiltered image in FIG. 11E, the identity of the chromosomes corresponding to each spot can be ascertained.

Similarly, FIG. 11D illustrates the use of a filter that removes the probe signals generated by probes 1 and 2, allowing for the detection of the signals generated by probes 3 and 4. Only three dark grey spots can be seen. These three dark grey spots correspond to the untranslocated copy of chromosome 14 (binding both probes 3 and 4), and the signals generated by probes 3 and 4 on the respective translocated derivative chromosomes. The spatial orientation of the three dark grey signals in FIG. 11D is identical to that of the three dark grey signals present in the unfiltered frame in FIG. 11E. Thus, by comparing the filtered image in FIG. 11D to the unfiltered image in FIG. 11E, the identity of the chromosomes corresponding to each spot can be ascertained.

Determination of suitable, labeled nuclei can be made manually or automatically by the scanning equipment. Once detected by either method, a series of images from different focal planes is captured and combined to an extended focus image (z-stack). If probes labeled with different fluorochromes are hybridized, an extended focus image is generated for each fluorochrome/filter combination. For strong signals, a lower magnification can be used to increase scanning speed.

The scanning equipment can also analyze the image texture within the nuclei in each color plane and extract numerous features. For example, it identifies spots based on their relative intensity, size, form factor and proximity. The user can select criteria and parameters the spots have to meet to be counted, including minimum or maximum size, minimum contrast, intensity, etc. In addition, spot co-localization in different color planes is analyzed to detect fusion signals. The system can be trained to make such identifications with a set of selected cells that reflect the morphometric characteristics of the current specimen. The minimum and maximum distance between red and green signals will be the determining criteria for the fusion or colocalizing signals in the automated platform.

An image for each analyzed cell is stored and displayed in a gallery for user verification at the end of the analysis. Any of the measured features can be presented as histograms and scatter plots and the like, which can be used to select subpopulations for display, analysis or relocation, immediately after the scan, after having performed additional assays, or even in real time during the scanning procedure.

Aspects of the automated two color S-FISH approach, as utilized to detect the t(14;18)(q32;q21) translocation, are described in greater detail in Example 6.

7. Detection of the t(8;14)(q24;q32) Translocation Associated with Burkitt's Lymphoma This section describes the use of S-FISH and F-FISH to detect the t(8;14)(q24;32) translocation. As noted supra, this particular translocation has been found in 100% of Burkitt's lymphoma (BL) cases and in about 15% of other high grade B-cell lymphomas (Offit et al., 1991; 1992; Gaidano et al., 1993). The variant forms of this t(8;14) translocation, t(8;22)(q24;q11) and t(2;8)(p11;q24), have been identified in acute lymphoblastic leukemia, (Rabbitts 1994). The molecular consequence of the t(8;14)(q24;q32) translocation is the deregulation of the MYC proto-oncogene; this deregulation results from the replacement of the regulatory region of MYC gene by the heavy chain constant region of IGH. However, the locations of the breakpoints within the MYC gene are variable. Further details regarding the t(8;14)(q24;q32) translocation associated with Burkitt's Lymphoma (BL) are presented infra in Example 4.

Figure 7A:
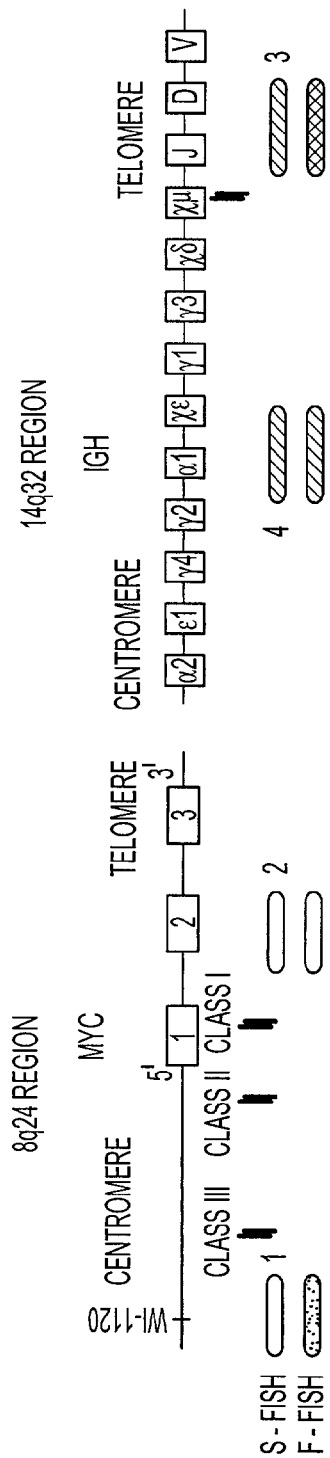
FIGS. 7A-7C show examples of a specific sets of probes that can be utilized in a signal segregating approach to detect the t(8;14)(q24;q32) translocation.

FIG. 7A is a schematic representation of the genomic organization of MYC and IGH genes. The vertical lines of FIG. 7A indicate the approximate positions of the breakpoint regions. Open boxes represent the three MYC exons and the different coding segments of the IGH gene. The horizontal bars indicate the approximate position of the chromosome to which the probes anneal. As shown in FIG. 7A, probe 1 anneals to a region outside the MYC gene and probe 2 anneals to a region within the MYC gene spanning exon 2, but telomeric to all the known breakpoints. Probes 3 and 4 bind to the indicated regions of the IGH gene.

Figure 7B:
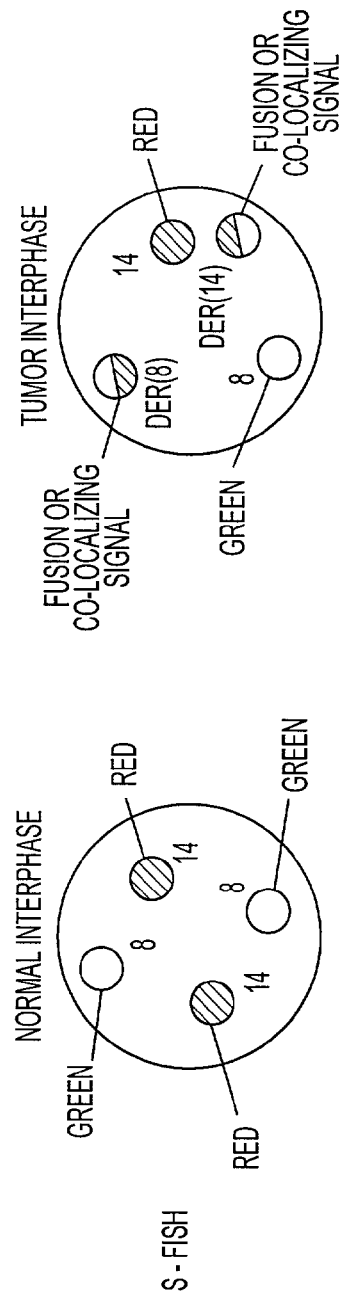

FIG. 7B is a schematic representation of the expected pattern of signals by two color FISH (S-FISH) in normal and tumor interphase nuclei. For chromosomes that have not undergone translocation, probes 1 and 2 (open bars) together generate a green signal, while probes 3 and 4 (single hatched bars) generate a red signal. Once hybridized to the chromosome, the probes are sufficiently close to one another such that distinct signals are not observed. Nuclei in which the t(8;14)(q24;q32) translation has occurred, however, display two fusion or co-localizing green and red signals identifying the der(8) and der(14) chromosomes (combined open and single hatched pattern), due to the fact that signals are segregated to the rearranging chromosomes.

Figure 7C:
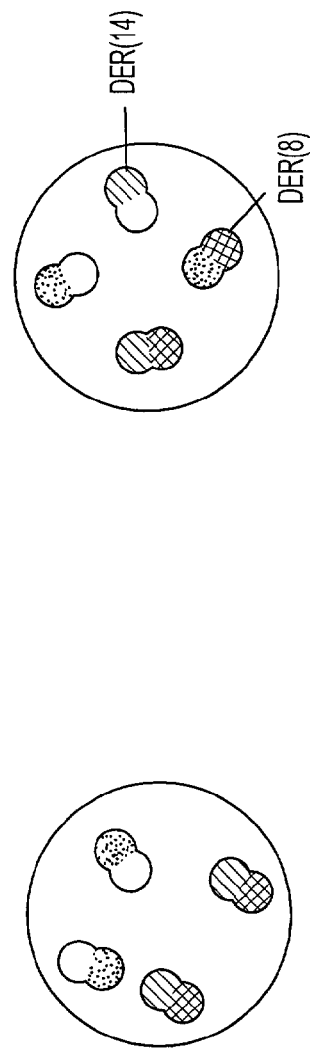

FIG. 7C illustrates identical events as described above for the two color S-FISH strategy, with the exception that the interphase patterns are generated by a four color F-FISH strategy. In FIG. 7C, first label is represented by the stippled pattern and binds to chromosome 8 centromeric to the MYC gene and flanking all known breakpoints associated with the MYC gene. The open pattern represents the second label which binds to chromosome 8 in a position telomeric to all known breakpoints associated with the MYC gene. The double hatched pattern represents the third label which binds chromosome 14 telomeric to the known breakpoint region found in the IGH gene; the single hatched pattern represents the fourth label which binds chromosome 14 centromeric to the known breakpoint region found in the IGH gene.

The normal interphase hybridization pattern shows four sets of colocalized spots representing the untranslocated forms of chromosomes 8 and 14. The sets of spots consisting of colocalized first and second label correspond to chromosome 8 and the sets of spots consisting of colocalized third and fourth label correspond to chromosome 14. The tumor interphase hybridization pattern for the t(8;14)(q24;q32) translocated chromosomes represents a classic reciprocal translocation pattern using the F-FISH strategy. As in the normal interphase hybridization pattern, the tumor interphase hybridization pattern consists of four sets of colocalizing spots of label. Two of these sets of spots represent the normal homologues for chromosomes 8 and 14 (colocalized spots of first and second label correspond to chromosome 8, and colocalized spots of third and fourth label correspond to chromosome 14). The remaining two sets of spots correspond to derivative chromosomes formed from a reciprocal translocation between chromosomes 8 and 14. Specifically, the colocalized first and third label spots (combined stippled and double hatched pattern) correspond to a der(8) chromosome consisting of the centromeric region of chromosome 8 and the telomeric region of chromosome 14. Colocalized spots of second and fourth label (combined open and single hatched pattern) correspond to the a der(14) chromosome consisting of the centromeric region of chromosome 14 and the telomeric region of chromosome 8.

8. The t(9;22)(q34;q11) Translocation in Chronic Myeloid Leukemia

This section discusses how F-FISH can be used to detect a wide variety of rearrangements associated with the t(9;22)(q34;q11) Translocation. Cytogenetically, this translocation is the hallmark of chronic myelogenous leukemia (CML) affecting 95% of patients by the presence of a reciprocal translocation between chromosome regions 9q34 and 22q11 which results in Philadelphia chromosome (Ph) (De Klein et al., 1982; Nowell et al., 1960; Rowley 1973). The presence of Ph chromosome is also identified in 5% of children and 20% of adults with acute lymphoblastic leukemia (ALL) (Hagemeijer, 1987). At the molecular level, the translocation results in the activation of ABL oncogene on chromosome 9q34, which becomes fused to the 5' end of the BCR gene on chromosome 22q11. The different breakpoints are clustered in both BCR and ABL genes. In BCR, the majority of the breakpoints occur in the major breakpoint cluster region (M-BCR) within a region of 5.8 kb between exons 12-16 of the entire BCR gene (Heisterkamp et al., 1983; Mills et al., 1991). In a subset of CML and ALL cases, the breakpoints are further proximal to M-BCR region termed m-BCR. A third breakpoint cluster region termed μ-BCR, was identified distal to exon 19 (Pane et al., 1996). In the ABL gene, the breakpoints may occur anywhere within a region larger than 300 kb proximal to exon Ib, between exons Ib and Ia or distal to exon Ia. Regardless of the different breakpoints in ABL gene, the exon a2 is fused to the truncated BCR gene (Melo, 1996). The BCR/ABL fusion results in the production of fusion proteins of three different sizes, (p210, p190, and p230) depending upon the utilization of M-BCR, m-BCR and μ-BCR breakpoints, respectively (Faderl et al., Maurer et al., 1991).

Currently, the clinical heterogeneity of CML cases in the presentation of clinical symptoms and progression is not well understood. Recently, it was shown that a subset (9%) of CML cases and a subset of ALL cases had large deletions adjacent to the translocation breakpoints on the der(9) chromosome (Sinclair et al., 1999, Kolomietz et al., 2001) and on der(22) chromosome (Palanisamy, unpublished data). Patients with deletions had a shorter survival time and high relapse following bone marrow transplantation. Similar deletions were also found in cases of AML M4 with inv(16) and cases with MLL gene translocations. Such losses due to submicroscopic deletions are implicated in altered clinical behavior and are not detectable by conventional G-band analysis. Currently available probes do not reproducibly detect such deletions and are not thoroughly validated for such analysis (Mohr et al., 2001). The probes and methods described herein offer a highly sophisticated and sensitive means for detecting deletions on both derivative chromosomes.

Figure 4:
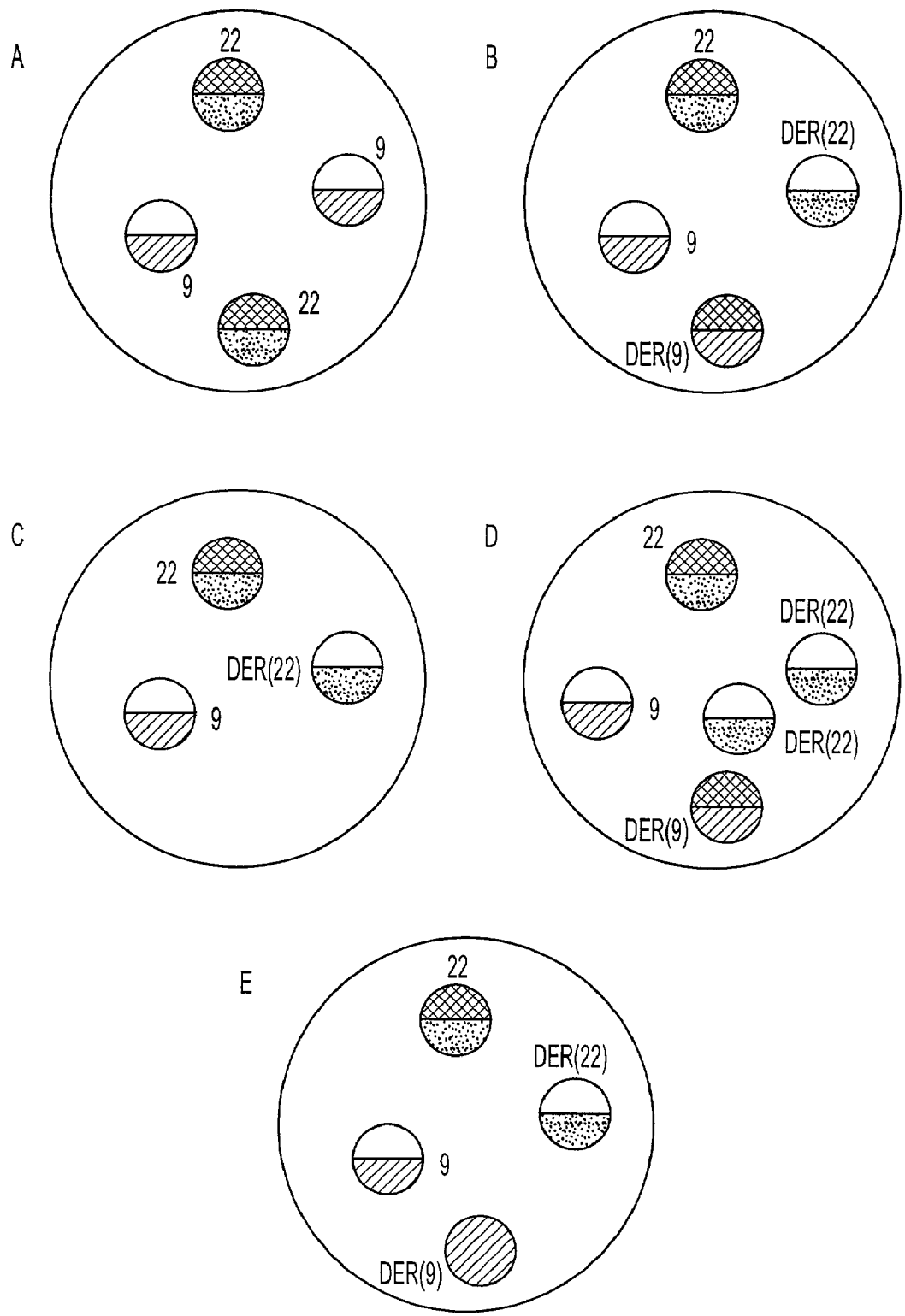
FIG. 4 is a diagrammatic representation of expected signal patterns using the F-FISH assay in normal, standard translocation, deletion and variant translocations commonly encountered in CML and cataloged in Table 2. The letter designations for each field correspond to those found in Table 2. Chromosomal probe designations for FIG. 4 are: Chromosome 9, proximal probe—single hatched pattern; distal probe—open pattern. Chromosome 22, proximal probe—stippled pattern; distal probe—double hatched pattern.
Figure 4:
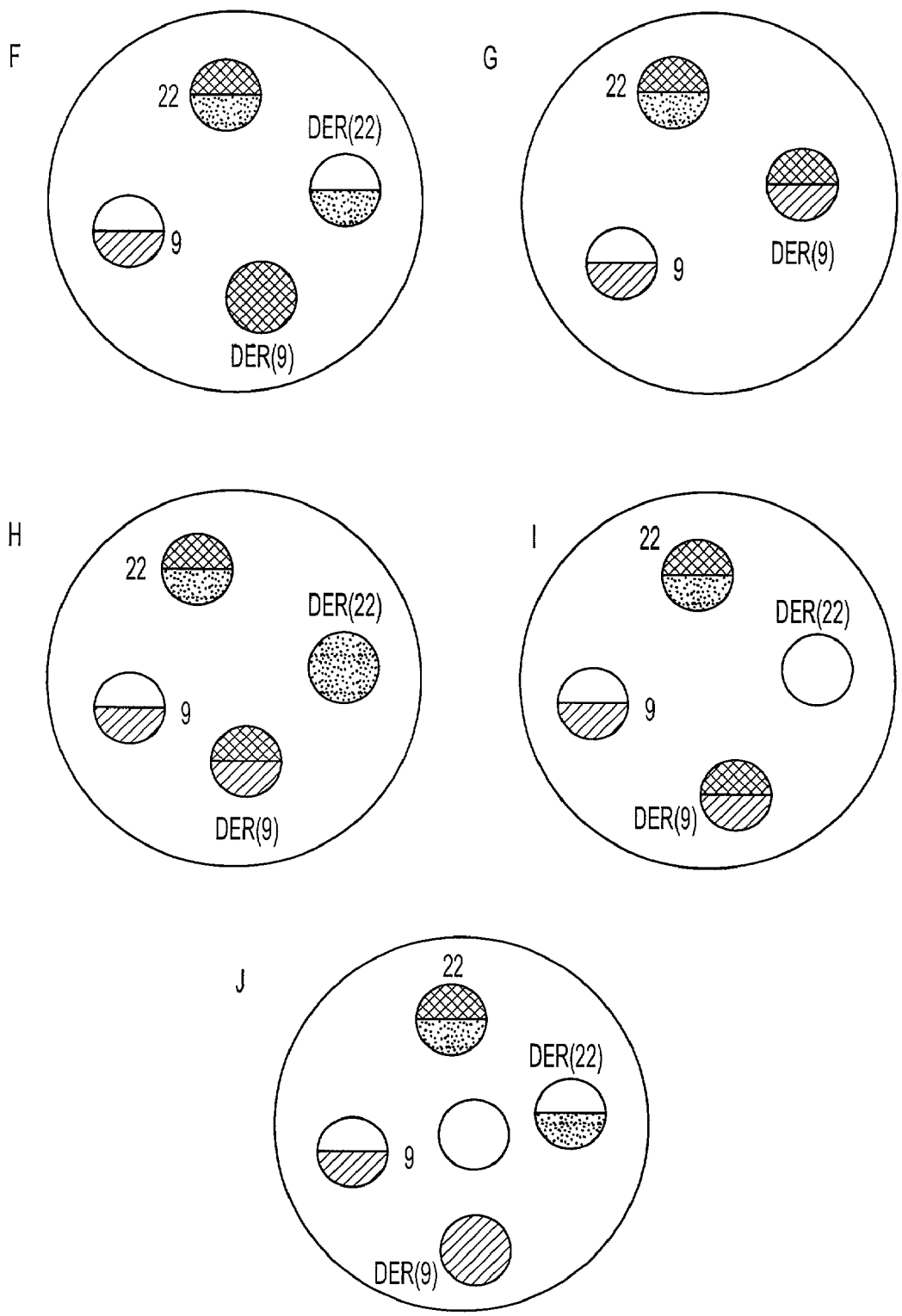

Detection of a variety of such rearrangements associated with CML are catalogued in Table 2 and the corresponding hybridization patterns depicted in FIG. 4. FIG. 4 Panel B illustrates the t(9;22)(q34;q11) translocation. The remaining panels of the figure depict the numerous alternative rearrangements that have been shown to occur in conjunction with the translocation, including the detection of deletions affecting specific chromosomes illustrated in Panels C, E and F. Panel D further illustrates how the F-FISH system is capable of detecting duplication of one of the rearranged chromosomes and, more specifically, identifying precisely which chromosomes have been duplicated.

TABLE 2

Chromosomal rearrangements found associated with Chronic Myeloid Leukemia

| Cell type | Signal Pattern | Inference |
| --- | --- | --- |
| A. Normal | Normal 9, 22 | No translocation |
| B. Tumor | Normal 9, 22, der(9) der(22) | Translocation positive |
| C. Tumor | Normal 9, 22, der(22) | Ph+, deletion of BCR/ABL region on der(9) |
| D. Tumor | Normal 9, 22 der(9), der(22) × 2 | der(9), double Ph+ |
| E. Tumor | Normal 9, 22, der(22), der 9 w/o telomeric region of 22 | Ph+, deletion of BCR region on der(9) |
| F. Tumor | Normal 9, 22, der(22), der 9 w/o centromeric region of 9 | Ph+, deletion ABL region on der(9) |
| G. Tumor | Normal 9, 22, der(9) | Deletion of BCR/ABL region on der(22) |

TABLE 2-continued

Chromosomal rearrangements found associated with Chronic Myeloid Leukemia

| Cell type | Signal Pattern | Inference |
| --- | --- | --- |
| H. Tumor | Normal 9, 22, der(9), der 22 w/o telomeric region of 9 | Deletion of ABL region on der(22) |
| I. Tumor | Normal 9, 22, der(9), der 22 w/o centromeric region of 22 | Deletion of BCR region on der(22) |
| J. Tumor | Normal 9, 22, der(22), isolated spots ABL centromeric and BCR telomeric regions | Variant translocation |

Based on F-FISH analysis, the current inventors have identified at least ten possible signal patterns excluding amplification (Table 2). Abnormal signal patterns other than the listed patterns may be possible with the addition or loss of one of more of same signals due to copy number changes for the corresponding chromosomes.

Panel A of FIG. 4 represents the hybridization pattern in normal cells. There are two sets of colocalizing spots in the normal hybridization pattern. One set consists of spots of first label (proximal probe represented by stippled pattern) colocalizing with second label (distal probe represented by double hatched pattern) and corresponding to chromosome 22. The second set consists of spots of third label (proximal probe represented by single hatched pattern) colocalizing with fourth label (distal probe represented by open pattern) and corresponding to chromosome 9.

The hybridization pattern in Panel B of FIG. 4 shows four sets of colocalizing spots and indicates that a reciprocal translocation has taken place between chromosomes 9 and 22. The hybridization pattern shows one set of colocalizing spots consisting of first label colocalizing with second label and corresponding to untranslocated chromosome 22. The second set of colocalizing spots consists of third label colocalizing with fourth label and corresponding to untranslocated chromosome 9. The third set of colocalizing spots consists of a first label and a fourth label and corresponds to a derivative chromosome 22 containing a centromeric region from chromosome 22 and a telomeric region from chromosome 9, i.e., the Philadelphia chromosome described supra. The fourth set of colocalizing spots consists of a second label and a third label and corresponds to a derivative chromosome 9 containing a centromeric region from chromosome 9 and a telomeric region from chromosome 22.

Panel C of FIG. 4 displays three sets of colocalizing spots. The first set consists of spots of first and second labels and corresponds to chromosome 22. The second set consists of spots of third and fourth labels and corresponds to chromosome 9. The third set consists of spots of first and fourth label and corresponds to the Philadelphia chromosome (der(22)). The Philadelphia chromosome could only have resulted from a translocation involving chromosomes 9 and 22. The hybridization pattern displays the der(22), (Philadelphia chromosome) but not the corresponding der(9), which would have been comprised of the centromeric region of chromosome 9 and the telomeric region of chromosome 22. The absence of der(9) indicates at the very least that the BCR/ABL region of the der(9) chromosome has been deleted, or that the entire der(9) chromosome has been deleted.

The hybridization pattern in Panel D of FIG. 4 displays five sets of colocalizing spots. One set consists of first label colocalizing with second label and corresponds to chromosome 22. The second set consists of third label colocalizing with fourth label and corresponds to chromosome 9. The third set consists of second label colocalized with third label and corresponds to a der(9) chromosome formed through a reciprocal translocation with chromosome 22. Analysis of the remainder of the hybridization pattern of Panel D illustrates the power of the F-FISH strategy to characterize cells with additional copies of one or both of the rearranged chromosomes, as is sometimes the case with cancer. There are three spots of first label in the hybridization pattern, indicating three copies of chromosome 22 (or a derivative of that chromosome), rather than the two found in diploid cells. As indicated supra, one of these first labels colocalizes with the second label and corresponds to an untranslocated chromosome 22. The other two first labels, however, colocalize with the fourth label to form the der(22) Philadelphia chromosome. The Philadelphia chromosome can only be formed through a translocation between chromosomes 9 and 22, yet only one of the third label spots corresponds to a der(9) and the other third label spot is colocalized with a fourth label spot corresponding to an untranslocated chromosome 9. This additional Philadelphia chromosome was likely formed by non disjunction in an earlier mitotic event.

Panel E of FIG. 4 shows a hybridization pattern of four sets of spots. One set consists of a spot of first label colocalizing with second label and corresponds to chromosome 22. The second set consists of colocalizing spots of third label and fourth label and corresponds to chromosome 9. The third set of spots consists of first label colocalizing with fourth label and corresponds to a der(22) chromosome formed through a reciprocal translocation with chromosome 9. The fourth spot is an isolated spot of third label. This isolated spot corresponds to a der(9) formed as part of the translocation event creating the der(22) chromosome, but during the translocation, the telomeric region of chromosome 22 was lost and not joined at the breakpoint of der(9). This left der(9) with a macrodeletion in its telomeric region, including the BCR gene region.

Panel F of FIG. 4 shows a hybridization pattern of four sets of spots. One set consists of spots of colocalizing first label and second label and corresponds to chromosome 22. The second set consists of spots of colocalizing third label and fourth label and corresponds to chromosome 9. The third set of spots consists of first label colocalizing with fourth label and corresponds to a der(22) chromosome formed through a reciprocal translocation with chromosome 9. The fourth spot is an isolated spot of second label. This isolated spot corresponds to a der(9) chromosome formed as part of the translocation event creating the der(22) chromosome, but during the translocation, the centromeric region of chromosome 9 combining the ABL gene region was deleted and the telomeric region from chromosome 22 joined. This pattern is not due to a variant translocation to a third chromosome because there is no isolated spot of the third label (der(9)) with a macrodeletion in the telomeric region) as would be expected in such a variant translocation.

Panel G of FIG. 4 shows a hybridization pattern of three sets of spots. One set consists of spots of first label colocalizing with second label and corresponds to chromosome 22. The second set consists of spots of third label colocalizing with fourth label and corresponds to chromosome 9. The third set of spots consists of second label colocalizing with third label and corresponds to a der(9) chromosome formed through a reciprocal translocation with chromosome 22. In this hybridization pattern, the der(22) which should have been formed by the translocation forming the der(9) chromosome noted supra is missing. This indicates that either the BCR/ABL region of the der(22) chromosome has been deleted to an extent such that label cannot bind, or the der(22) chromosome is missing entirely.

Panel H of FIG. 4 shows a hybridization pattern of four sets of spots. One set consists of colocalizing spots of first label and second labels and corresponds to chromosome 22. The second set consists of spots of third label colocalizing and fourth label and corresponds to chromosome 9. The third set of spots consists of second label colocalizing with third label and corresponds to a der(9) chromosome formed through a reciprocal translocation with chromosome 22. The fourth spot is an isolated spot of first label. This isolated spot corresponds to a der(22) chromosome formed as part of the translocation event creating the der(9) chromosome noted supra; however, the translocation resulted in a loss of the ABL gene region of the der(22) chromosome and the telomeric region of chromosome 9 was lost and never joined to chromosome 22.

Panel I of FIG. 4 shows a hybridization pattern of four sets of spots. One set consists of spots of colocalizing first label and second label and corresponds to chromosome 22. The second set consists of spots of colocalizing third label and fourth label and corresponds to chromosome 9. The third set of spots consists of second label colocalizing with third label and corresponds to a der(9) chromosome formed through a reciprocal translocation with chromosome 22. The fourth spot is an isolated spot of fourth label. This isolated spot corresponds to a der(22) chromosome formed as part of the translocation event creating the der(9) chromosome, but during the translocation the centromeric region of chromosome 22 was lost during the transfer of the telomeric region from chromosome 9 to form the der(22) chromosome.

Panel J of FIG. 4 shows a hybridization pattern of five sets of spots. One set consists of spots of colocalizing first label and second label and corresponds to chromosome 22. The second set consists of spots of colocalizing third label and fourth label and corresponds to chromosome 9. The third set of spots consists of first label colocalizing with fourth label and corresponds to a der(22) chromosome formed through a reciprocal translocation with chromosome 9. The fourth spot is an isolated spot of third label. This isolated spot corresponds to a der(9) chromosome formed as part of the translocation event creating the der(22) chromosome, but the translocation was variant, with the telomeric region of chromosome 22 never being transferred to chromosome 9 in the translocation. Instead, the telomeric region of derivative chromosome 9 was transferred to a third chromosome as indicated by the isolated fourth label spot. This hybridization pattern is not due to polyploidy and a chromosomal deletion because there are only two spots of each label present in the pattern, indicative of a diploid chromosomal preparation.

9. Probe Detection and the Use of Pseudo-Colors.

Probe labels of the present invention comprise all agents that can be detected physically or chemically and can be associated with the probes described herein. For example, probes of the present invention are preferably constructed with nucleic acids comprising labels of one or more fluorescent compounds that are typically conjugated to the base moiety. Other methods of the present invention utilize radioactive probes, each emitting particles of a characteristic energy and/or decay rate. Still other methods utilize probes comprising distinctive antigens that can be differentially detected by histochemical means.

The present invention also enables the detection of any given probe signal to be transformed to an alternative format easing display and/or interpretation. For example, a radioactive probe signal can be transformed into a colored light pattern displayed on a cathode ray tube; fluorescent probe emissions can be transformed into a digital representation; the digital representation can be transformed into a graphical computer printout and so forth. Other methods allow probes having different signal characteristics to be used together. For example, one method uses two probes differentially labeled with fluorescent compounds and two probes differentially labeled with radioactive isotopes. Although different detectors are used to monitor the positions of the respective probe sets, the data from the different detectors is gathered and transformed to present the data on a common display in the form of differentially colored spots. Typically, such transformations are performed by a software-driven computer.

Some methods of the present invention are capable of differentiating between signal intensities or color hues, thereby further increasing probe signal diversification. For example, one method can distinguish between bright red and dull red. Another method can distinguish between differences in the specific activity of probes labeled with a radioactive isotope. Additional methods comprise differential detection of different isotopes.

A useful aspect achieved from the use of pseudo-colors is the ability to resolve fusion signals. For example, in multicolor FISH assays, such as the F-FISH assay described in the present invention, there are a multitude of fusion signals that can result from the juxtapositioning of two or more probes. In the present methods, such fusion signals would typically be artifactual, resulting from random aspects inherent in chromosomal positioning during fixation. Using pseudo-colors, such artifactual fusion signals can often be resolved into the component signals, as a given fusion signal can only be formed through certain combination(s) of the labels used in the experiment. Another example of using pseudo-colors in the analysis process involves probes differentially radio-labeled. Even when such probes completely overlap, detection mechanisms common in the art are capable of distinguishing the radiation emitted by each probe based upon the energy of the particles emitted. In displaying the raw data, components of the fusion signal can therefore also be communicated, aiding in analysis.

The use of pseudo-colors also aids in data storage as all probe data, regardless of the nature of the probe label, can be stored in a common format.

IV. Additional FISH Methods for Detecting Deletions

In addition to the foregoing methods for detecting deletions, another general approach can be utilized to detect chromosomal deletions, including deletions that are associated with rearrangements (e.g., translocations) between two chromosomes. Similar to the segregating signal approaches discussed above, some deletion detection methods that are provided herein utilize a nucleic acid probe that hybridizes to a chromosomal region (binding region) that is either centromeric or telomeric to all known breakpoints associated with a particular translocation and which at least partially spans the region at which the deletion occurs. Thus, the probe does not hybridize to any region that includes any of the known breakpoints associated with the translocation. The probe is labeled with a detectable label to facilitate detection. In certain methods, the breakpoint region(s) associated with the translocation of interest are located within a gene, and the probe is designed to have a sequence such that the region to which it binds is located entirely outside the gene in which the breakpoints are located.

When analyzing a chromosomal sample, the probe is contacted with a chromosomal preparation. The probe hybridizes to the chromosomes that contain the binding region (or a portion thereof) to which the probe hybridizes. In a diploid cell, assuming there is not a complete deletion of the binding region, the probe binds to the two chromosomes that contain at least a portion of the binding region. A deletion from the binding region can be determined by detecting signal from the label associated the two chromosomes to which the probe is bound. If there is a partial deletion, then the signal from label on one chromosome has a lower intensity than signal from the other chromosome. If there is total deletion of the binding region, then label is only detected on a single chromosome. As noted supra, for a micro-deletion in which part of the binding site is retained, the magnitude of signal reduction is related to the extent of the deletion.

This general approach for detecting chromosomal deletions can be utilized independently or in combination with either the signal splitting or signal segregating approaches. The use of this deletion detection method with the split signal approach is useful because it enables detection of deletions which otherwise would have been impossible to detect. An example of the use of this deletion detection methodology in combination with a split signal approach is illustrated in FIGS. 13A-13C. FIG. 13A shows a first and second chromosome having genes A and B, respectively, prior to translocation and any deletion. The first chromosome includes a region susceptible to deletion as part of a translocation. Consistent with the signal segregating methodology described supra, a first probe bearing a first label and a second probe bearing a second label are selected to span the breakpoints of gene A and gene B, respectively. A third probe bearing a third label at least partially spans the region of the first chromosome at which a deletion can occur, but hybridizes to a region that is located entirely centromeric to the breakpoint. The interphase field for such a chromosomal arrangement from a diploid cell contains two colocalizing spots of first and third label corresponding to untranslocated chromosome 1 and two separate spots of second label corresponding to untranslocated chromosome 2.

The arrangement of the three labeled probes following a translocation that does not involve a deletion is illustrated in FIG. 13B. In this situation, a colocalized spot of first and third label and a separate spot of second label correspond to untranslocated first and second chromosomes, respectively. A colocalizing spot consisting of first, second and third label corresponds to the derivative chromosome 1. A fourth spot consisting of colocalizing first and second label arises from the derivative chromosome 2.

The arrangement of probes and the hybridization pattern arising from a translocation of the first and second chromosomes and a complete deletion of the probe 3 binding site is depicted in FIG. 13C. In this instance, the pattern includes a spot of colocalizing first and third label and a spot of second label indicative of untranslocated first and second chromosomes, respectively. The pattern also includes two spots of colocalizing first and second label corresponding to the derivative chromosome 1 and derivative chromosome 2. A spot containing colocalizing first, second and third label is not observed because of the deletion.

In the case of a deletion of only a fraction of the probe 3 binding site, a spot of colocalizing first, second and third label is observed in the interphase field. The intensity of the third label signal arising from this spot is reduced relative to the third label signal arising from third label hybridized to untranslocated first chromosome. The extent of the deletion can be assessed from the degree to which the third label signal is reduced.

While the foregoing examples have been discussed with respect to the hybridization pattern arising in an interphase field, it should be understood that these methods can also be utilized with metaphase chromosomes. Further, those of skill in the art will appreciate that analogous methods to those just described can be performed using the signal segregating approach described herein. When the deletion detection method is utilized in combination with the signal segregating approach, the probe utilized to facilitate detection of the deletion is still selected to hybridize to a region that is entirely centromeric or telomeric to the breakpoints involved in the translocation of interest and, in some instances, is further located outside the gene in which the breakpoints occur. The deletion detection probe is further selected such that it does not hybridize to a region that interferes with the ability of the distal or proximal probes to bind to the same chromosome to which it binds. As discussed above, the signal segregating approach is able to detect deletions even without a separate deletion detection probe. Thus, this probe can be utilized to augment the existing capability of the segregating signal approach.

V. Rendering FISH Probes Repeat Sequence Free

A. General

Recent advances in molecular genetics and genome analysis have resulted in the availability of a variety of reagents that can be used to generate DNA probes, e.g., yeast artificial chromosome (YACs) bacterial artificial chromosomes (BACs) and P1 artificial chromosomes (PACs). Well-developed YAC/BAC/PAC maps are available for most of the chromosomal regions involved in cancer translocations. However, artifacts in signals have traditionally been a source of problems with FISH analyses.

Such artifacts arise from two sources. One is non-specific binding of labeled DNA to protein in intact fixed nuclei. This can be partly overcome by treating the nuclei with proteolytic enzymes such as proteinase K or trypsin. With the recent advances in imaging technology, computer processing of images can also be utilized to reduce the background fluorescence arising from non-specific hybridization.

The second source of artifacts is non-specific cross hybridization of probes containing repeat sequences to complementary repeat sequences in the genome. Various suppression methods have traditionally been utilized to address this problem. One such approach involves pre-annealing labeled probes with unlabeled DNA that contains only repeat sequences (repeat DNA), such that probes with repeat segments bind to the repeat DNA, thus allowing such probes to be partially separated from probes without repeat sequences. Typically, the repeat DNA utilized is human Cot-1 DNA or total human genomic DNA. The unbound probes collected after a suppression step includes fewer probes with repeats. However, this particular approach, while helpful in reducing the number of copies of probes with repeat sequences, nonetheless does not adequately address the issue. The problem is that for any given probe present in multiple copies, often the suppression step fails to bind up all the copies of the probe. Thus, even after the suppression step, although one may have reduced the number of copies of any given probe, it is probable, in fact likely, that additional copies of such probes remain in solution. Consequently, with conventional suppression steps, the complete suppression of all repeat sequences is difficult. Furthermore, in suppression steps, a considerable amount of unique sequences may also reanneal, thus resulting in reduced signal intensity during hybridization. Hence, avoiding the suppression step in a hybridization experiment can improve signal intensity and specificity.

Figure 8:
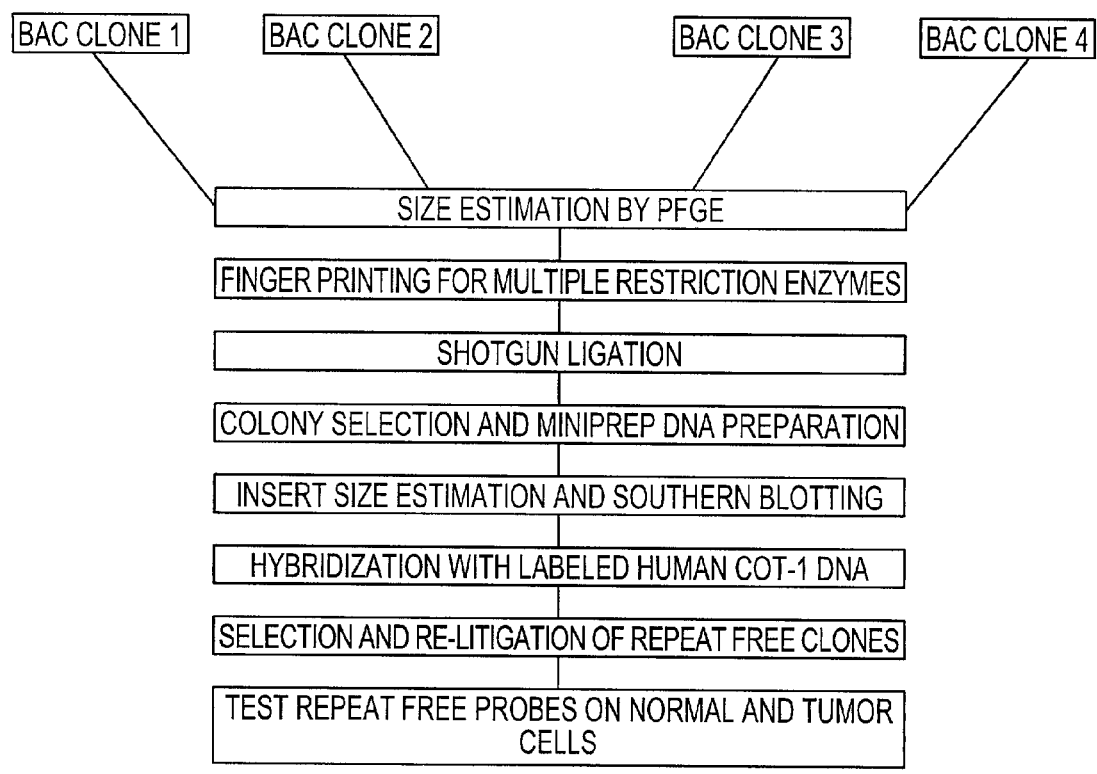
FIG. 8 is a flow chart summarizing certain steps in a process for removing repeat sequences from clonal libraries. The remaining clones can be utilized in the preparation of the desired probes. Because the resulting probes have been freed of many repeat sequences, cross-hybridization problems are reduced or completely eliminated.

The methods described herein utilize a different approach for addressing the non-specific cross hybridization problem, an example of which is summarized in FIG. 8. In general, the approach involves cloning a plurality of sequences that flank all the known breakpoints for a particular translocation of interest. The resulting cloned sequences are then contacted with one or more repeat sequences to allow probes containing complementary repeat segments to hybridize to the repeat sequences. Clones of sequences that fail to anneal to the repeat sequences are selected and used in the detection and identification of the translocation of interest. With this approach, the problems associated with traditional methods involving hybridization of probes to repeat sequences are avoided. Conventional approaches simply result in the enrichment of a population of probes for those lacking repeat sequences. However, as described above, even for those probes that hybridize to the repeat sequence, frequently other copies of the same probe remain that have not hybridized to the repeat sequence.

The methods described herein, however, can substantially avoid this problem. With the present method, one determines if any given cloned probe anneals to the repeat sequence. If so, such a probe is not utilized as a probe in a FISH assay since it contains repeat sequences. By utilizing a binary detection scheme (i.e., a scheme in which one determines whether a given clone hybridizes to repeat sequence or not) to identify probes that contain repeat sequences, one can readily identify potential probes to utilize (or exclude) in the detection of any given translocation. This method avoids the problem of the conventional approach. Any binding of a cloned probe to the repeat sequence is an indication that particular clone includes repeat sequences and should not be used in the further development of probes. Hence, unlike certain conventional suppression approaches, one can essentially eliminate particular probes that have repeat sequences.

As depicted in FIG. 8, the method by which the claimed probes are constructed yields probes that are comprised of stretches of DNA homologous to portions of the probe binding region, of at least a minimum size, and completely free of repeat sequence DNA. As depicted schematically in FIGS. 9A and 9B, the stretches of DNA from which the probe is constructed are typically not contiguous, being interspersed between both repeat sequences (the dark bands in FIGS. 9A and 9B) and cloned sequences deemed too short to be included in the probe. It should also be noted that the order in which the clones are ligated together to make the probe need not reflect the order in which the clones appear in the chromosomal DNA. For example, in FIG. 9A, the sequences making up the probe are aligned "A", "B", and "C" in the chromosome, but their relative positions in the probe are "B", "A", "C" The consequence of this construction is that one is afforded a heterogenous set of probes, each containing one or more stretches of DNA homologous to a subregion of a probe binding region. This approach allows for multiple copies of probe to bind specifically to a much greater expanse of DNA without the difficulties created by background recognition of repeat sequences found in the prior art.

An additional aspect of the probe construct is that it facilitates mapping of deletions that encroach into the probe binding region. As a deletion removes part of the probe binding region, subregions that previously supported probe hybridization are removed. Such an occurrence is depicted in FIG. 9B. This decrease in probe hybridization necessarily decreases the amount of label associated with the probe binding region. The loss of label from the probe binding region, in turn, lowers the intensity of the signal produced. By comparing the signal intensity emitted by a chromosome carrying such a deletion with the signal intensity emitted from the analogous site on a homologous chromosome which has not undergone such a deletion, the extent of the deletion into the probe binding region can be estimated.

By utilizing the segregating probe approach as disclosed herein, in combination with methods for generating probes that are free of repeat sequences, three important criteria are met. First, as the probes hybridize to chromosome regions flanking all the breakpoints, the signal is not "split" between derivative chromosomes after a translocation event, as occurs when probes span the translocation breakpoint. This feature allows for the identification of both derivative chromosomes (as well as chromosomes that have not undergone translocation) and ensures the signal intensity generated by the probe is maintained on the derivative chromosomes. Second, as the probes produced are free of repeat sequences, they will not recognize homologous repeat sequences found throughout the genome. This feature of the methods decreases background noise caused by spurious hybridization of probes to repeat sequences and significantly lessens the possibility of generating a false positive signal pattern. Third, by reducing background noise and increasing overall probe signal, the probe constructs described herein facilitate automated cell scoring methods, making the diagnosis and evaluation of diseases involving chromosomal rearrangements, including cancer, routine.

B. Methodology

The methods begin by initially identifying regions of DNA that can serve as potential probes for detecting a translocation of interest. This is done using a database of gene sequences (e.g., GenBank, http://www.ncbi.nlm.nih.gov/) to identify segments of DNA that flank all the known breakpoints for a particular reciprocal translocation of interest. The regions examined are those that typically fall within less than 1 Megabase (Mb) of a potential breakpoint, or within the regions listed supra. Once such regions have been identified, primer sequences located upstream and downstream of these regions are selected using the same databases. These primers can be used to isolate the potential probe sequences from a variety of libraries. Typically, the libraries that are screened are BAC, YAC or PAC libraries that are commercially available (e.g., PAC and BAC libraries are available from Incyte Genomics of St. Louis, Mo.; a YAC library is available from Research Genetics, Huntsville, Ala.). A variety of different screening methods can be utilized to screen the libraries to identify which clone includes the potential probe sequences. Often the screening process is accomplished by conducting PCR with the primers just described. Positive clones (e.g., a BAC clone that generates amplified product) are then isolated according to standard techniques. A variety of hybridization methods for libraries arranged in nylon membrane filters can be screened using the primer sequences.

The isolated clones are subsequently characterized and validated by determining their specificity and sensitivity in normal and tumor interphase and metaphase cells. Typically, this involves initially fixing test cells to a support (e.g., microscope glass slides) and then permeabilizing the cells with an appropriate permeabilizing solution (hybridization solution). A solution containing the fluorescent labeled probes is then contacted with the cells and the probe is allowed to hybridize with chromosomes. Excess probe is washed away and the presence of hybridized probe detected. Those clones that exhibit the desired selectivity (i.e., clones that hybridize only to the appropriate normal and derivative chromosomes) and sensitivity are isolated for further analysis.

Those clones isolated in the preceding step are then completely or partially digested with one or more restriction enzymes to generate a population of overlapping nucleic acid fragments. The resulting fragments are subcloned into vectors (e.g., plasmids) using shotgun ligation (Sambrook and Russel, 2001). The result is a library of subclones from individual clones. The size of the insert of each subclone is checked. This can be accomplished by various size-based separation procedures, but typically is done by agarose gel electrophoresis. Prior to subcloning, the insert size for each clone will be estimated by pulsed field gel electrophoresis. (Schwartz and Cantor, 1984).

The resulting subclones are then screened to remove clones that have repeat sequences. In certain methods, the size separated inserts are transferred to a support suitable for conducting hybridization experiments. Such transfers can be performed, for example, by transferring the inserts to a nitrocellulose filter or nylon membranes by capillary transfer. The resulting filter is then contacted with a solution containing labeled nucleic acids (e.g., radioactively labeled) having repeat sequences. A variety of different types of nucleic acids including repeat sequences can be utilized in this step. Suitable repeat sequences include Human Cot-I DNA, which is a fraction of total genomic DNA enriched for repeat sequences. The goal in this step is to identify subclones that include repeat sequences. As indicated supra, the suppression methods described herein are designed to substantially reduce the number of probes that have repeat sequences to achieve increased specificity. Consequently, clones that do not hybridize with the nucleic acid including the repeat sequences are selected to obtain a population of subclones in which the number having repeat sequence is substantially reduced; subclones that do hybridize to the repeat sequences are discarded.

To further ensure that subclones identified as being free of repeat sequences do in fact not contain repeat sequences, each of the negative clones are reconfirmed by Southern analysis. In particular, Southern blots are conducted using total human genomic DNA. These blots are performed by digesting total human genomic DNA with the same restriction enzymes utilized in the sub-cloning step. Each of the repeat-free subclones should yield a single hybridizing fragment of its own size, thus confirming its size, repeat-free status and freedom of artifacts.

Those subclones passing the reconfirmation test are religated by blunt end ligation to obtain a single, larger repeat clone (typically less than 5 kb in length). Finally, the religated clones are tested by FISH for their specificity and sensitivity. Clones utilized for further analyses are those that hybridize only to the chromosomes or derivative chromosomes involved in the translocation of interest. Once hybridized, probes based upon such clones should also generate bright, easily detectable signals.

Each of the foregoing probe preparation steps is described in greater detail in Example 1 infra and summarized in FIG. 8. The utility of the approach just described would not have been predicted in advance because one might conclude that all probes might have sufficient repeat sequences such that at the conclusion of the process no probes would be left. However, this in fact has not proved to be the case. The identified single BAC, P1 or YAC clone is known to contain large portion of repeat sequences. Additional clones can be generated by chromosome walking on either side of the first clone utilizing the end sequences of the first clone. This process can be accomplished by sequencing the ends of the first clone and selecting primers from the sequences to screen a genomic library.

C. Final Probe Characteristics

1. Size

In general the length of the probe is selected to be sufficient to maintain specificity but is sufficiently short to avoid difficulties in preparing the probe. As indicated supra, the probe is also selected to anneal at a region flanking all of the known breakpoints for any given translocation. Usually the probe is more than 5 KB, but can be larger. For example, the probe can be 6, 7, 8, 9 or 10 KB or more in length, or any integer between the foregoing sizes.

2. Synthesis

Once appropriate probes have been identified and confirmed to have the desired specificity and sensitivity, probes can be prepared by growing large-scale cultures and DNA prepared by standard alkaline lysis method (Sambrook and Russel, 2001). Alternative methods for the preparation of probe DNA includes PCR amplification of utilizing degenerate oligonucleotide primers (DOP-PCR) method are described by Telenius et al., (1992).

3. Labeling

Labels can be attached to the probes in a variety of ways. One option involves chemical modification of a nucleic acid by substituting a derivatized base for a naturally occurring base. Adducts can also be formed which, after hybridization, render the nucleic acid detectable by immunochemical stains or affinity labels (e.g., biotin/avidin). For example, certain indirect labeling methods involve the incorporation of a hapten (e.g., biotin, digoxigenin) into the DNA by enzymatic reactions. Following hybridization of the probe to the chromosome, a label is attached to the hybrid through the use of immunological methods, in particular the use of a labeled antibody that specifically binds to the antigen incorporated into the probe. Such methods are discussed further, for example, by Tchen et al. (1984) Proc. Natl. Acad. Sci. 81:3466-3470; and Langer et al. (1981) Proc. Natl. Acad. Sci 78:6633-6637. Another option is to label the probes directly through the incorporation of labeled nucleotide during synthesis of the probe. Such an approach is described in greater detail in Example 2 below. Further methods are discussed by Smith et al. (1985) Nucleic Acids Research 13:2399-2412; and Connolly et al. (1985) Nucl. Acids Res. 13:4485-45. Still another option is to attach the label via a linker attached to a modified nucleotide (see, e.g., U.S. Pat. No. 5,491,224). Multiple different labels can be attached to a probe. For example, combinatorial fluorescence methods can be utilized in which various combinations of dyes are utilized (see, e.g., Ried et al. (1992) Proc. Natl. Acad. Sci. USA 89:1388-92 and U.S. Pat. No. 5,817,462).

A variety of suitable dyes are available. Certain methods utilize fluorescent molecules as labels, as a number of commercial instruments have been developed for the detection of fluorescent labeled nucleic acids. A variety of fluorescent molecules can be used as labels including, for example, fluorescein and fluorescein derivatives, rhodamine and rhodamine derivatives, naphthylamine and naphthylamine derivatives, cyanine and cyanine derivatives, benzamidizoles, ethidiums, propidiums, anthracyclines, mithramycins, acridines, actinomycins, merocyanines, coumarins, pyrenes, chrysenes, stilbenes, anthracenes, naphthalenes, salicyclic acids, benz-2-oxa-1-diazoles (also called benzofurazans), fluorescamines and bodipy dyes.

While the in situ hybridization methods described herein typically utilize fluorescent labels, other labels can be used. Other suitable labels include, but are not limited to, chromophores, molecules that emit chemiluminescence, radioisotopes, electron dense particles, enzymes, cofactors, substrates for enzymes and ligands having specific binding partners (e.g., avidin/biotin).

VI. Methods of Use

The foregoing methods for generating probes free of repeats can be utilized to generate repeat-free probes that can be utilized in a variety of FISH approaches, including the segregating (both S-FISH and F-FISH methods) and split signal approaches described supra. The segregating approach is preferred because of the increase in sensitivity the approach provides. The methods can also be utilized to develop probes for the detection of virtually any chromosomal translocation.

Methods utilizing probes designed as described herein typically involve (a) fixing a chromosome sample to obtain a chromosome spread; (b) treating the fixed sample to make the target DNA more accessible to the probes; (c) contacting the treated sample with probes prepared as described herein appropriate for the translocation being detected and allowing the probes to hybridize with the target sites; (d) washing the hybridization complexes with rinse solutions to remove unhybridized probes; and (e) detection of probes that have hybridized to the target sites.

A variety of suitable fixatives are available for preparing the chromosomal spread. Examples of such fixatives include, but are not limited to, acid acetone solutions, various aldehyde solutions (e.g., formaldehyde, paraformaldehyde and glutaraldehyde) and acid alcohol solutions. Examples of specific chromosomal fixatives are discussed, for example, by Trask, et al. (1985) Science 230:1401-1402.

Treating the chromosomal spread with an agent or agents that remove proteins from the chromosomes can enhance the ability of probes to access target sites in the chromosomes. Agents useful for performing such removal include certain enzymes (e.g., pronase or proteinase K, trypsin and pepsin) and mild acid. Deproteinization is performed with an enzyme concentration and for a time period that increases accessibility to allow for hybridization between probe and target sites; however, the period is sufficiently short to prevent a loss of morphological detail that renders subsequent chromosomal identification difficult. An alternative is to deproteinize chromosomes by mild acid extraction. Thus, certain deproteinization methods involve treating the chromosomal spread with 0.02-0.2 N HCl followed by high temperature (e.g., 70° C.) washes. An optional pretreatment with RNase can be utilized to remove residual RNA from the chromosomal spread.

The chromosomal spread is then denatured so the probes can bind to the target sites in the chromosomes. Various denaturation conditions can be utilized. Certain denaturation methods include incubation in the presence of high pH, low pH, high temperature and/or various organic solvents (e.g., formamide, tetraalkylammonium halides). Denaturants are usually removed prior to contacting the chromosomal spread with the probes using established washing procedures. For example, when formamide is used as a fixing agent, common washes involve a series of ice-cold ethanol rinses at 70%, 80% and 90% ethanol.

The denatured chromosomal spread is then contacted with probes prepared according to the methods described herein. Hybridization is conducted under conditions and for a time period sufficient for the repeat-free probes to hybridize with the complementary sequences in the chromosomes. Optimal hybridization conditions depend upon several factors such as salt concentration, incubation time between probes and chromosomal spreads and concentration, composition and length of the probes as will be appreciated by those of ordinary skill in the art.

Once probes have annealed to their complementary sequences, any unbound probes can be washed away. The resulting hybridization complexes are spectrally analyzed to detect such complexes. A variety of different optical analyses can be utilized to detect the complexes. Spectral detection methods are discussed, for example, in U.S. Pat. No. 5,719, 024, and by Schroeck, E. et al. (1996) Science 273:494-497; and Speicher, R. M., et al. (1996) Nature Genetics 12:368-375.

Further guidance regarding general FISH procedures are discussed, for example, Gall and Pardue (1981) Methods in Enzymology 21:470-480; Henderson (1982) International Review of Cytology 76:1-46; Angerer, et al. (1985) in "Genetic Engineering: Principles and Methods" (Setlow and Hollaender, Eds), Plenum Press, New York.

The following examples are provided to illustrate certain aspects of the methods and probes disclosed herein. Accordingly, these examples should not be construed so as to limit the scope of the appended claims.

Example 1

Experimental Design

I. General

The general experimental strategy for developing probes to be utilized in FISH assays utilizing the signal segregation approach described supra involves the following steps: (1) generation of probes by screening a library (e.g., a PAC or BAC library) to identify probes that flank breakpoints for a translocation of interest; (2) testing the probes for chimerism and signal quality on normal metaphase and interphase nuclei; (3) testing the probes for detection of the translocation in nuclei from metaphase and interphase nuclei derived from multiple tissues; and (4) testing the probes on follow-up samples to ensure the probes have the appropriate sensitivity and specificity.

II. Screening of Human Genomic BAC or PAC Library and Probe Confirmation Testing A. Screening BAC Library.

In some of the following examples, the clones utilized to prepare the probes are obtained by screening a human genomic BAC library, either by PCR or probe hybridization methods according to the manufacturer's protocols (Incyte Genomics, St. Louis, Mo.).

B. Screening PAC Library.

In some of the other examples, clones are obtained from a PAC library. A PAC library was constructed by ligating a Sau3A1 partially digested human genomic DNA to the BamH 1 cloning site of the PAC vector. The ligation mixture was electrophoretically introduced to NS3516 bacterial cells to create a 16.5 KB plasmid containing a genomic insert having an average size of 120 kb. The PAC library was constructed by arraying each clone into micro titer dishes. The entire library is arrayed in 321 micro titer dishes. Each dish contains 384 wells in 24 columns and 16 rows. DNA prepared from each dish is combined individually in blocks of ten to create assay pools. A total of 32 upper pools are generated by combining 10 dishes. Thus, upper pool 1 contains clones pooled from plates 1-10. This pattern continues through upper pool 32 that contain clones from plates 311-321.

The 32 upper pools are screened by 32 individual PCR reactions using the described primers designed from the regions described in the following examples. These PCR reactions identify one of the upper pools that contain 10 plate pools. The next round of 10 PCR reactions is performed to identify one of the 10 plate pools. The last experiment of 40 PCR reactions identifies the well within the plate that contains the clone of interest. This experiment will be done for each of the primers individually to screen the library.

C. Rendering the Probes Repeat Sequence Free.

The identified clones are purified of probes that contain repeat sequences according the methods set forth supra. This increases the specificity of the remaining clones for the sequences of interest.

D. Testing Probes for Chimerism and Signal Quality on Normal Metaphase and Interphase Nuclei.

Each BAC clone or its derived pool probes is tested for chimerism, cross-hybridization, and signal strength on metaphase and interphase nuclei from PHA-stimulated and cultured mononuclear blood cells from multiple (e.g., five) normal individuals.

E. Testing the Probes for Detection of Translocations in Metaphase and Interphase Nuclei Derived from Multiple Tissues.

The probes are tested in biopsy samples from patients with lymphomas from the various translocations comprising peripheral blood, lymph node, bone marrow, and other tissues, as described in the experimental methods sections in Example 2. Pre-set criteria for accepting and rejecting normal versus translocation cells are established and adhered to in conducting the analyses. For each tissue type, at least 15 cases are tested.

F. Testing the Probes on Follow-up Bone Marrow Samples.

In order to detect residual tumor cells, post treatment (chemotherapy, bone marrow transplantation) samples from 15 cases are similarly analyzed using the probes disclosed infra.

G. Preparation of BAC/PAC DNA.

Following successful isolation of BAC and/or PAC clones, large-scale preparation of DNA for each clone is made following established protocols and/or the protocol described in the manufacturer's BAC and PAC manuals (e.g., Incyte Genomics, St. Louis, Mo.).

Example 2

Experimental Protocols

I. Preparation of Nuclei from Different Tissue Types

General methods for preparing nuclei from a variety of tissue sources are described by Heim and Mitelman (1995); ACT manual (1991); and Verma and Babu (1989). Additional disclosure for isolation methods for specific tissue types is provided in the following sections.

A. Nuclei and Metaphase Chromosomes from Normal Individuals

Heparinized peripheral blood samples collected from normal individuals are set up for the preparation of nuclei to be used in control studies. Briefly, 0.5 to 1.0 ml of peripheral blood is inoculated to 10 ml of RPMI-1640 medium supplemented with 15% fetal bovine serum and 1% L-glutamine and streptopenicillin. 0.2 ml of (1 mg/ml) phytohemagglutinin is added and the cultures incubated at 37° C. for 72 hours. One hour prior to harvest, 2 ml (11 g/ml) of colcemid solution is added and incubated for 1 hour at 37° C. The cultures are harvested by treating cells with pre-warmed hypotonic solution (0.075M KCl) for 15-20 minutes and fixed with 3:1 methanol acetic acid fixative. The slides are made following air drying method.

B. Lymph Node and Other Tissue Biopsies

The tissues are minced thoroughly in 2-3 ml of growth medium in order to get a single cell suspension and washed with growth medium and direct harvest is made following hypotonic treatment (0.075M KCl) and methanol acetic acid (3:1) fixations. The slides are made following air drying method.

C. Bone Marrow Samples

Clot free bone marrow aspirates are used to prepare nuclei by direct harvest method. Initially the cells are treated with hypotonic solution (0.075M KCl) and followed by methanol acetic acid (3:1) fixation. The slides are made following air-dry method.

D. Paraffin Embedded Tissue

One to three (25-50 µM) thick sections cut from paraffin embedded blocks are treated with xylene to remove paraffin and washed in absolute alcohol to remove xylene. The sections are rehydrated by passing through a series of 95%, 70%, 50% alcohol and finally suspended in water. The cells are dissociated by treating with 0.5% pepsin in 0.9% sodium chloride (pH 1.5) at 40° C. The digestion is halted by adding PBS (without Ca and Mg), which alters the pH and consequently stops the activity of pepsin. Nuclei are stored in PBS at 4° C. until further use.

II. Probe Labeling and Hybridization

Probes utilized for FISH analysis are labeled by standard nick translation methods using commercially available nick translation kits (GIBCO-BRL) according to the manufacturer's instructions or by using other non-enzymatic methods of labeling (Kreatech Diagnostics, Netherlands). Probe labeling by utilizing modified nucleotides and (Fluorescein coupled with dNTP's, Texas red or Rhodamine conjugated dNTP's) incorporation of fluorescent dyes to DNA probes by chemical methods are utilized to obtain green and red colored signals, respectively. The labeling of probes are not limited to green and red colors; multiple colors, as many as four different colors, can be utilized by labeling each probe with single color. Following labeling reactions, the unincorporated nucleotides are separated by passage through Sephadex G-50 columns. The samples are precipitated with absolute alcohol and resuspended in hybridization mixture (50% formamide, 2×SSC, 10% dextran sulphate, 1% Denhardts) and stored at −20° C. until further use. Approximately 200 ng of each probe is used for hybridization.

Prior to hybridization, the slides are pretreated by incubating with 2×SSC for one hour at 37° C. followed by passing through 70%, 80% and 100% alcohol for dehydration. The slides are denatured at 70° C. in denaturing solution (70% Formamide, 2×SSC) and passed through cold ethanol series. Simultaneously, the probes are denatured and placed on slides and hybridized overnight at 37° C. Post hybridization washes are performed at 45° C. in prewarmed 2×SSC solution twice followed by one room temperature wash in 2×SSC. The slides are counterstained with antifade solution containing 4,6-diamino 2-phenylindole (DAPI, Oncor, Gaithersburg, Md.).

III. Scoring of FISH Signals

In order to define the diagnostic threshold of assays for the detection of translocations utilizing the probes developed by the methods described herein, FISH analysis on interphase nuclei from normal individuals are investigated utilizing probes labeled with a green fluorophore for one chromosome involved in the translocation and probes labeled with red fluorophores for the other chromosome (other colors can be utilized). For each control and tumor specimen, at least 500 nuclei are analyzed following stringent criteria. In control specimens, cells are scored as normal when two separate green and red signals are observed. For closely placed red and green signals, the distance between each signal should be at least twice the size of one signal, and is considered a normal pattern. Similarly, a fusion or co-localizing signal is scored when the distance between red and green signals is less than one signal size. In tumor specimens, the same stringent criteria are followed when normal cells are encountered. Tumor cells are scored only when two clear fusion signals and a single red and green signal are observed. The same criteria are followed for all different tissue types.

IV. Quality Control

For each batch of DNA preparation, test hybridization is performed for each clone on normal metaphase chromosomes for their specificity. Different hybridization experiments are carried out using varying amount of probes to evaluate the optimum probe concentration to obtain strong hybridizing signals, on all different tissue types, which can be observed and scored directly under a microscope.

Example 3

Detection of the t(11;14)(q13;q32) Translocation in Mantle Cell Lymphoma

I. Background

As indicated above, the Mantle Cell Lymphoma (MCL) is a subtype of Non-Hodgkin's lymphoma (NHL) originating from pre-immune B-cells in the mantle zone of the primary follicles in secondary lymphoid organs. (Weisenburger 1992; Raffeld et al, 1991; Banks et al., 1992). The t(11;14)(q13;q32) translocation has been identified as the consistent cytogenetic abnormality in 70% to 90% of MCLs (Tsujimoto et al., 1984; Williams et al., 1991; Coignet et al., 1996).

As can be seen from FIG. 5A, the BCL1 gene is organized in a centromere to telomere (5'-3') orientation on chromosome band 11q13 spanning about 15 kb of the genomic region with five exons (Motokura et al., 1993). The t(11;14)(q13;q32) translocation does not disrupt the BCL1 gene open reading frame that contains 295 amino acids. The BCL1 gene is located 130 kb telomeric to the major translocation cluster region. In the majority of cases, the BCL1 breakpoints are clustered within a 63 base pair region of the major translocation cluster (MTC) of the BCL1 locus. Several studies have shown that breakpoints can occur telomeric of the MTC in a region about 120 kb between MTC and CCND1 gene and these studies have identified two minor cluster regions called mTC1 and mTC2.

The IGH locus is on chromosome 14q32 and is organized in a telomere to centromere orientation. It consists of a set of V, D, and J region segments that rearrange and join to create the active IGH V domain. The V region spans about 1100 kb upstream of the JH region. The D region lies between V and J segments. A more complex C region within about 200 kb contains 11 C region segments. The position of all genes within IGH region is shown in FIG. 5A.

The t(11;14)(q13;q32) translocation breakpoint in the IGH gene has been found to occur within or directly adjacent to a JH segment. In most instances (more than 80%), the breakpoints on chromosome 11q are clustered in a region known as the major translocation cluster (MTC), (Rimokh et al., 1990; Williams et al., 1993; Vandenberghe et al., 1992). Additional breakpoints are located between MTC and the BCL1 gene within regions referred to as minor translocation cluster regions 1 & 2 (mTC1 & mTC2). These clusters span about 120 KB upstream of the CCND1 gene at 11q13 (de Boer et al., 1993; Rimokh et al., 1993).

Since MCLs are morphologically highly heterogeneous, its classification as a distinct entity was a controversial subject for several years. Due to its morphologic variations, MCLs have been classified as small lymphocytic lymphoma/chronic lymphocytic leukemia (SLL/CLL) and follicular center cell lymphomas of both follicular and diffuse type (Raffeld et al., 1991). Recent studies have identified a characteristic pattern of antigen expression in MCL that are different from typical SLL/CLL cases, despite their morphologic heterogeneity, the MCL is diagnosed by CD5+, CD43+ and CD23– expression pattern by immunohistochemistry which has helped to define MCL as distinct disease entity (Harris et al., 1994).

Although MCLs have been known to have distinct antigen expression patterns, identification of malignant lymphocytes or MCL cells is difficult for pathologists. In addition, due to the dispersed nature of the breakpoints on chromosome 11q13, conventional molecular studies, such as Southern blotting and PCR, are not useful for detecting all the breakpoints. By Southern blot analysis about 50% of the MCL cases have been found to have rearrangements. This analysis requires multiple probes covering the entire 120 kb breakpoint cluster region. Recent studies have indicated additional breakpoints in the region 20 kb centromeric to the MTC locus (Galiege-Zouitina et al, 1994; Wlodarska et al., 1993). PCR is also of limited value because of difficulties in quantification and its tendency to generate spurious or false positive results due to amplification of DNA sequences from dead tumor cells or even from free DNA lysed still present in the specimen.

II. Experimental Design:

A. Probe Generation

1. Probes for BCL1 Region

Probe 1: A BAC clone proximal to the MTC region (probe 1, FIG. 5A) of the BCL1 locus on 11q13 is generated by using the following primers: F-5' AAGGTGTGAGGATCACTGG3' (SEQ ID NO:1); R-5'AGCTCATGGGGGCTATT3' (SEQ ID NO:2) derived from the D11S1337 (http://carbon.wi.mit.edu) by screening a BAC library. In the nuclei carrying the translocation, this probe remains on the der(11) chromosome and generates a fusion or co-localizing signal in combination with the IGH probe from region 3.

Probe 2: A BAC clone telomeric to the BCL1 gene region (probe 2, FIG. 5A) is generated by using the following primers: F-5'TTTCTGGGTGTGTCTGAAT3' (SEQ ID NO:3) R-5'ACACAGTTGCTCT AAAGGG T3' (SEQ ID NO:4) derived from the FGF3 gene. In the nuclei carrying the translocation, this probe segregates to the der(14) chromosome in translocations involving all the MTC, mTC1 and mTc2 breakpoints within the BCL1 locus on 11q13, and results in a fusion or co-localizing signal with the IGH probe from region 4.

2. Probes for IGH Region

Probe 3: A BAC clone covering the probe 3 region of the IGH gene (FIG. 5A) is generated using the following primers derived from the sub-telomeric V region of the IGH gene to screen the BAC library: F-5'TGTTTGAAGAAGGGAGTCGT3' (SEQ ID NO:5); R-5'CCCACTCCATGTCTTCTGTT3' (SEQ ID NO:6). In the nuclei carrying the translocation, this probe segregates to the der(11) chromosome and generate a fusion or co-localizing signal in combination with probe 1.

Probe 4: A BAC clone covering the probe 4 region of the IGH gene (FIG. 5A) is generated using the following primers derived from the Cα region to screen the library: F-5'CCACTCAGTGTGACCTGGAGCGAA3' (SEQ ID NO:7); R-5'CTCCCCTGGCTTTTC TGGAACTGG3' (SEQ ID NO:8). In the nuclei carrying the translocation, this probe remains on the der(14) chromosome and generates a fusion or co-localizing signal in combination with the relevant BCL1 probe.

3. Screening of Human Genomic BAC Library and PCR Detection of the t(11;14)(q13;q32) Translocation A human genomic BAC library is screened according to the screening methods described supra, including Example 1, utilizing the primers described in the preceding paragraph to identify BAC clones harboring the sequences of interest. Clones so identified are subsequently purified of probes that contain repeat sequences, tested for chimerism, cross-hybridization, and signal strength, and then subjected to follow-up testing as further described in Example 1.

III. Results

The BCL1 and IGH region probes were tested on normal and tumor metaphase and interphase cells. The BCL1 probe was labeled green and the IGH probe labeled red. In normal interphase nuclei and metaphase chromosomes, the probes exhibited unambiguous signals with no cross-hybridization to any other chromosomal regions. They were then tested on metaphase and interphase nuclei of tumors in which t(11;14)(q13;q32) translocations were identified by G-band karyotype analysis.

Normal (control) interphase nuclei show the expected two red and two green signals. In the tumor metaphase and interphase nuclei, the der(14) and der(11) chromosomes are identified by two co-localizing yellow signal. Thus, the two fusion signals observed confirm the presence of t(11;14)(q13;q32) translocation in the specimen analyzed.

Example 4

Detection of the t(8;14)(q24;q32) Translocation Associated with Burkitt's lymphoma I. Background As stated supra, this particular translocation has been found in 100% of Burkitt's lymphoma (BL) cases and in about 15% of other high grade B-cell lymphomas (Offit et al., 1991; 1992; Gaidano et al., 1993). The variant forms of this t(8;14) translocation, t(8;22)(q24;q11) and t(2;8)(p11;q24), have been identified in acute lymphoblastic leukemia, (Rabbitts 1994). The molecular consequence of the t(8;14)(q24;q32) translocation is the deregulation of the MYC proto-oncogene; this deregulation results from the replacement of the regulatory region of MYC gene by the heavy chain constant region of IGH. However, the locations of the breakpoints within the MYC gene are variable.

As shown in FIG. 7A, the MYC gene is organized in a centromere to telomere (5'-3') orientation on chromosome 8q24.1. It contains three exons (represented by open boxes) of which the coding region starts at nucleotide 16 of exon 2. The breakpoints (represented by vertical bars) are scattered over 300 kb of the genomic region on either side of the MYC gene in 8q24. The distribution of the breakpoints have been classified into three categories, class I, II, and III depending on the position within and outside the gene.

Breakpoints in the first exon or intron of MYC gene are in class I, breakpoints immediately upstream of the gene are in class II, and the distant breakpoints are in class III. The class I and II breakpoints are prevalent among the sporadic cases of BL, whereas the class III breakpoints are predominant among endemic African cases of BL. The class III breakpoints are dispersed over 300 KB upstream of the gene, whereas in variant translocations, the breakpoints are scattered over a region of 300 KB downstream of MYC gene (Zeidler et al., 1994). In some BL cases, the MYC gene is structurally altered while in other cases, it is structurally normal, with no change in the regulatory region (Showe et al., 1987). Given the dispersed nature of the breakpoints over several kilobases in the MYC region, the conventional methods for detecting the rearrangement, including G banding, Southern blotting and polymerase chain reaction (PCR), suffer from the technical limitations described supra.

The IGH locus is on chromosome 14q32 and is organized in a telomere to centromere orientation (FIG. 7A). It consists of a set of V, D, and J region segments that rearrange and join to create the active IGH V domain. The V region spans about 1100 kb upstream of the JH region. The D region lies between V and J segments. A more complex C region within about 200 kb contains 11 C region segments. Open boxes represent the position of all genes within IGH region. The t(8;14)(q24;q32) translocation breakpoints in the IGH gene occur directly adjacent to a Cμ region (represented by vertical bars).

II. Experimental

A. General

The general strategy for developing probes to be utilized to FISH assays to detect the t(8;14)(q24;q32) translocation is the same as that described in Example 1. Certain probe generation methods as provided herein are designed to prepare probes that bind to the segments of chromosomes 8 and 14 shown in FIG. 7A. Such probes can be utilized to conduct FISH assays in the signal segregation mode described herein. Two probes labeled with a green fluorophore are derived from the MYC gene at segments corresponding to the open bars shown (probes 1 and 2); another set of two probes labeled with a red fluorophore are derived from segments corresponding to the single hatched bars of the IGH gene (probes 3 and 4). Probes derived from the most proximal region of the translocation breaks do not segregate to the reciprocal chromosomes. Since the probe signal is not split, there is no loss of signal strength. In contrast, the probes derived from the region distal to the proximal breakpoints will segregate to the reciprocal chromosomes. These features provide for enhanced sensitivity.

Thus, when used to label chromosomes from normal and tumor nuclei, probes 1 and 2 together generate a green signal on chromosome 8, while probes 3 and 4 together generate a red signal on normal copies of chromosome 14. Probes 1 and 2 and probes 3 and 4 are close enough to one another on the chromosomes such that distinct signals are not obtained for each of the probes. The t(8;14)(q24;q32) positive nuclei, however, display two fusing or co-localizing green and red signals identifying the der(8) and der(14) chromosome due to the fact that signals are segregated to the rearranging chromosomes (see FIG. 7A).

B. Probe Generation

1. Probes for MYC Region

Probe 1: A BAC clone centromeric to all the three classes of breakpoints in the MYC region are generated using the following primers: F5'GGCAAATTG GTTTAAGTGGA3' (SEQ ID NO:9); R5'ACAGGGGAATGGTTAACTGG3' (SEQ ID NO:10) derived from WI-1120 (http://carbon.wi.mit.edu:). In nuclei carrying the translocation, this probe remains on the der(8) chromosome and generates a fusion or co-localizing signal in combination with the IGH probe from region 3 (FIG. 7A).

Probe 2: A BAC clone telomeric (Probe 2 in FIG. 7A) to all the breakpoints in the MYC gene is generated from the exon 2 region of MYC gene using the following primers: F5'-ATGCCCCTCAA CGTTAGCTTC3' (SEQ ID NO:11); R5'-CAGAGTCGCTGCTGGTGGT3' (SEQ ID NO:12). In the nuclei carrying the translocation, this probe segregates to the der(14) chromosome in all three class types of breakpoints (i.e., breakpoints involving the first intron, the first exon, or further centromeric region breakpoints) and results in a fusion or co-localizing signal with IGH probe from region 4 (see FIG. 7A).

2. Probes for IGH Region

Probe 3: A BAC clone covering the probe 3 region of the IGH gene (see FIG. 7A) is generated using the following primers derived from the sub-telomeric V region of the IGH gene to screen the BAC library: F-5'TGTTTGAAGAAGG-GAGTCGT3' (SEQ ID NO:13); R-5'CCCACTCCATGTCT-TCTGTT3' (SEQ ID NO:14). In the nuclei carrying the translocation, this probe segregates to the der(11) chromosome and generates a fusion or co-localizing signal in combination with probe 2.

Probe 4: A BAC clone covering the probe 4 region of the IGH gene (see FIG. 7A) is generated using the following primers derived from the Cα region to screen the library: F-5'CCACTCAGTGTG ACCTGGAGCGAA3' (SEQ ID NO:15); R-5'CTCCCCTGGCTTTTCTGG AACTGG3' (SEQ ID NO:16). In the nuclei carrying the translocation, this probe remains on the der(14) chromosome and generates a fusion or co-localizing signal in combination with the probe 2.

3. Screening of Human Genomic BAC Library and PCR Detection of the t(8;14)(q24:q32) Translocation Utilizing the primers just described, a human genomic BAC library is screened according to the screening methods set forth in Example 1. Clones so identified are subsequently purified of probes that contain repeat sequences, tested for chimerism, cross-hybridization, and signal strength, and then subjected to follow-up testing as further described in Example 1.

III. Results

The MYC and JH-Cα probes were tested on normal and tumor metaphase and interphase cells. The MYC probe was labeled with a green fluorophore and the IGH probe labeled with a red fluorophore. In normal interphase nuclei and tumor metaphase chromosomes, the probes exhibited unambiguous signals with no cross-hybridization to any other chromosomal regions. They were then tested on metaphase and interphase nuclei of tumors in which t(8;14)(q24;q32) translocations were identified by G banding.

Normal (control) interphase nuclei show the expected two red and two green signals. In the tumor metaphase and interphase nuclei, the der(14) and der(8) chromosomes are identified by two co-localizing yellow signal.

Example 5

Detection of the t(14;18)(q32;q21) Translocation in Follicular B-Cell Lymphoma

I. Background

The t(14;18)(q32;q21) translocation has been found to characterize about 60% of B-cell Non-Hodgkin's Lymphoma. The evidence also indicates that the translocation plays a significant role in indolent follicular and diffuse aggressive large cell lymphomas. It results in the juxtaposition of the BCL2 gene on chromosome 18 with the immunoglobulin heavy chain (IGH) gene on chromosome 14 resulting in over expression of BCL2 and neoplastic proliferation of B-cells. Approximately 25% of FL transform to DLCL (Offit and Chaganti, 1992). This translocation can be used as a diagnostic and prognostic marker.

The BCL2 gene is organized in a telomere to centromere (5'-3') orientation on chromosome band 18q21 (FIG. 6A). It covers approximately 400 kb of genomic region. It has three exons (open boxes). A large untranslated first exon is followed by a 220 bp intron I, a 581 bp exon 2, a 370 KB intron II, and a 5.4 KB untranslated exon III. The t(14;18)(q32;q21) translocation does not disrupt the BCL2 open reading frame that contains 239 amino acids. There are three reported breakpoint regions within the BCL2 gene. Approximately 70% of the breaks are clustered within a major breakpoint region (MBR) in the 3' noncoding region of the gene and approximately 25% are clustered in a minor cluster region (MCR) about 25 kb 3' of the gene (FIG. 6A). A third breakpoint with very low frequency has also been reported 5' to the other two breakpoints (Tsujimoto et al., 1987; Mikraki et al., 1991). The MBR, MCR, and 5' breakpoints in the BCL2 gene are not associated with differences in prognosis or clinical outcome.

As shown in FIG. 6A, the IGH locus is on chromosome 14q32 and is also organized in a telomere to centromere orientation. It consists of a set of V, D, and J region segments that rearrange and join to create the active IGHV domain. The V region spans about 1100 kb upstream of the JH region. The D region lies between V and J segments. A more complex C region within about 2000 kb contains 11 C region segments. The position of all genes within the IGH region is shown in FIG. 6A (open boxes). The t(14;18)(q32;q21) translocation breakpoints (vertical bars) in the IGH gene always occur within or directly adjacent to a JH segment (Cleary and Sklar, 1985; Tsujimoto et al., 1985; Bakhshi et al., 1985). The t(14;18)(q32;q21) translocation joins the 3' non coding region of the BCL2 to the JH segment of the IGH gene.

II. Experimental Design

A. General

The general strategy for developing probes to be utilized with FISH assays to detect the t(14;18)(q32;q21) translocation is the same as that described in Example 1. Certain probe generation methods are designed to prepare probes that bind to the segments of chromosomes 14 and 18 as shown in FIG. 6A. Such probes can be utilized to conduct FISH assays in the signal segregation mode described herein.

B. Probe Generation for Probes Shown in FIG. 6A

1. Primers from the Region Centromeric to BCL2 Gene:

Probe 1: A BAC clone covering the probe 1 region of the BCL2 gene was generated using the following primers from the region centromeric to BCL2 gene to screen the library: F-5'CTTGCCTCCTAAGCC AGTTG3' (SEQ ID NO: 17); R-5'TGGATTCATTTCTGATCCA3' (SEQ ID NO:18). This probe always remained on the der(18) chromosome in nuclei with translocations involving all three breakpoints to generate fusion or co-localizing signal resulting from the segregation of probe 3 from 14q32 to 18q21.

2. Primers from the Region Telomeric to BCL2 Gene:

Probe 2: A BAC clone covering the probe 2 region of the BCL2 gene was generated using primers from the region telomeric to BCL2 gene: F-5'TGGCCAGCAGCAGTGT-CAAATAG3' (SEQ ID NO:19); R-5'GGTGATCGTTAG-GACTCCCA3' (SEQ ID NO:20). This probe segregates to the der(14) chromosome in translocations involving all three breakpoints within the BCL2 gene and results in a fusion or co-localizing signal with probe 4.

3. Primers from the Region Telomeric to IGH-J Gene:

Probe 3: A BAC clone covering the probe 3 region of the IGH gene was generated using the following primers derived from the sub-telomeric region of chromosome 14q:F-5'TGTTTGAAGAAGGGAGTCGT3' (SEQ ID NO:21); R-5'CCCA CTCCATGTC TTCTGTT3' (SEQ ID NO:22). In the nuclei carrying this translocation, the probe segregates to the der(18) chromosome and generates a fusion or co-localizing signal in combination with probe 1 in t(14;18)(q32;q21) cases.

4. Primers from the Region Centromeric to IGH-J Gene

Probe 4: A BAC clone covering the probe 4 region of the IGH gene was generated using the following primers derived from the Cα region: F-5'CCCTGGACGCTTTTCAAATA3' (SEQ ID NO:23); R-5'GACTCAGGCAAGGACAAAGC3' (SEQ ID NO:24). In the nuclei carrying the translocation, this probe will remain on the der(14) chromosome and generate a fusion or co-localizing signal in combination with probe 2 from 18q21 region in t(14;18)(q32;q21) cases.

C. Screening of Human Genomic BAC Library and PCR Detection of the t(14;18)(q32;q21) Translocation A human genomic PAC library is screened utilizing the primers described in the preceding section according to the screening methods set forth in Example 1. Clones so identified are subsequently purified of probes that contain repeat sequences, tested for chimerism, cross-hybridization, and signal strength, and then subjected to follow-up testing as further described in Example 1.

III. Results

A. Probe Testing

The BCL2 and JH-Cα probe were tested on normal and tumor metaphase and interphase cells. The BCL2 probe was labeled with a green fluorophore and the IGH probe labeled with a red fluorophore. In normal metaphase and interphase nuclei they exhibited unambiguous signals with no cross-hybridization to any other chromosomal regions. They were then tested on metaphase and interphase nuclei tumors cells in which a t(14;18)(q32;q21) translocation was identified by G band karyotype analysis.

Normal (control) interphase nuclei show the expected two red and two green signals. In the tumor metaphase and interphase nuclei, the der (14) and der(18) chromosomes are identified by two co-localizing yellow color. In all cases, the translocation was identified both at metaphase and at interphase.

Example 6

Detection of the t(14;18)(q32;q21) Translocation in Follicular B-Cell Lymphoma using the Metasystems Image Scanning Platform I. Experimental Design A. General Probe DNA is prepared from BAC libraries and labeled using the direct label method. The labeled probes are then hybridized to cells derived from peripheral blood lymphocytes and scored using the Metasystems Image Scanning Platform.

B. MetaSystems Image Scanning Platform

Figure 12A:
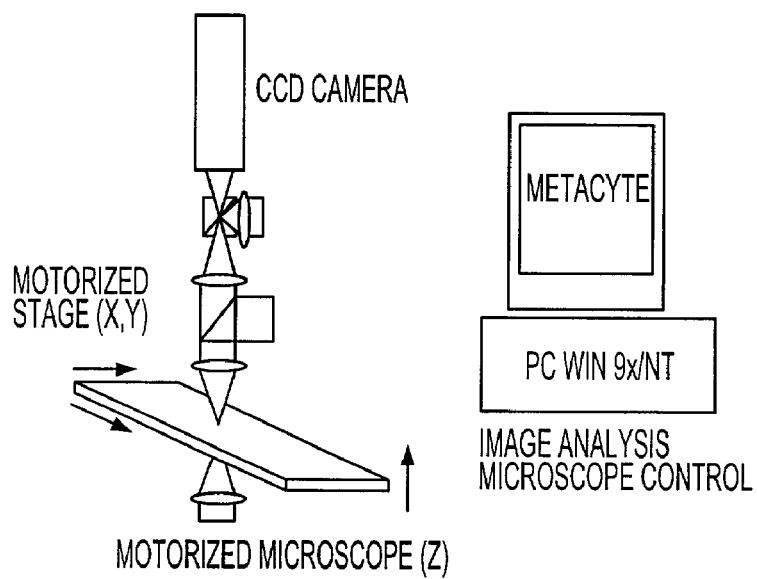
FIGS. 12A and 12B illustrate additional aspects of automated detection of chromosomal rearrangements.

Automated detection and counting of FISH signals in a large number of interphase nuclei is demanding both from a physics and an optical standpoint; the signals are small, contrast is often inconsistent, and 3-D analysis is required due to the thickness of the nuclei. The MetaCyte Automated Bio-Imaging System (Meta System Group, Inc., schematically depicted in FIG. 12A) was developed to fill the gap between flow cytometers, which are rapid but inflexible, and microscope based imaging systems for brightfield, which are not automated (Weber, 1992, Huber, 1995, Salomaa, 1997). The system consists of the following components: 1) Carl Zeiss Axio Plan 2 MOT fluorescence microscope, 2) scanning 8-position stage, 3) PC Pentium III Processor, 4) Jai camera, 5) camera interface, 6) stage control, 7) trackball and mouse, and 8) printer. The focus analysis begins with a slide set-up loaded onto the microscope. The slide is scanned as the stage is moved and the image is captured. Following scanning of the entire slide, a gallery is created. Based on the criterion set up for positive or negative, the image analysis either results in a positive or negative signal. If negative, the slide is rescanned for rare event analyses. If positive, there is a filter change for the appropriate fluorescent signal and 5-7 planes are captured and analyzed.

Standard slide preparation techniques are used (DAPI counterstain, same preparation techniques as used for manual interactive analysis). The system is easy to operate; no slide-specific calibration, adjustments of gain, offset or system parameters are required. There is walk away/overnight operation for 8 slides (standard or 100 slides with optional tray changer). Access to microscope and specimen is unrestricted. Adaptive detection algorithms and automatic exposure control function compensate for non-uniform staining conditions. Several markers can be detected simultaneously. The standard light source covers a wide spectrum from UV to near IR. Real time image gallery for interactive review, control and verification of scan results is available. Documentation, on screen review and relocation of any individual object is straightforward. 500 to 1000 cells per minute can be scanned for routine FISH spot counting (up to 1,000 cells per second for rare cell detection). Results from successive scans can be combined after re-staining the slide, e.g., for phenotype-genotype correlation.

C. Automated Slide Scanning

The scanning process includes several steps depicted in FIG. 11 and discussed in detail supra. Briefly, MetaCyte first establishes the focal plane of the nuclei at a reduced number of grid positions within the scan area. Subsequently, MetaCyte scans the slide with a speed of up to 4 images/sec. Within each camera field of view, the counterstain image (DAPI) is captured and analyzed to identify nuclei. Shape features can be available to reject clusters and damaged nuclei. If one or several nuclei are found within the camera field of view, the fluorescence filter (FITC, Rhodamine) is changed to acquire FISH signals. A series of images from different focal planes is captured and combined to an extended focus image (z-stack). Where probes labeled with different fluorochromes are hybridized, an extended focus image is generated for each fluorochrome/filter combination. The resolution is typically 0.35 µm (0.17 µm pixel size). For strong signals, a lower magnification can be used to increase scanning speed.

The MetaCyte apparatus comprises an adaptive spot counting algorithm, part of a classifier, which analyzes the image texture within the nuclei in each color plane and extracts over 20 features. It identifies spots based on their relative intensity, size, form factor and proximity. The user can select criteria and parameters the spots have to meet to be counted, including minimum or maximum size, minimum contrast, intensity, etc. In addition, spot co-localization in different color planes is analyzed to detect fusion signals. Classifiers are user trainable with a set of selected cells that reflect the morphometric characteristics of the current specimen. The minimum and maximum distance between red and green signals will be the determining criteria for the fusion or colocalizing signals in the automated platform. A scoring sheet is defined with a spreadsheet page for each cell that enables the review of scan results and markers for corrections of the automated interpretation by the human operator.

The system stores an image for each analyzed cell to be displayed in a gallery for user verification at the end of the analysis. Any of the measured features can be presented as histograms and scatter plots which can be used to select subpopulations for display, analysis or relocation, immediately after the scan, after having performed additional assays, or even in real time during the scanning procedure.

D. Materials and Methods

1. Probe Generation for Probes Shown in FIG. 11A a. BAC DNA Preparation

Mini-prep method: 5 ml overnight cultures for each clone are set up in LB medium containing 12.5 μg/ml of chloramphenicol and incubated at 37° C. for 14-16 hours with constant shaking. Cells are spun down in a microfuge tube and resuspended in 100 μl of chilled solution I (50 mM glucose, 20 mM Tris-Cl, pH 8.0, 10 mM EDTA, pH 8.0). 200 μl of freshly prepared solution II (0.2N NaOH, 1% SDS) is added and mixed gently and kept on ice. 150 μl of solution III (Potassium acetate, 3M potassium and 5 M acetate) is added and mixed gently. The tubes are spun and the supernatant collected in a new microfuge tube and mixed with 1 ml of 100% ethyl alcohol at room temperature. The tubes are spun for 10 minutes at room temperature and the supernatant discarded. The pellet is washed in 70% ethanol, air-dried and resuspended in 30 μl of TE. A 5 μl aliquot is then tested on agarose gel.

Alternatively, the BCL2 and JH-CA probes for the present example can take the form of those described for use in example 5, supra.

b. Probe Labeling

All the probes included for FISH analysis are labeled by nick translation (GIBCO-BRL) according to manufacturer's instructions. Modified nucleotides conjugated with direct fluorochromes, fluorescein 12-dUTP and Rhodamine 5-dUTP, (Sigma, Mo.) are utilized to obtain green and red color signals, respectively. Following labeling reactions, the unincorporated nucleotides are separated by passing through Sephadex G-50 columns. The probe DNA is precipitated with absolute alcohol and dissolved in hybridization mixture (50% formamide, 2×SSC, 10% dextran sulphate, 1% Denhardt's solution) and stored at −20° C. until further use. Approximately 200 ng of each probe is used for hybridization.

2. Preparation of Nuclei from Patients: (Verma and Babu 1989)

Heparinized peripheral blood or bone marrow samples collected from individuals suspected of suffering from Follicular B-Cell Lymphoma are used for chromosomal preparation. Briefly, 0.5 to 1.0 ml of peripheral blood is inoculated to 10 ml of RPMI-1640 medium supplemented with 15% fetal bovine serum and 1% L-glutamine and streptopenicillin. 0.2 ml of (1 mg/ml) phytohemagglutinin is then added and the cultures incubated at 37° C. for 72 hours. One hour prior to harvest, 0.2 ml (10 μg/ml) of colcemid solution is added and incubated for 1 hour at 37° C. The cultures are harvested by treating cells with pre-warmed hypotonic solution (0.075M KCl) for 15-20 minutes and fixed with 3:1 methanol acetic acid fixative. Standard air-dried slides will be prepared.

3. Hybridization of Probes to Chromosomes

Prior to hybridization, slides containing chromosomes are pretreated by incubating with 2×SSC for one hour at 37° C. followed by passing through 70%, 80% and 100% alcohol for dehydration. The slides are denatured at 70° C. in denaturing solution (70% formamide, 2×SSC) and passed through cold ethanol series. Simultaneously, the probes are denatured and placed on slides and hybridized overnight at 37° C. Post hybridization washes are performed at 45° C. in prewarmed 2×SSC solution twice, followed by one room temperature wash in 2×SSC. The slides are then counterstained with anti-fade solution containing 4', 6'-diamidino-2-phenylindole dihydrochloride (DAPI) (Vysis, Downers Grove, Ill.).

4. Slide Analysis a. Manual Image Analysis

The cells are scored directly under microscope using triple band pass filter for the simultaneous visualization of red, green and blue colors. The green and red fluorescence intensities of the hybridization signals and DAPI staining patterns are captured with a cooled charge-coupled device camera (CCD) attached to a Olympus BX60 microscope and processed using ISIS software (Metasystems) for recording purposes.

Scoring criteria are determined by first defining the diagnostic threshold of the method for detecting t(14;18)(q32;q21). For each set of control and tumor specimens, at least 300 nuclei are analyzed following stringent criteria. In control specimens, cells are scored as normal when two separate green and red signals are observed. For closely placed red and green signals, the distance between each signal is at least twice the size of one signal, which will be considered a normal pattern. Similarly, a fusion or co-localizing signal is scored when the distance between red and green signals is less than one signal size.

In tumor specimens, the same stringent criteria is followed as when normal cells are encountered. Tumor cells are scored positive only when two clear fusion signals and single red and green signals are observed. A comparison with manual slide evaluation methods is periodically performed to assess the efficiency of the system including the speed and the ability to correctly measure and count.

Cells carrying t(14;18) are identified by the presence of two fusion signals and one green and one red signal and the normal cells are identified with two separate green and red signals. In this method, the following signal patterns are scored for positive and negative cells:

1) cells with two fusion, one green and one red signal—t (14;18)(q32;q21) carrying cells 2) cells with one fusion, one green, and one red signal—normal cell with false positive signal 3) two separate green and two separated signal—normal cell 4) two fusion signals—normal cell with two false positive signals b. Automated Slide Scanning Each slide is tested for signal quality and contrast and have an area of suitable hybridization marked before scanning. At least one test slide from each series is scanned with different sensitivity settings. To ensure accurate scoring, automated results are periodically evaluated by a comparison to the manual image analysis describes supra. A limit of 1,000 cells is set for all slides where results are compared with manual slide evaluation. After each scan all included cells as displayed in the image gallery are reviewed. They are scored first using the image gallery only using the same scoring criteria detailed for manual image analysis, supra.

For blood samples deficient in peripheral B-cells, the sample is pre-enriched by sorting out cells expressing B-cell surface markers using either magnetic separation or FACS.

II. Results

Figure 12B:
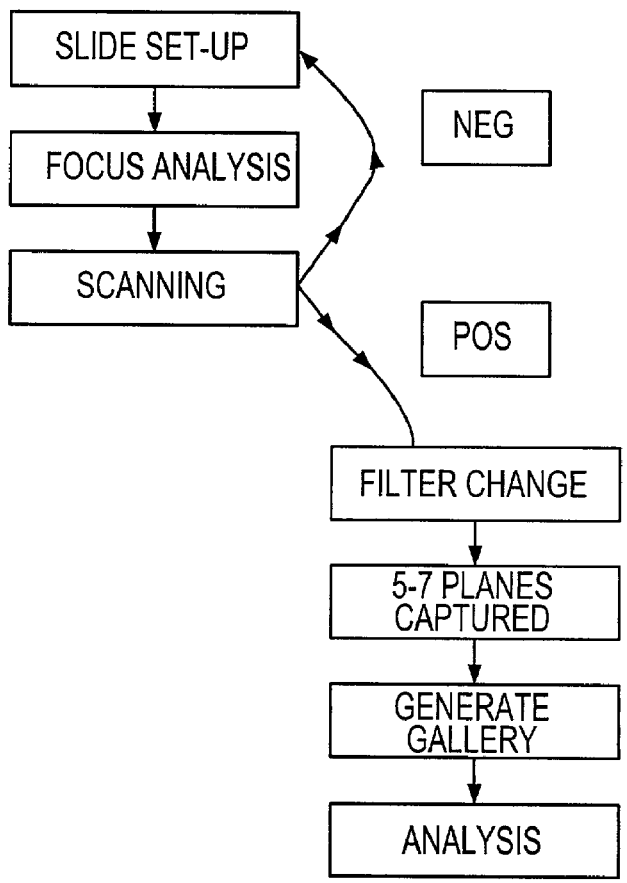

The BCL2 and JH-Cα probe were tested on normal and tumor metaphase and interphase cells. The BCL2 probe was labeled with a green fluorophore and the IGH probe labeled with a red fluorophore. Automatic scanning of peripheral blood samples was performed, creating a gallery of tentatively translocation positive images and a scoring sheet comprised of statistical data for the sample. In this manner, the Metacyte system affords the clinician the opportunity to review any putatively positive results through a manual evaluation of images stored in the gallery. FIG. 11B-11E depicts one such result. The steps in the process leading to the result are detailed below and illustrated in the flow diagram of FIG. 12B.

FIG. 11B depicts a DAPI-stained nucleus as imaged using the Metacyte system. An aspect of the system is that it can detect shape features of DAPI-stained nuclei, allowing for rejection of clusters and damaged nuclei.

The system first scans the system looking for suitable DAPI stained nuclei for analysis. Once found, a fluorescence filter (e.g., FITC, Rhodamine) is changed to acquire the signal from one set of S-FISH probe signals. FIG. 11C illustrates the use of a filter which removes the probe signals generated by probes 3 and 4, allowing for the detection of the signals generated by probes 1 and 2. Only three light grey spots can be seen. These three light grey spots correspond to the untranslocated copy of chromosome 18 (binding both probes 1 and 2), and the signals generated by probes 1 and 2 on the respective translocated derivative chromosomes. The system automatically changes its focal plane through the sample from 5 to 7 times, storing an image of the sample at each focal plane. This technique ensures accurate diagnosis by producing a series of images defining the sample in three dimensions.

The system then undergoes a second fluorescence filter change to pick up the second set of signals, an image of which is presented in FIG. 11D. Only three dark grey spots can be seen. These three dark grey spots correspond to the untranslocated copy of chromosome 14 (binding both probes 3 and 4), and the signals generated by probes 3 and 4 on the respective translocated derivative chromosomes. Again, the system automatically changes its focal plane through the sample from 5 to 7 times, storing an image of the sample at each focal plane.

The system then takes one final set of images while changing focal planes with a filter in place which cuts out the DAPI signal but allows the signals from both sets of FISH probes to pass. An image from this set is depicted in FIG. 11E.

Using both interphase and metaphase cells, the automated methods accurately categorized cells as positive or negative for the t(14;18)(q32;q21) translocation. This example illustrates the power of the methods described herein to produce clear, unambiguous FISH patterns from both tumor and normal cells, suitable for automated image analysis. These techniques facilitate the rapid processing of clinical samples, making diagnosis of Follicular B-Cell Lymphoma, and other NHL's, routine.

Example 7

Detection of the t(9;22)(q34.1;q11.2) Translocation and Associated Deletions Common to Chronic Myeloid Leukemia (CML)

I. Background

The BCR/ABL oncogene is expressed at all stages of CML. The chronic phase is characterized by the expansion of terminally differentiated neutrophils and as the disease progresses and enters the acute phase (blast crisis) it is characterized by maturation arrest with expansion of undifferentiated myeloid or lymphoid progenitor cells. During disease progression additional genetic and molecular changes have been acquired which forms the basis for resistance to treatment, particularly ST1571 (Druker et al., 2001; Gorre et al., 2001). Although several sporadic incidences of secondary chromosomal changes have been reported in CML their clinical correlation has not been clearly established as it has been shown for deletions on the rearranged chromosome. It has also been shown that the deletion on der(9) chromosome are known to occur at the time of t(9;22)(q34.1;q11.2) translocation event itself (Sinclair et al., 2000). The strong association of deletions with altered prognosis indicates the importance to detect the deletions along with translocation. In addition to chemotherapy, allogenic bone marrow transplantation (BMT) and peripheral blood stem cell transplantation are also therapies of choice for CML because of their ability to attain sustained suppression or elimination of CML cells. However, regardless of the different modalities in therapy a significant proportion of CML cases relapse after bone marrow transplants. These treatments require regular follow-up for recurrence of cancer in bone marrow and blood. The most definitive method currently in use for this purpose is karyotype analysis by G-banding. Although this method is precise, it is labor intensive and will not detect small deletions associated with CML. In addition, 50% of follow-up specimens do not yield results due to hypocellularity of marrow samples and poor cell proliferation in vitro. Other methods of translocation detection include Southern blotting; PCR and RT-PCR to detect gene rearrangements and fusion transcripts, but these methods have sensitivity and specificity issues. For use in detecting rearrangements, Southern blotting requires the presence of at least 5-10% tumor cells. PCR is difficult to quantitate and prone to false positive results from amplification of DNA sequences in dead tumor cells or in free DNA from lysed cells still present in the specimen. Quantitative RT-PCR is a new method of choice for monitoring disease after treatment but this method is not suitable for deletion detection. The strong association of CML deletions with treatment outcome warrants the need for the development of sensitive FISH probes to evaluate the presence of deletions at diagnosis. Molecular methods are laborious and time consuming for such analysis.

II. Probe Design and Construction

PCR screening of a human genomic BAC library (Incyte Genomics, St. Louis, Mo.) is performed to isolate clones covering the BCR and ABL gene regions. The primers for the screen are selected using the NCBI database sequence information. Suitable BAC clone sequences for FISH probe construction are selected. Criteria for sequence selection in this particular example comprise ensuring that the selected sequences span about 500 kb on either side of all known t(9;22)(q34.1;q11.2) translocational breakpoints associated with CML (although shorter sequences can be used as an alternative).

A. Probe Labeling

For F-FISH analysis the centromeric region probes for BCR and ABL genes are labeled with Cyanin-5-dUTP (Yellow) and Texas red dUTP (Red) (PerkinElmer Life Sciences, Boston, Mass.) respectively, and the telomeric region probes for BCR and ABL genes are labeled with Fluorescein 12-dUTP (Green) and Coumarin-5-dUTP (Blue) (PerkinElmer Life Science, Boston, Mass.) respectively. For two color FISH analysis the ABL and BCR region probes are labeled with Fluorescein 12-dUTP (Green) and Texas Red—dUTP (Red) labels respectively.

The recipe for the labeling reaction consists of; a total of 50 ng each of four-color (F-FISH) probe dissolved in a hybridization buffer containing 50% Formamide, 2×SSC, 10× Dextran sulphate and 1% Denhardt's solution. Slides carrying chromosomal samples for analysis are denatured at 75° C. for 2 minutes and dehydrated in 70%, 80% and 100% ethanol followed by air-drying. The probe mixture is denatured at 75°

C. for 8 minutes, applied to the slides and incubated overnight at 37° C. Post hybridization washes are then preformed in 50% formamide, 2×SSC at 45° C. (2×) for 10 minutes each and washed twice in 2×SSC (45° C.). Finally, slides are briefly rinsed in distilled water, air dried and counterstained with DAPI.

Techniques for hybridizing probes to chromosomes are described in Example 6 and are commonly known in the art.

B. Image Scanning

Alternative scanning and analysis techniques described elsewhere in this application are also amenable to the F-FISH analysis described in this example and may be substituted for those described here.

FISH images are captured and analyzed using a mega pixel JAI-CCD camera attached to Axioplan-21E (ZEISS, Germany) microscope controlled by In situ Imaging System (ISIS) image processing software (Metasystems Group, Belmont Mass.). Analysis may be performed manually, or the process can be automated through the MetaSystems Image Scanning Platform described in Example 6

III. Results

Probes developed for performing the signal segregation analysis are labeled by the two-label system to conduct a preliminary screening of a panel of 70 unselected CML samples. Of the 70 cases; 59 were known to have standard t(9;22)(q34.1;q11.2) translocation, 8 possessed variant translocations, two cases displayed the Ph chromosome and one case showed amplification of BCR/ABL fusion region. Of the 70 cases, 59 had t(9;22)(q34.1;q11.2), 8 had variant translocations, two cases showed additional Ph chromosomes and K562 cell line with high level amplification of BCR/ABL fusion region. Of the 59 cases with t(9;22)(q34.1;q11.2), 12 cases were identified as having deletions, and 4 of the 8 cases with variant translocations were also found to have a deletion. Of the 12 cases with t(9;22)(q34.1;q11.2), 4 cases had deletions of both the BCR and ABL regions on der(9) chromosome, and 1 case had a deletion of the ABL and BCR regions on der(22) chromosome. In two cases deletion of the BCR region on der(9) was observed, and deletion of ABL sequences alone was observed in 4 cases. In one case, deletion of the ABL region on der(22) was observed. The incidence of deletions was higher in cases with variant translocations (50%) than in the cases with the t(9;22)(q34.1;q11.2) translocation (20%). Of the 8 cases with variant translocations, 4 cases were found to have deletions. These included deletions in regions of BCR (1 case), ABL (1 case) and both ABL and BCR (2 cases). In specimens with a typical signal patterns metaphase cells were analyzed to confirm the origin of the chromosome suffering a deletion and those chromosomes undergoing variant translocations.

From the preliminary screening, specimens for a) normal, b) standard t(9;22)(q34.1;q11.2) translocation, c) deletion on der(9), d) deletion on der(22), and e) variant translocation were selected and subjected to F-FISH analysis. The signal patterns obtained from the F-FISH analysis are schematically depicted in FIG. 4.

As shown in FIG. 4A, in normal interphase nuclei, the two copies of chromosome 9 and two copies of 22 are identified unambiguously by a two-label signal for each chromosome such that there a four distinct labels. Similarly, in tumor cells (FIG. 4B), in addition to one copy each of normal 9 and 22, the der(9) and der(22) are each identified by entirely different two-label signal patterns unique to the respective chromosomes. This four-color F-FISH approach thus allows interpretation of the various signal patterns found in analysis of chromosomal rearrangements associated with CML through analysis of interphase cells alone.

The studies described in the foregoing examples establish that clear and unambiguous signals can be obtained utilizing a segregated signal approach to detect translocations. While analyses utilizing such signals can be conducted with two probes that together recognize one of the two derived chromosomes, by using four probes (two for each chromosome that together flank the breakpoint) one can simultaneously detect both normal and translocated chromosomes.

Example 8

Removal of Repeat Sequences from a BAC Clone

I. Step 1: Size Estimation by Pulsed Field Gel Electrophoresis (PFGE)

100 ng of BAC DNA was digested with NotI restriction enzyme to release the insert and vector DNA as separate fragments, which were resolved by pulsed field gel electrophoresis using the CHEF DR II apparatus (BIORAD). The following gel run parameters were used for PFGE: 0.5×TBE buffer recirculating at 14° C., 1% pulsed field certified agarose, initial switch time 1 sec., final switch time 6 seconds at 6 volts/cm, with an angle at 120° for 18 hours. Appropriate size markers were used. Following electrophoresis, the gel was stained with ethidium bromide for 15 minutes and visualized under a UV transilluminator for documentation. Two bands were identified, one corresponding to insert (200 kb) and the smaller fragment corresponding to the vector (7.0 kb).

II. Restriction Digestion of BAC Clone 543:

Initially the BAC DNA was digested with EcoRI and HindIII. These digests yielded many larger fragments in the size range of 6-20 kb and few smaller fragments. Southern hybridization with radiolabeled Cot-1 DNA probe showed very few smaller fragments free of repeat sequences. Thus, PstI was selected for subcloning the BAC inserts, because PstI yielded fragments in the size range of 500 bp to 6 kb and also many fragments were identified to be free of repeat sequences. The clone 543 selected an example here was identified with approximately 40 fragments, using PstI digestion, in the size range of 200 bp-6 kb.

III. Subcloning

One microgram of BAC DNA was digested with PstI to completion. Similarly p-Bluscript SK-plasmid vector was also digested with PstI. Dephosphorylation of the digested plasmid vector with calf intestinal alkaline phosphatase (CIAP) was done prior to ligation to the insert DNA. The dephosphorylated vector DNA was ethanol precipitated and resuspended in TE buffer. For ligation, the insert and vector DNA in the ratio of 2:1(insert:vector) were mixed and the reaction was continued at 4° C. overnight (Shotgun ligation). The ligation mixture was transformed into competent cells of XL1-Blue MRF' host bacteria and plated on selective media containing tetracycline-chloramphenicol to select for colonies that contained the inserts. Ninety-nine white bacterial colonies were selected and grown in a 5 ml culture overnight.

IV. Preparation of Mini Prep DNA

DNA from the 5 ml overnight culture was prepared by a standard alkaline lysis method (Sambrook and Russel, 2001). Plasmid DNA was digested with PstI and electrophoresis was performed to identify DNA samples with inserts. Ninety of the selected colonies were found to contain inserts of varying size.

V. Preparation of Glycerol Stock

Glycerol stock for all the colonies with inserts were made by mixing 800111 of bacterial culture and 200 µl of 80% glycerol and stored at −80° C.

VI. Identification of Repeat Free Clones

All the insert-containing clones were size selected and run on an agarose gel. The DNA on the agarose gel was transferred to nylon membrane and hybridized with radiolabeled ($P^{32}$) Human Cot-1 DNA (Invitrogen, Rockvill, Md.). Of all the 90 clones with inserts, all 40 of the unique sized clones were identified. Among the 90 clones hybridized with radiolabled probe, only 28 clones were found to contain repeat sequences. The rest of the clones were free of repeats. Among all the repeat free clones, unique size clones were selected for preparation of large scale DNA to be used as a probe for FISH hybridization.

The same approach can be used to select the repeat free fragments from each BAC clone selected for a translocation detection probe.

It is understood that the examples and embodiments described herein are for illustrative purposes only and that various modifications or changes, such as utilization of individual colors for each probe, in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

REFERENCES

Bakhshi, A., Jensen J. P., Goldman P., Wright J J, McBride O W, Epstein A L and Korsmeyer S J. Cloning the chromosomal breakpoint oft(14;18) human lymphomas: Clustering around JH on chromosome 14 and near a transcriptional unit on 18. Cell 41:889, 1985

Banks P M, Chan J, Cleary M L, Delsol G, De Wolf-Peeters C, Gatter K, Grogan T M, Harris N L, Isaacson P G, Jaffe E S, Mason D, Pileri S, Ralfliaer E, Stein H, Warnke, R A: Mantle cell lymphoma. A proposal for unification of morphologic, immunologic, and molecular data. Am J Surg Pathol 16:637, 1992

Chaganti R S, Nanjangud G, Schmidt H, Teruya—Feldstein J. Recurring chromosomal abnormalities in non-Hodgkin's lymphoma: biologic and clinical significance. Semin Hematol, 37(4):396-411, 2000.

Chen, W, Palanisamy, N, Schmidt, H., Teruya-Feldstein, J, Jhanwar, S. C, Zelenetz, A. D, Houldsworth, J, and Chaganti, R. S. K. Deregulation of FCG2RB expression by 1q21 rearrangements in follicular lymphomas. Oncogene (In Press)

Cleary M L and Sklar J. Nucleotide sequence of a t(14;18) chromosomal breakpoint in follicular lymphoma and demonstration of a breakpoint cluster region near a transcriptionally active locus on chromosome 18. Proc Natl Acad Sci USA 82, 7439-7443, 1985

Coignet L J, Schuuring E, Kibbelaar R E, Raap T K, Kleiverda K K, Bertheas M F, Wiegant J, Beverstock G, Kluin P M: Detection of 11q13 rearrangements in hematologic neoplasias by double-color fluorescence in situ hybridization. Blood 87:1512, 1996

Colleoni, G W B, Jhanwar S C, Ladanyi M, Chen B. Comparison of a multiplex reverse transcriptase-polymerase chain reaction for BCR-ABL to fluorescence in situ hybridization, southern blotting, and conventional cytogenetics in the monitoring of patients with ph1-positive leukemias. Diagnostic Molecular Pathology 9(4):203-20, 2000.

Cotter F, Price C, Zucca E and Young B D. Direct sequence analysis of the 14q+ and 18q− chromosome junctions in follicular lymphoma. Blood 76:1, 131-135, 1990 de Boer C J, Loyson S, Kluin P M, Kluin-Nelemans H C, Schuuring E, van Krieken J H: Multiple breakpoints within the BCL-1 locus in B-cell lymphoma: rearrangements of the cyclin D1 gene. Cancer Res 53:4148, 1993 de Klein A, van Kessel A G, Grosveld G, Bartram C R, Hagemeijer A, Bootsma D, Spurr N K, Heisterkamp N, Groffen J, Stephenson J R. Nature 23; 300(5894):765-7, 1982.

Dewald G W, Wyatt W A, Juneau A L, Carlson R O, Zinsmeister A R, Jalal S M, Spurbeck J L, Silver R T Highly sensitive fluorescence in situ hybridization method to detect double BCR/ABL fusion and monitor response to therapy in chronic myeloid leukemia. Blood 91:3357-65, 1998.

Druker B J, Sawyers C L, Kantarjian H, Resta D J, Reese S F, Ford J M, Capdeville R, Talpaz M. Activity of a specific inhibitor of the BCR-ABL tyrosine kinase in the blast crisis of chronic myeloid leukemia and acute lymphoblastic leukemia with the Philadelphia chromosome. N Engl J Med 2001 Apr. 5; 344(14):1038-42

Dyomin V G, Palanisamy N, Lloyd K O, Dyomina K, Jhanwar S C, Houldsworth J, Chaganti R S K. MUC1 is activated in a B-cell lymphoma by the t(1;14)(q21;q32) translocation and is rearranged and amplified in B-cell lymphoma subsets. Blood. 15; 95(8):2666-71, 2000.

Elmaagacli A H, Beelen D W, Opalka B, Seeber S, Schaefer U W. The amount of BCR-ABL fusion transcripts detected by the real-time quantitative polymerase chain reaction method in patients with Philadelphia chromosome positive chronic myeloid leukemia correlates with the disease stage. Ann Hematol, 79:424-431, 2000.

Faderl S, Talpaz M, Estrov Z, O'Brien S, Kurzrock R, Kantarjian H M. The biology of chronic myeloid leukemia. N Engl J Med 341:164-72, 1999.

Gaidano G, Dalla-Favera R: Biologic and molecular characterization of non-Hodgkin's lymphoma. Curr Opin Oncol 5:776, 1993

Galiege-Zouitina S, Collyn-d Hooge M: Denis C, Mainardi A, Hildebrand M-P, Tilly H, Bastard C, Kerckaert J-P,: Molecular cloning of a t(11;14)(q13;q32) translocation breakpoint centromeric of the BCL1-MTC. Genes Chromosome Cancer 11:246, 1994

Gorre M E, Mohammed M, Ellwood K, Hsu N, Paquette, Rao P N, Sawyers C L. Clinical resistance to STI-571 cancer therapy caused by BCR-ABL gene mutation or amplification. Science express, Jun. 21, 2001.

Hajemeijer A. Chromosomal abnormalities in CML. In: Balliere's Clinical Haematology Vol 1, No 4 London: Balliere Tindall, 1987: 963-81.

Harris N L, Jaffe E S, Stein H, Banks P M, Chan J K, Cleary M L, Delsol G, De Wolf-Peeters C, Falini B, Gatter K C, Grogan T M, Isaacson P G, Knowles D M, Mason D Y, Muller-Hermelink, H-K, Pileri S A, Piris M A, Ralfkiaer E, Warnke R A. A revised European-American classification of lymphoid neoplasms: a proposal from the International Lymphoma Study Group. Blood 84:1361, 1994

Hatzivassiliou G, Miller I, Takizawa J, Palanisamy N, Rao P H, Lida S, Tagawa S, Russo J, Neri A, Cattoretti G, Clynes R, Mendelsohn C, Chaganti R S K, Dalla-Favera R: IRTA1 and IRTA2, novel immunoglobulin superfamily receptors expressed in B cells and involved in chromosome 1q21 abnormalities in B cell malignancy. Submitted to Immunity, November 2000

Heim S, and Mitelman F. Cancer cytogenetics. Chromosomal and molecular genetic aberrations of tumors cells. Second edition. A John Wiley & Sons, Inc. Publication, 1995

Heisterkamp N, Stephenson J R, Groffen J, Hansen P F, de Klein A, Bartram C R, Grosveld G. Localization of the c-abl oncogene adjacent to a translocation break point in chronic myelocytic leukemia. Nature 306:239-42, 1983.

Huber, R, U. Kulka, T. Lörch, H. Braselmann, M. Bauchinger. Automated metaphase finding: an assessment of the efficiency of the METAFER2 system in routine mutagenicity assay, Mutation Research, 334, 97-102, 1995

Iida S, Rao P H, Palanisamy N, Hibshoosh H, Butler M, Louie D C, Dyomin V, Ohno H, Chaganti R S, Dalla-Favera R. The t(9;14)(p13;q32) chromosomal translocation associated with lymphoplasmacytoid lymphoma involves the PAX-5 gene. Blood. 1; 88(11):4110-7, 1996

Kamentsky et al., "Methods for Automatic Multiparameter Analysis of Fluorescence in situ Hybridized Specimens with a Laser Scanning Cytometer", Cytometry 27:117-125, 1997

Kolomietz E, Al-Maghrabi J, Brenna S, Karaskova J, Minkin S, Lipton J, Squire J A. Primary chromosomal rearrangements of leukemia are frequently accompanied by extensive submicroscopic deletions and may lead to altered prognosis. Blood 97: 3581-3588, 2001.

Lin F, van Rhee F, Goldman J M, Cross N C Kinetics of increasing BCR-ABL transcript numbers in chronic myeloid leukemia patients who relapse after bone marrow transplantation. Blood 87:4473-8, 1996.

Marcucci G, Livak K J, Bi W, Strout M P, Bloomfield C D, Caligiuri M A. Detection of minimal residual disease in patients with AML1/ETO-associated acute myeloid leukemia using a novel quantitative reverse transcription polymerase chain reaction assay. Leukemia12:1482-9, 1998.

Maurer J, Janssen J W, Thiel E, van Denderen J, Ludwig W D, Aydemir U, Heinze B, Fonatsch C, Harbott J, Reiter A, et al. Detection of chimeric BCR-ABL genes in acute lymphoblastic leukemia by the polymerase chain reaction. Lancet 337:1055-8, 1991.

Melo J V. The diversity of BCR-ABL fusion proteins and their relationship to leukemia phenotype. Blood 88:2375-84, 1996. Mills K I, Sproul A M, Leibowitz D, Burnett A K. Mapping of breakpoints, and relationship to BCR-ABL RNA expression, in Philadelphia-chromosome-positive chronic myeloid leukemia patients with a breakpoint around exon 14 (b3) of the BCR gene. Leukemia 5,937-41, 1991.

Meusers P, Engelhard M, Bartels H, Binder T, Fulle H H, Gorg K, Gunzer U, Havemann K, Kayser W, Konig E,: Multicentre randomized therapeutic trial for advanced centrocytic lymphoma: anthracycline does not improve the prognosis. Hematol Oncol 7:365, 1989

Mikraki V, Ladanyi M, Chaganti R S K. Structural alterations in the 5' region of the BCL2 gene in follicular lymphomas with BCL2-MBR or BCL2-MCR rearrangements. Genes Chromosomes Cancer 3:117, 1991

Mohr B, Bornhaeuser M, Ehninger G, Freiberg-Richter J, Kroschinsky F, Mohm J, Naumann R, Platzbecker U, Prange-Krex G, Thiede C. Problems with interphase fluorescence in situ hybridization in detecting BCR/ABL-positive cells in some patients using a novel technique with extra signals. Cancer Genetics and Cytogenetics 1272:111-117.

Nowell P C, Hungerford D A. A minute chromosome in human chronic myelogenous leukemia. Science, 132:1497-9. 1960

Motokura T, Arnold A: PRAD1/CyclinD1 proto-oncogene: Genomic organization, 5'DNA sequence and sequence of a tumor-specific rearrangement breakpoint. Genes Chromosome Cancer 7:89, 1993

Offit K, and Chaganti R S K: Chromosomal aberrations in non-Hodgkins's lymphoma. Biologic and clinical correlations. Hematol/Oncol Clin North Am 5:853-869, 1992

Offit K: Chromosome analysis in the management of patients with non-Hodgkin's lymphoma. Leuk Lymphoma 7:275, 1992

Pane F, Frigeri F, Sindona M, Luciano L, Ferrara F, Cimino R, Meloni G, Saglio G, Salvatore F, Rotoli B Neutrophilic-chronic myeloid leukemia: a distinct disease with a specific molecular marker (BCR/ABL with C3/A2 junction). Blood 88:2410-4, 1996.

Parker S L, Tong T, Bolden S, Wingo P A. Cancer statistics, 1996. CA Cancer J. Clin., 446: 5-27, 1996

Poetsch M, Weber-Matthiesen K, Plendl H-J, Grote W, Schlegelberger B. Detection of the t(14; 18) chromosomal translocation by interphase cytogenetics with yeast artificial chromosome probes in follicular lymphoma and normeoplastic lymphoproliferation. J Clin Oncol 14, 3963-969, 1996

Rabbitts T H: Chromosomal translocations in human cancer. Nature 372:143, 1994

Raffeld M, Jaffe E S: bcl-1, t(11;14), and mantle cell-derived lymphomas. Blood 78:259, 1991

Rimokh R, Berger F, Comillet P, Wahbi K, Rouault J P, Ffrench M, Bryon P A, Gadoux M, Gentilhomme O, Germain D, MagaudJ-P: Break in the BCL1 locus is closely associated with intermediate lymphocytic lymphoma subtype. Genes Chromosomes Cancer 2:223, 1990

Rimokh R, Berger F, Delsol G, Charrin C, Bertheas M F, Ffrench M, Garoscio M, Felman P, Coiffier B, Bryon P A, Rochet M, Gentilhomme O, Germain D, Magaud J P: Rearrangement and overexpression of the BCL-1/PRAD-1 gene in intermediate lymphocytic lymphomas and in t(11q13)-bearing leukemia's. Blood 81:3063, 1993

Rimokh R, Berger F, Delsol G, Digonnet I, Rouault J P, Tigaud J D, Gadoux M, Coiffier B, Bryon P A, Magaud J P: Detection of the chromosomal translocation t(11;14) by polymerase chain reaction in mantle cell lymphomas. Blood 83:1871, 1994

Rowley J D. A new consistent chromosomal abnormality in chronic myelogenous leukemia identified by quinacrine fluorescence and giemsa staining. Nature, 243:290-1, 1973.

Salomaa S, Sevan'kaev A V, Zhloba A A, Kumpusalo E, Makinen S, Lindholm C, Kumpusalo L, Kolmakow S and Nissinen A. Unstable and stable chromosomal aberrations in lymphocytes of people exposed to Chernobyl fallout Bryansk, Russia, Int. J. Radiat. Biol., Vol. 71, No. 1, 51-59, 1997

Sambrook J and Russel D W. Molecular Cloning. A laboratory Manual. Cold Spring Harbor Laboratory Press (2001)

Schwartz D C and Cantor C R, Separation of yeast chromosome size DNAs by pulsed field gradient gel electrophoresis. Cell 37:67-75.

Shiramizu B, Magrath I: Localization of breakpoints by polymerase chain reactions in Burkitt's lymphoma with 8;14 translocations. Blood 75:1848, 1990

Showe L C, Moore R C, Erikson J, Croce C M: MYC oncogene involved in a t(8;22) chromosome translocation is not altered in its putative regulatory regions. Proc Natl Acad Sci U S A 84:2824, 1987

Telenius H, Carter N P, Bebb C E, Nordenskjold M, Ponder B A, Tunnacliffe A. Degenerate oligonucleotide-primed PCR: general amplification of target DNA by a single degenerate primer. Genomics, 13 (3):718-25, 1992.

The ACT cytogenetics laboratory manual. Second Edition. Editor Margaret J B. Raven Press, 1991

Tkachuk, D C, Westbrook, C A, Andreeff M, Dondon, T A Cleary M L, Suryanarayana K, Homge M, Redner A, Gray J, Pinkel D. Detection of bcr-abl fusion in chronic myelogenous leukemia by insitu hybridization Science 250: 559-562, 1990

Tsujimoto Y, Yunis J, Onorato-Showe L, Erickson J, Nowell P C & Croce C M: Molecular cloning of chromosomal breakpoint of B-cell lymphomas and leukemia's with the t(11;14) chromosome translocation. Science 224: 1403, 1984

Tsujimoto Y, Gorham J, Cossman J, Jaffe E, and Croce C M. t(14;18) chromosome translocations involved in B-cell neoplasms result from mistakes in VDJ joining. Science 229, 1390-1393, 1985b Tsujimoto Y, Bashir M M, Givol I, Cossman J, Jaffe E, Croce C M: DNA rearrangements in human follicular lymphoma can involve the 5' or the 3' region of the bcl-2 gene. Proc Natl Acad Sci 84,:1329, 1987

Vaandrager J-W, Schuuring E, Raap T, Philippo K, Kleiverda K, Kluin P: Interphase FISH detection of BCL2 rearrangement in follicular lymphoma using breakpoint-flanking probes. Genes Chromosomes cancer 27:85, 2000

Vandenberghe E, De Wolf Peeters C, Wlodarska I, Stul M, Louwagie A, Verhoef G, Thomas J, Criel A, Cassiman J J, Mecucci C: Chromosome 11q rearrangements in B non Hodgkin's lymphoma. Br J Haematol 81:212, 1992

Verma R S, and Babu A. Human chromosomes. Manual of basic techniques. New York, Pergamon Press, 1989

Weber J, W. Scheid, H. Traut Time-saving in biological dosimetry by using the automatic metaphase finder Metafer2, Mutation Research, 272, 31-34, 1992

Weisenburger D D: Mantle cell lymphoma, in Knowles DM(ed): Neoplastic hematopathology. Baltimore, Md., Williams & Wilkins 1992, P 617

Weisenburger D D. Epidemiology of non-Hodgkin's lymphoma: recent findings regarding an emerging epidemic. Ann. Oncol. 5 Suppl 1:19-24, 1994

Williams M E, Meeker T C, Swerdlow S H: Rearrangement of the chromosome 11 bcl-1 locus in centrocytic lymphoma: analysis with multiple breakpoint probes. Blood 78:493, 1991

Williams M E, Swerdlow S H, Rosenberg C L, Arnold A: Chromosome 11 translocation breakpoints at the PRAD1/cyclin D1 gene locus in centrocytic lymphoma. Leukemia, 7:241 1993

Wlodarska I, Schoenmakers E, Kas K, Merregaert J, Lemahieu V, Weier U, Van den Berghe H: Van de Ven W J M Molecular mapping of the chromosome 11 breakpoint of t(11;17)(q13;q21) in a t(11;14)(q13;q32)-positive B non-Hodgkin's lymphoma. Genes Chromosomes Cancer 8:224, 1993

Yarkoni S, Lishner M, Tangi 1, Nagler A, Lorberboum-Galski H. B-cell non-Hodgkin's lymphoma: Evidence for the t(14;18) translocation in all hematopoietic cell lineages. J Natl Cancer Inst 88: 14, 973, 1996

Zech L, Haglund U, Nilsson K, Klein G: Characteristic chromosomal abnormalities in biopsies and lymphoid-cell lines from patients with Burkitt's and non-Burkitt's lymphomas. Int J Cancer 17:47, 1976

Zeidler R, Joos S, Delecluse H J, Klobeck G, Vuillaume M, Lenoir G M, Bornkamm G W, Lipp M: Breakpoints of Burkitt's lymphoma t(8;22) translocation map within a distance of 300 kb downstream of MYC. Genes Chromosome Cancer 9:282, 1994.

What is claimed is:

1. A set of probes for detecting a human reciprocal chromosomal translocation between a potential breakpoint of a first gene located on a first human chromosome and a potential breakpoint of a second gene located on a second human chromosome and the set of probes comprises first and second nucleic acid probes from human genome,
   wherein:
   (1) the first nucleic acid probe bears a first label and hybridizes to a first region of the first human chromosome and the first region is outside of the first gene the first region is between the first gene and the centromere of the first human chromosome, and the first region is within 1 Mb region from the potential breakpoint within the first gene;

(2) the second nucleic acid probe bears a second label and hybridizes to a second region of the human second chromosome and the second region is outside of the second gene, the second region is between the second gene and one of the telomeres of the second human chromosome, and the second region is within 1 Mb from the potential breakpoint within the second gene;

(3) the first and second labels are different, when the first and second human chromosomes have undergone the translocation, the first and second nucleic acid probes hybridize to a derivative chromosome formed via the translocation between the potential breakpoint of the first gene located on the first human chromosome and the potential breakpoint of the second gene located on the second human chromosome, such that both the first and second labels appear on the derivative chromosome; and (ii) when the first and second chromosomes have not undergone the translocation, the first and second nucleic acid probes hybridize to the first and second human chromosomes respectively, such that only the first label appears on the first human chromosome and only the second label appears on the second human chromosome;

and wherein:

(a) the first gene is human BCL1 gene (BCL1), the second gene is human IGH gene (IGH), the first human chromosome is human chromosome 11, the second human chromosome is human chromosome 14, and the human reciprocal chromosomal translocation is t(11;14)(q13;q32); or (b) the first gene is human IGH gene, the second gene is human BCL-2 gene (BCL2), the first human chromosome is chromosome 14, the second chromosome is chromosome 18, and the human reciprocal chromosomal translocation is t(14;18)(q32;q21); or (c) the first gene is human MYC gene (MYC), the second gene is human IGH gene, the first human chromosome is human chromosome 8, the second human chromosome is human chromosome 14, and the human reciprocal chromosomal translocation is t(8;14)(q24;q32); or (d) the first gene is human BCR gene (BCR), the second gene is human ABL gene (ABL), the first human chromosome is human chromosome 22, the second human chromosome is human chromosome 9, and the human reciprocal chromosomal translocation is t(9;22)(q34;q11), or (e) the first gene is human IGH gene (IGH), the second gene is human BCL1 gene (BCL1), the first human chromosome is human chromosome 14, the second human chromosome is human chromosome 11, and the human reciprocal chromosomal translocation is t(11;14)(q13;q32); or (f) the first gene is human BCL-2 gene (BCL2), the second gene is human IGH gene, the first human chromosome is chromosome 18, the second human chromosome is human chromosome 14 and the reciprocal human chromosomal translocation is t(14;18)(q32;q21); or (g) the first gene is human IGH gene, the second gene is human MYC gene (MYC), the first human chromosome is human chromosome 14, the second human chromosome is human chromosome 8 and the human reciprocal chromosomal translocation is t(8;14)(q24;q32); or (h) the first gene is human ABL gene (ABL), the second gene is human BCR gene (BCR), the first human chromosome is human chromosome 9, the second human chromosome is human chromosome 22, and the human reciprocal chromosomal translocation is t(9;22)(q34;q11).

2. The set of probes of claim 1, wherein the first region or the second region is 100-300 kb in length.

3. The set of probes of claim 1, wherein the first region or the second region is 10-1000 kb in length.

4. The set of probes of claim 1, wherein the first gene is human BCL1 gene (BCL1), the second gene is human IGH gene (IGH), the first human chromosome is human chromosome 11, the second human chromosome is human chromosome 14, and the human reciprocal chromosomal translocation is t(11;14)(q13;q32).

5. The set of probes of claim 1, wherein the first gene is human IGH gene, the second gene is human BCL-2 gene (BCL2), the first human chromosome is human chromosome 14, the second chromosome is human chromosome 18, and the human reciprocal chromosomal translocation is t(14;18)(q32;q21).

6. The set of probes of claim 1, wherein the first gene is human MYC gene (MYC), the second gene is human IGH gene, the first human chromosome is human chromosome 8, the second human chromosome is human chromosome 14, and the human reciprocal chromosomal translocation is t(8;14)(q24;q32).

7. The set of probes of claim 1, wherein the first gene is human BCR gene (BCR), the second gene is human ABL gene (ABL), the first human chromosome is human chromosome 22, the second chromosome is human chromosome 9, and the human reciprocal chromosomal translocation is t(9;22)(q34;q11).

8. The set of probes of claim 1, wherein the first gene is human IGH gene (IGH), the second gene is human BCL1 gene (BCL1), the first human chromosome is human chromosome 14, the second human chromosome is human chromosome 11, and the human reciprocal chromosomal translocation is t(11;14)(q13;q32).

9. The set of probes of claim 1, wherein the first gene is human BCL-2 gene (BCL2), the second gene is human IGH gene, the first human chromosome is human chromosome 18, the second human chromosome is human chromosome 14, and the reciprocal human chromosomal translocation is t(14;18)(q32;q21).

10. The set of probes of claim 1, wherein the first gene is human IGH gene, the second gene is human MYC gene (MYC), the first human chromosome is human chromosome 14, the second human chromosome is human chromosome 8, and the human reciprocal chromosomal translocation is t(8;14)(q24;q32).

11. The set of probes of claim 1, wherein the first gene is human ABL gene (ABL), the second gene is human BCR gene (BCR), the first human chromosome is human chromosome 9, the second human chromosome is human chromosome 22, and the human reciprocal chromosomal translocation is t(9;22)(q34;q11).

* * * * *